(12) United States Patent
Klostermann et al.

(10) Patent No.: US 10,370,413 B2
(45) Date of Patent: Aug. 6, 2019

(54) KV1.3 POTASSIUM CHANNEL ANTAGONISTS

(71) Applicant: cgtx-Peptide Development GmbH, Martinsried (DE)

(72) Inventors: Andreas Klostermann, Martinsried (DE); Jörg Stockhaus, Martinsried (DE)

(73) Assignee: cgtx-Peptide Development GmbH, Martinsried (DE)

( * ) Notice: Subject to any disclaimer, the term of this patent is extended or adjusted under 35 U.S.C. 154(b) by 0 days.

(21) Appl. No.: 15/309,781

(22) PCT Filed: May 7, 2015

(86) PCT No.: PCT/EP2015/060073
§ 371 (c)(1),
(2) Date: Nov. 8, 2016

(87) PCT Pub. No.: WO2015/169901
PCT Pub. Date: Nov. 12, 2015

(65) Prior Publication Data
US 2017/0137470 A1    May 18, 2017

(30) Foreign Application Priority Data
May 8, 2014 (GB) .................... 1408135.0

(51) Int. Cl.
| | | |
|---|---|---|
| *A61K 38/00* | (2006.01) | |
| *C07K 14/00* | (2006.01) | |
| *C07K 7/00* | (2006.01) | |
| *C07K 7/08* | (2006.01) | |
| *C07K 14/705* | (2006.01) | |
| *C07K 14/47* | (2006.01) | |

(52) U.S. Cl.
CPC .......... *C07K 14/00* (2013.01); *C07K 14/4703* (2013.01); *C07K 14/705* (2013.01); *A61K 38/00* (2013.01)

(58) Field of Classification Search
CPC .......... A61K 38/00; C07K 14/00; C07K 7/00; C07K 7/08
USPC .......... 514/1.1, 21.3; 530/300, 324
See application file for complete search history.

(56) References Cited

U.S. PATENT DOCUMENTS

2007/0071764 A1 * 3/2007 Sullivan .......... A61K 47/48215
424/178.1
2009/0318341 A1   12/2009 Sullivan et al.

OTHER PUBLICATIONS

Valverde, P., et al., "Selective Blockade of Voltage-Gated Potassium Channels Reduces Inflammatory Bone Resorption in Experimental Periodontal Disease," Journal of Bone and Mineral Research, vol. 19, No. 1, 2004.
Xu Jianchao et al., "The voltage-gated potassium channel Kv1.3 regulates energy homeostasis and body weight", Human Molecular Genetics, Oxford University Press, Mar. 1, 2003, vol. 12, No. 5, pp. 551-559.
International Search Report and Written Opinion in corresponding PCT Application No. PCT/EP2015/060073, dated Jul. 31, 2015.

* cited by examiner

*Primary Examiner* — Julie Ha
(74) *Attorney, Agent, or Firm* — Knobbe Martens Olson & Bear LLP

(57) ABSTRACT

Compounds which selectively bind to and inhibit the activity of the potassium channel Kv1.3 are described. Pharmaceutical compositions comprising such compounds and the use of said compounds and said pharmaceutical compositions for the treatment or prevention of autoimmune diseases, obesity, parodontitis and/or tissue transplant rejection are also described.

10 Claims, 48 Drawing Sheets
Specification includes a Sequence Listing.

Figure 1A
Binding of HsTx 1 to Kv1.1

HsTx-1 on Kv1.1
Kd = 11.3 µM

Figure 1B
Binding of HsTx1 to Kv1.3

HsTx-1 on Kv1.3
Kd = 25 ± 2.1nM

Binding of HsTx1 to Kv1.5

HsTx-1 >10µM without effect on Kv1.5

Binding of cgtx 544 to Kv1.1

Binding of cgtx 544 to Kv1.3

Binding of cgtx 544 to Kv1.5

Figure 2

| peptide | SEQ ID NO | Sequence |
|---|---|---|
| cgtx 538 | SEQ ID NO.: 9 | ascrtpkdcadpcrketgcpnakcmnrkckcygc |
| cgtx 539 | SEQ ID NO.: 12 | ascrtpkqcarpcrkqtgcpygkcmnrkckcnrc |
| cgtx 540 | SEQ ID NO.: 15 | ascrtpkqcyphckketgcpygkcmnrkckcnrc |
| cgtx 541 | SEQ ID NO.: 18 | arcrtprdcadpcrketgcpygkcmnrkcrcnrc |
| cgtx 542 | SEQ ID NO.: 19 | arcrtsrncakpcrkqtgcpygkcmnrkcrcnrc |
| cgtx 543 | SEQ ID NO.: 29 | gvpinvsctgspqcikpckdatgcpygkcmnrkckcnrc |
| cgtx 544 | SEQ ID NO.: 25 | tiinvkctspkqclppckaqtgcpygkcmnrkckcnrc |
| cgtx 545 | SEQ ID NO.: 22 | isctnpkqcyphckketgcpygkcmnrkckcnrc |
| cgtx 546 | SEQ ID NO.: 30 | gviinvkckisrqclepckkatgcpygkcmnrkckcnrc |
| cgtx 547 | SEQ ID NO.: 26 | qftnvscttskecwsvcqrltgcpygkcmnrkckcnrc |
| cgtx 548 | SEQ ID NO.: 31 | gvpinvkctgspqclkpckdatgcpygkcmnrkckcnrc |
| HsTx 1 | SEQ ID NO.: 32 | ASCRTPKDCADPCRKETGCPYGKCMNRKCKCNRC |

Figure 4
a) SF 21 cells
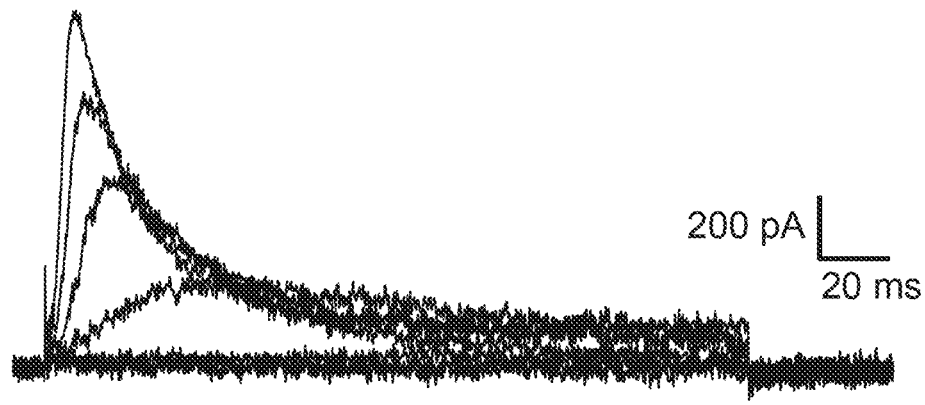
b) T$_{EM}$ cells
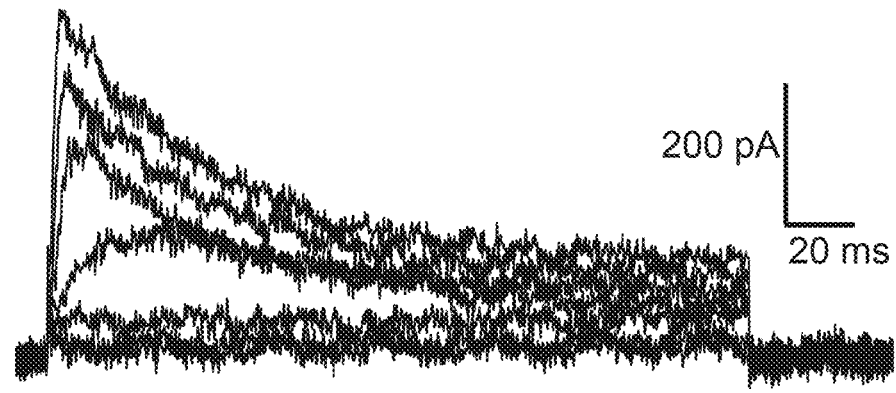
c) Pulse control
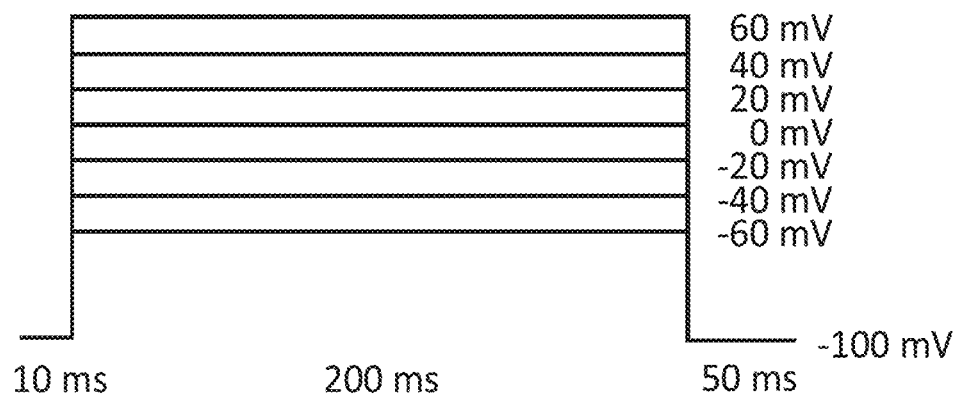

SF 21 cells

T_EM cells

Figure 16
a)
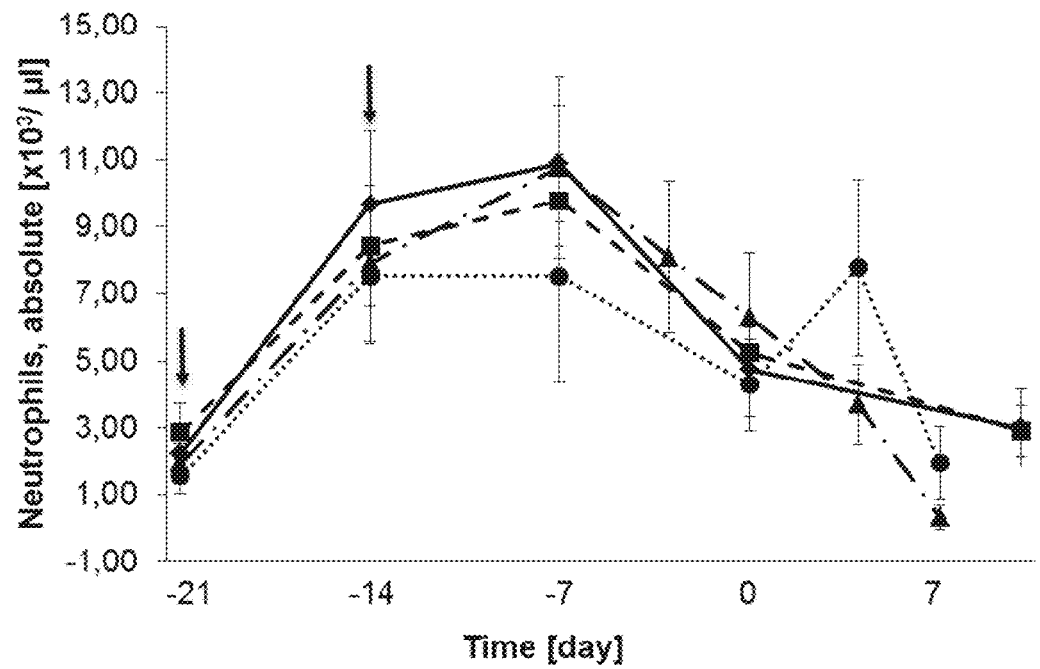
b)
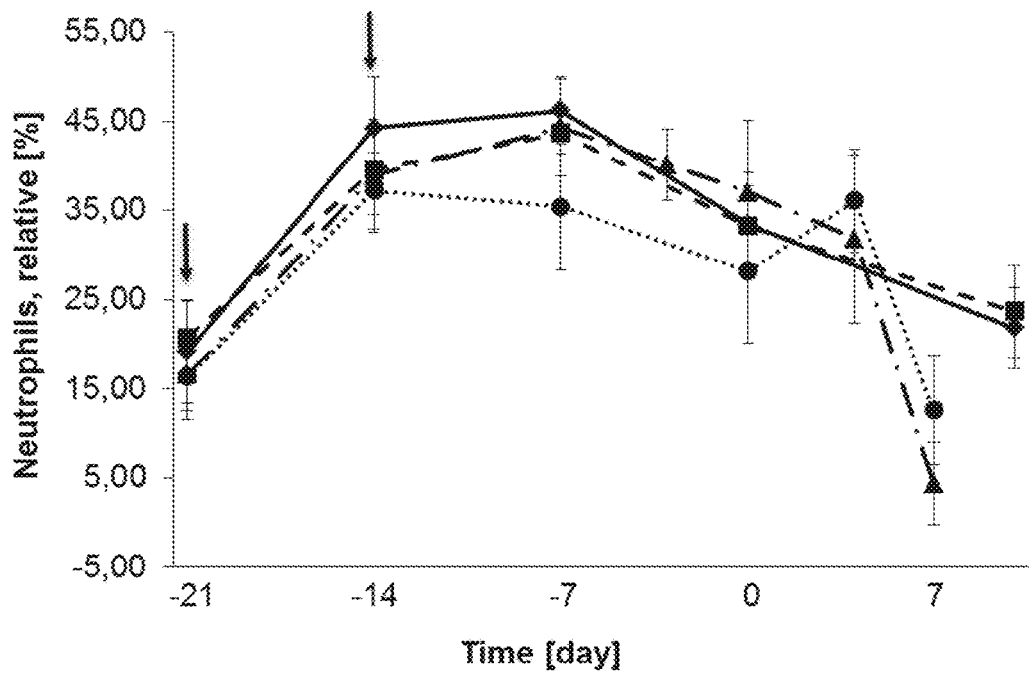

Figure 17
a)
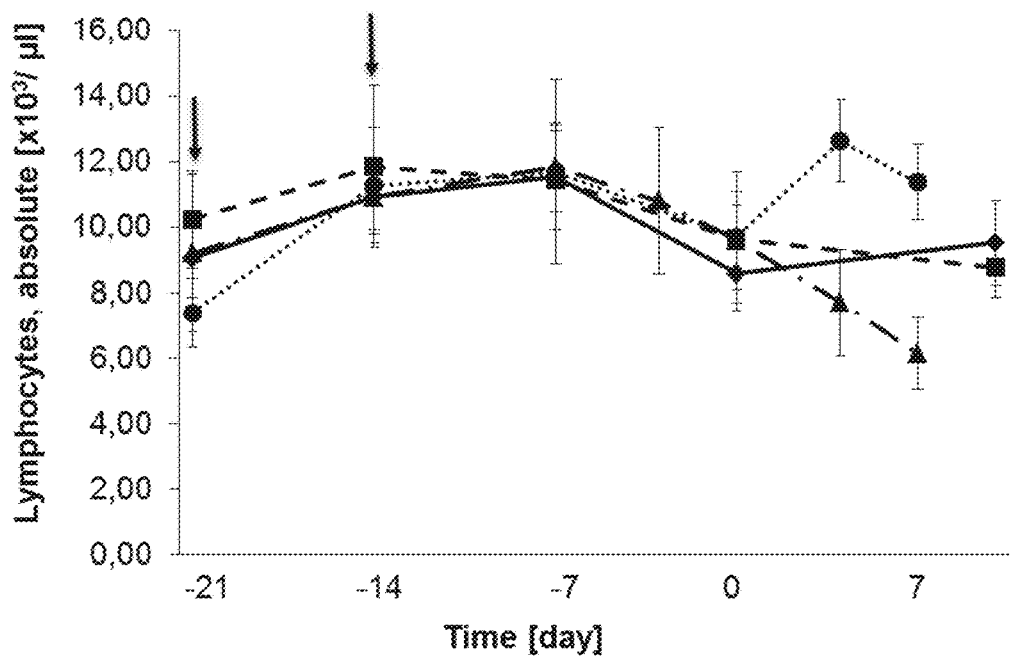
b)
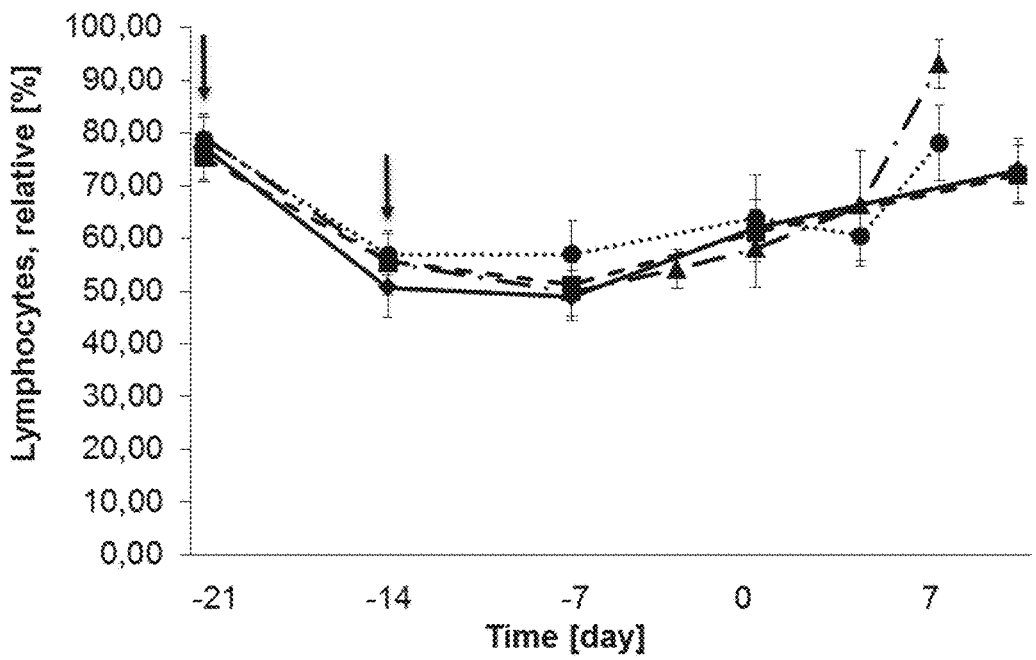

Figure 26
A
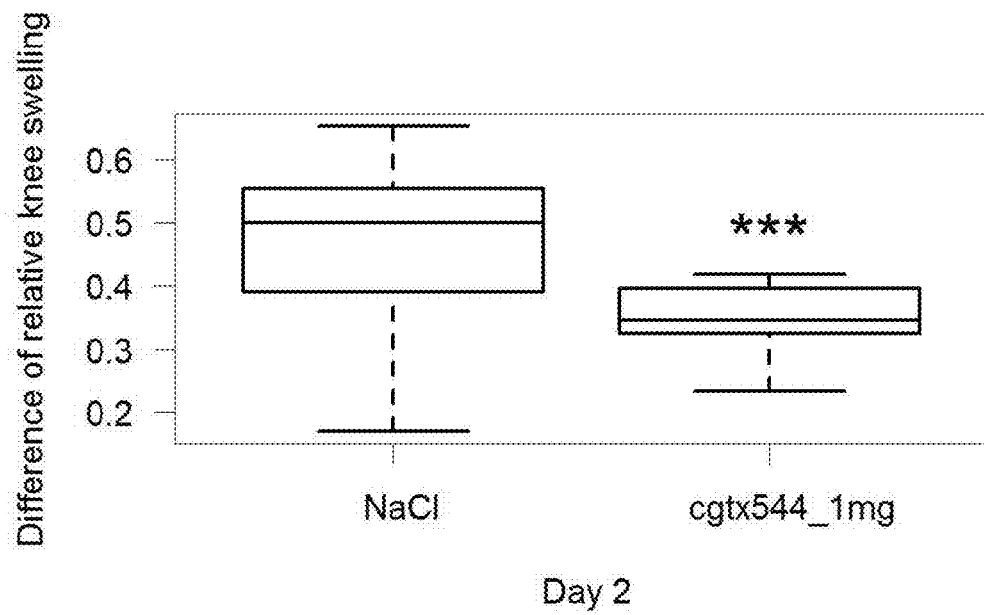
B
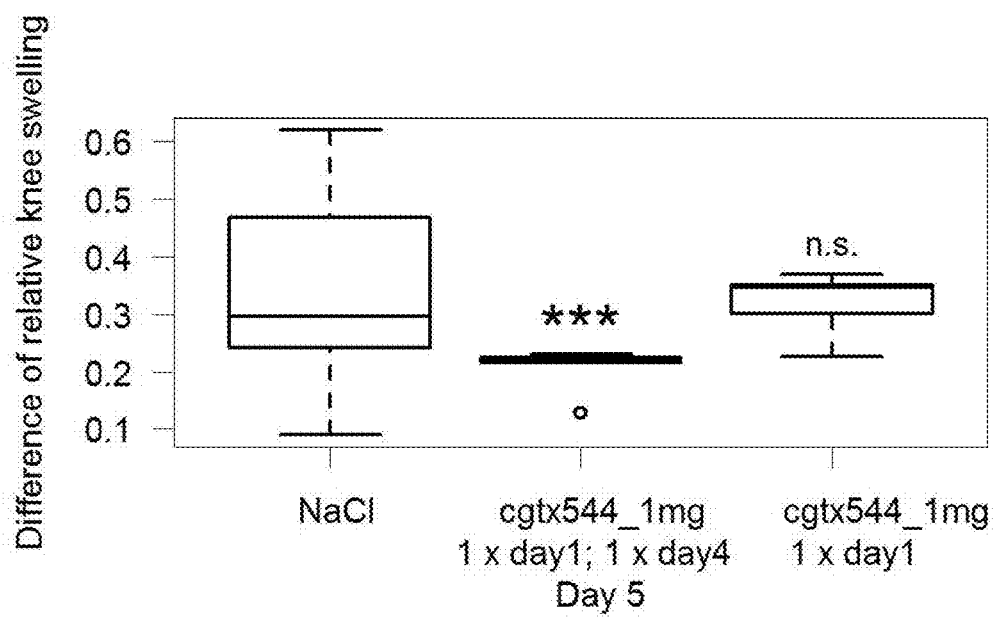

Figure 27

|  | #08 | #09 | #10 | #11 | #12 | #13 | #14 | mBSA |
|---|---|---|---|---|---|---|---|---|
| Gr. H d7 | | | | | | | | 0,1 µg |
| | | | | | | | | 0,5 µg |

|  | #08 | #09 | #10 | #11 | #12 | #13 | #14 | mBSA |
|---|---|---|---|---|---|---|---|---|
| Gr. I d7 | | | | | | | | 0,1 µg |
| | | | | | | | | 0,5 µg |

|  | #01 | #02 | mBSA |
|---|---|---|---|
| Gr. I d12 | | | 0,1 µg |
| | | | 0,5 µg |

|  | #06 | #07 | mBSA |
|---|---|---|---|
| Gr. F d7 | | | 0,1 µg |
| | | | 0,5 µg |

Figure 28
A
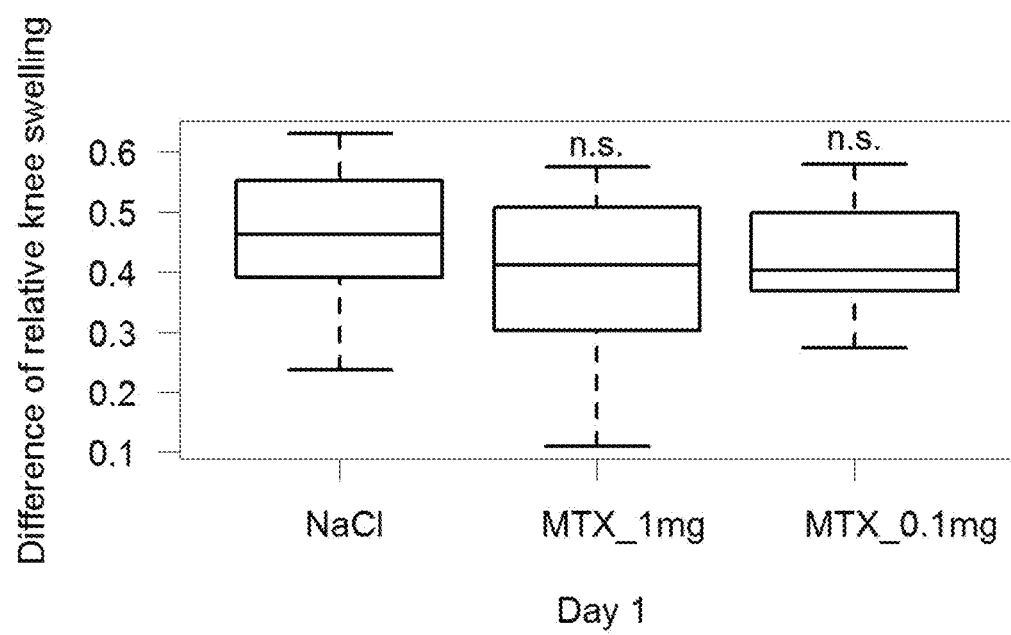
B
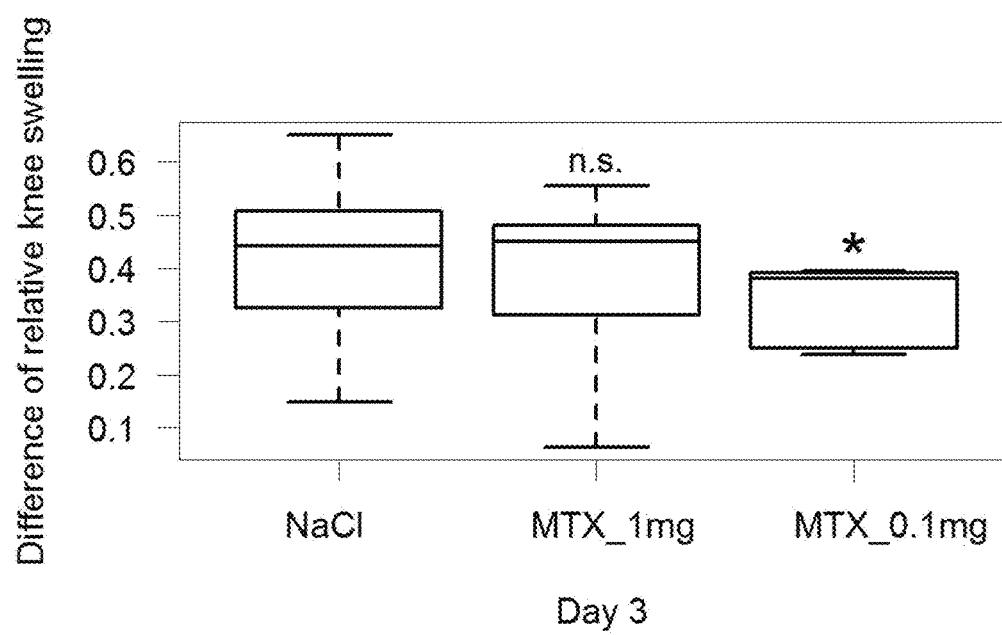

Figure 30

| | | |
|---|---|---|
| P/N: | | Time-Base: LC246 |
| Batch: | 2014_02_24 (LC246) | Operator: poweruser |
| Sequence Name: | 86 | Recording Time: 26.2.2014 9:34 |
| Sample Number: | | Analysis Number: |
| Column: | ACQUITY UPLC BEH PST 130 C18 (2.1x150mm, 1.7um;2008734, 02043306415507 | Sample Type: unknown |
| | | Vial Number: BE2 |
| | | Injection Volume: 10.0 uL |
| | | Sample Description: aus Reakt. |
| Column Number: | | Wavelength (nm): 220.0 |
| Column Temp.: | 50.0 °C | Bandwidth (nm): 8 |
| Gradient: | TFA 1-05%-30-35% 0_4ML | Run Time (min): 31.00 |
| Eluent A: | 0.05% TFA, 1% ACN in H2O | Quantif. Method: INTEGRATION |
| Eluent B: | 0.05% TFA in ACN | |
| Eluent C: | ACN/H2O 1:1 | |
| Eluent D: | ACN/H2O 1:4 | |

Figure 31
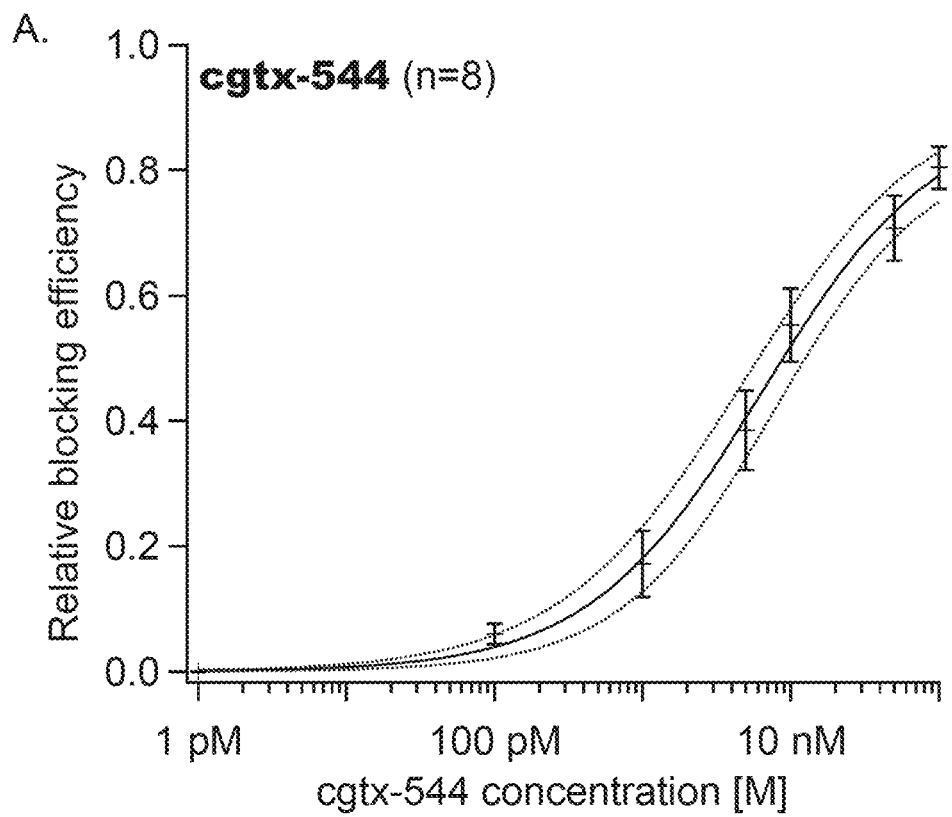
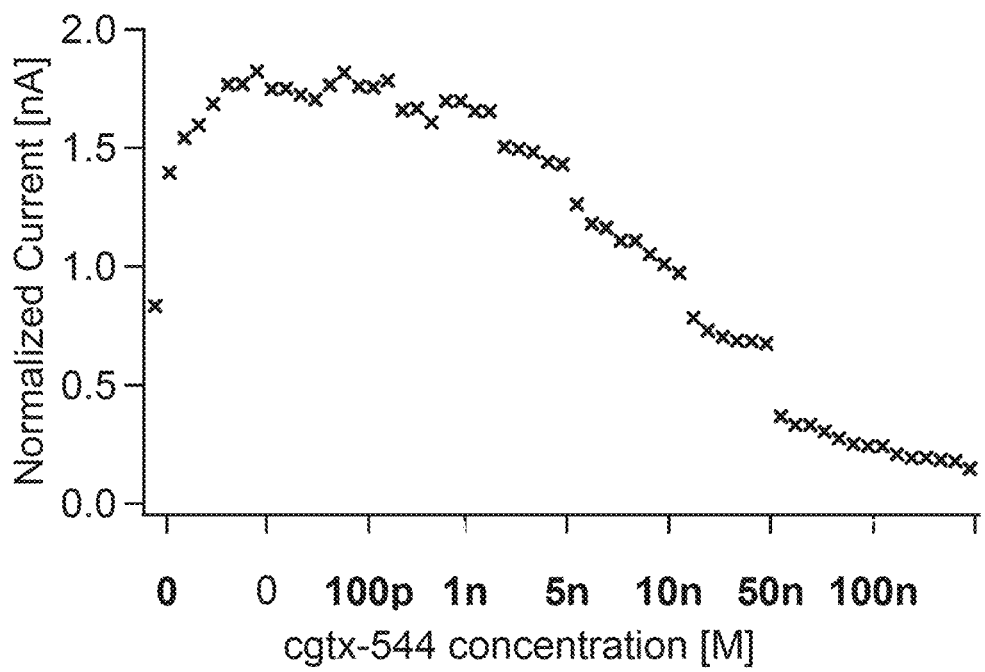

Fig. 31 – continued
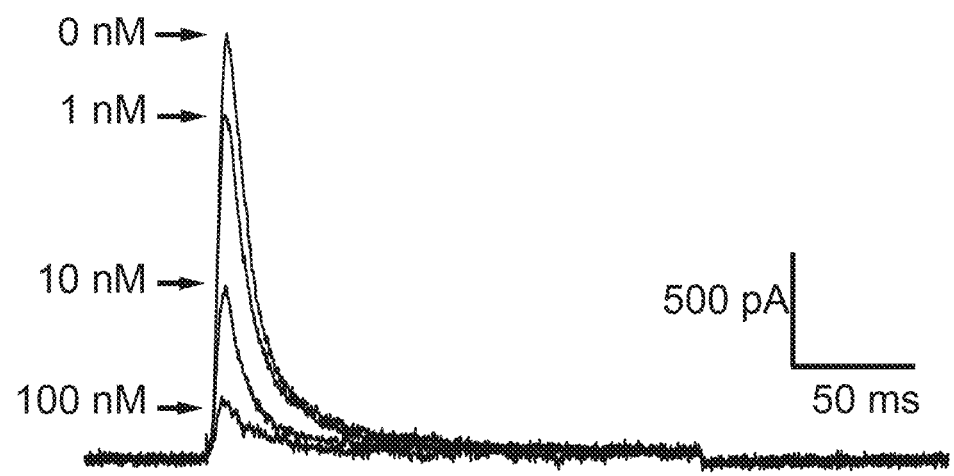

Fig. 32 – continued
C.
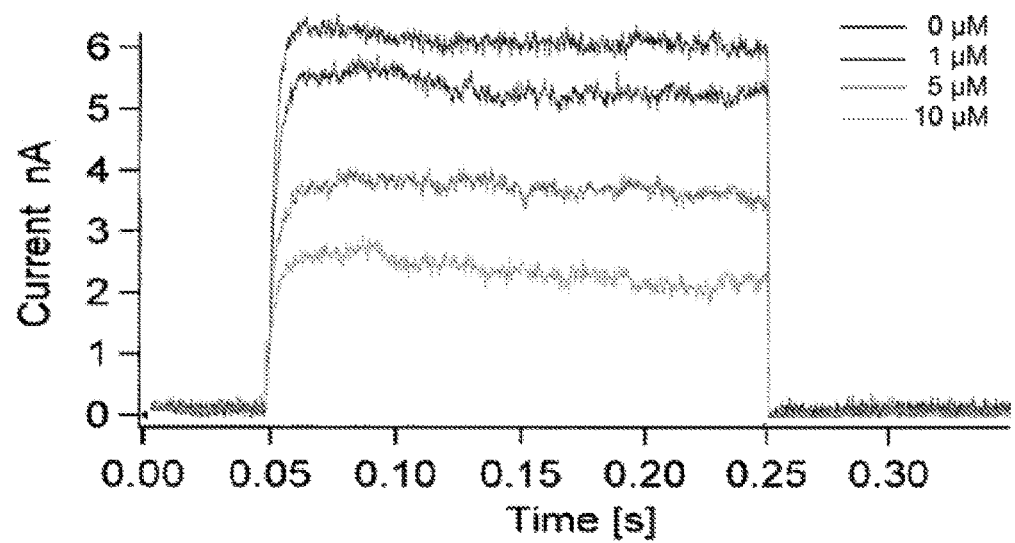

Fig. 32 – continued
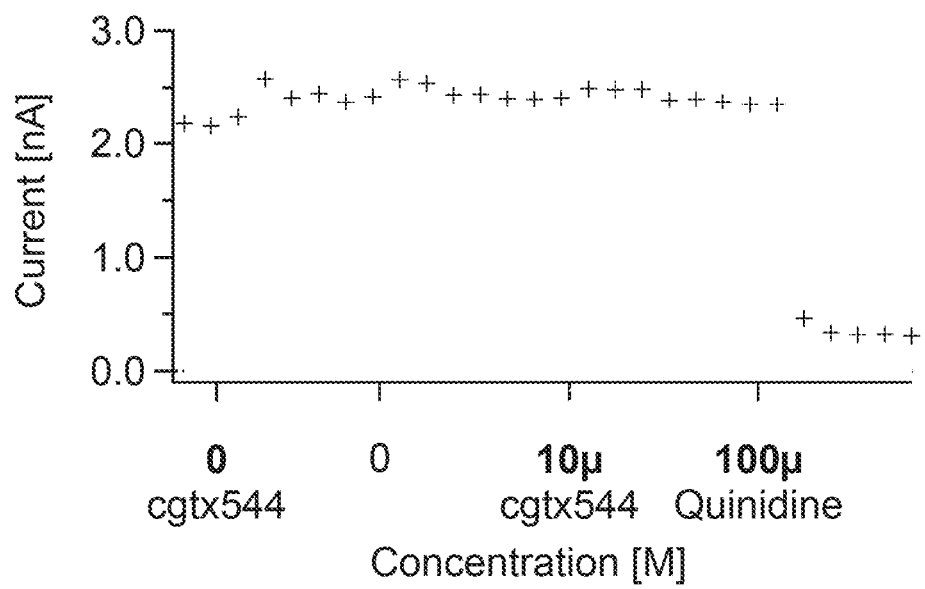
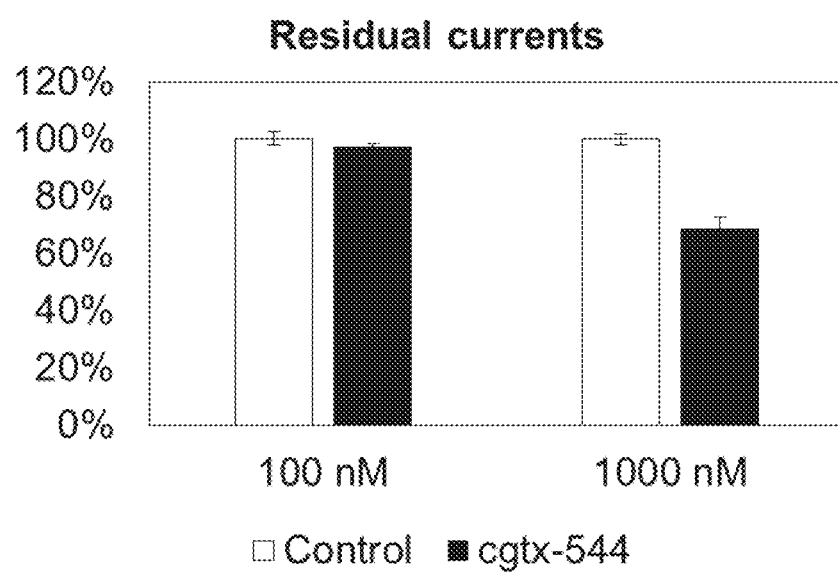

Figure 35
A)
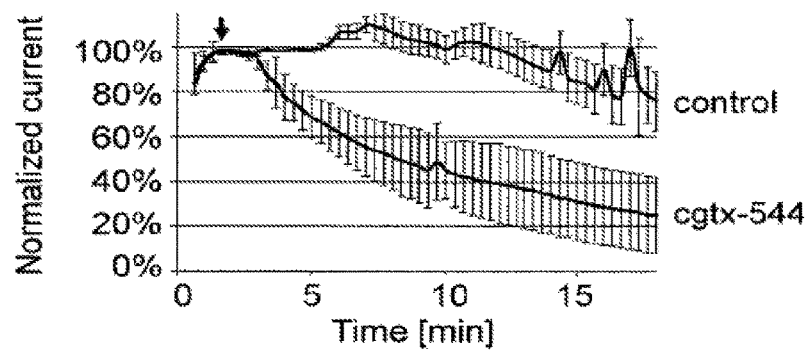
B)
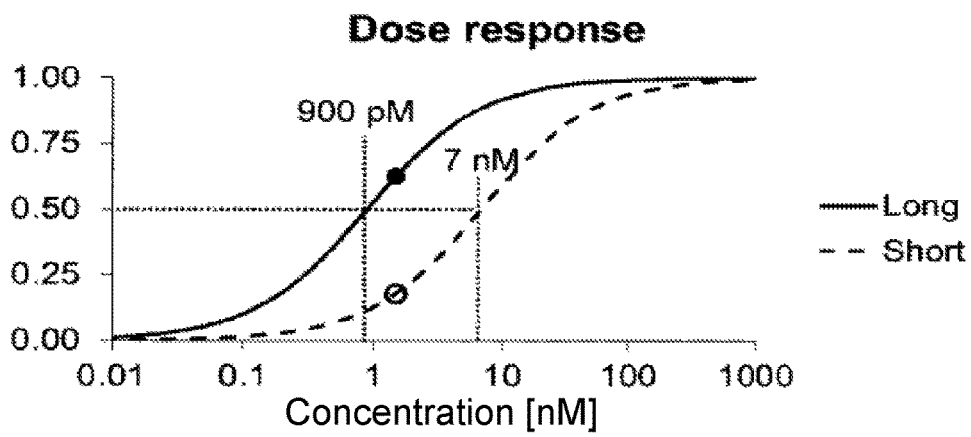
C)
| Compound | Kv1.3 $K_d$ / $IC_{50}$ | Kv1.1 $K_d$ / $IC_{50}$ | Selectivity Ratio |
|---|---|---|---|
| cgtx-544 (short) | 6,900 pM | 6M pM | 869,6 |
| cgtx-544 (prolonged) | 900 pM | 6M pM | 6500,0 |

SEQUENCE LISTING

<160> NUMBER OF SEQ ID NOS: 32

<210> SEQ ID NO 1
<211> LENGTH: 34
<212> TYPE: PRT
<213> ORGANISM: Artificial Sequence
<220> FEATURE:
<223> OTHER INFORMATION: peptide compound
<220> FEATURE:

-continued

```
<221> NAME/KEY: VARIANT
<222> LOCATION: (1)..(1)
<223> OTHER INFORMATION: /replace="Val"
      /replace="Ile"
      /replace="Leu"
<220> FEATURE:
<221> NAME/KEY: VARIANT
<222> LOCATION: (2)..(2)
<223> OTHER INFORMATION: /replace="Arg"
      /replace="Lys"
      /replace="Thr"
      /replace="Tyr"
<220> FEATURE:
<221> NAME/KEY: VARIANT
<222> LOCATION: (4)..(4)
<223> OTHER INFORMATION: /replace="Thr"
      /replace="Lys"
      /replace="Ser"
      /replace="Tyr"
<220> FEATURE:
<221> NAME/KEY: VARIANT
<222> LOCATION: (5)..(5)
<223> OTHER INFORMATION: /replace="Gly"
      /replace="Ser"
      /replace="Asn"
      /replace="Ile"
      /replace="Lys"
      /replace="Gln"
      /replace="Ala"
      /replace="Val"
      /replace="Leu"
      /replace="Tyr"
<220> FEATURE:
<221> NAME/KEY: VARIANT
<222> LOCATION: (6)..(6)
<223> OTHER INFORMATION: /replace="Ser"
      /replace="Thr"
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (8)..(8)
<223> OTHER INFORMATION: /replace="Gln"
      /replace="Asn"
      /replace="Glu"
<220> FEATURE:
<221> NAME/KEY: VARIANT
<222> LOCATION: (10)..(10)
<223> OTHER INFORMATION: /replace="Tyr"
      /replace="Ile"
      /replace="Leu"
      /replace="Trp"
      /replace="Ser"
      /replace="Thr"
      /replace="Val"
      /replace="Leu"
      /replace="Phe"
<220> FEATURE:
<221> NAME/KEY: VARIANT
<222> LOCATION: (11)..(11)
<223> OTHER INFORMATION: /replace="Arg"
      /replace="Pro"
      /replace="Lys"
      /replace="Glu"
      /replace="Ser"
      /replace="Thr"
      /replace="Tyr"
<220> FEATURE:
<221> NAME/KEY: VARIANT
<222> LOCATION: (12)..(12)
<223> OTHER INFORMATION: /replace="His"
      /replace="Val"
      /replace="Ile"
      /replace="Leu"
      /replace="Ala"
<220> FEATURE:
```

```
<221> NAME/KEY: VARIANT
<222> LOCATION: (14)..(14)
<223> OTHER INFORMATION: /replace="Lys"
      /replace="Gln"
      /replace="Asn"
<220> FEATURE:
<221> NAME/KEY: VARIANT
<222> LOCATION: (15)..(15)
<223> OTHER INFORMATION: /replace="Asp"
      /replace="Ala"
      /replace="Arg"
      /replace="Glu"
      /replace="Val"
      /replace="Leu"
      /replace="Ile"
<220> FEATURE:
<221> NAME/KEY: VARIANT
<222> LOCATION: (16)..(16)
<223> OTHER INFORMATION: /replace="Gln"
      /replace="Ala"
      /replace="Leu"
      /replace="Asp"
      /replace="Asn"
      /replace="Val"
      /replace="Ile"
<220> FEATURE:
<221> NAME/KEY: VARIANT
<222> LOCATION: (21)..(21)
<223> OTHER INFORMATION: /replace="Tyr"
      /replace="Ser"
      /replace="Thr"
      /replace="Gln"
<220> FEATURE:
<221> NAME/KEY: VARIANT
<222> LOCATION: (22)..(22)
<223> OTHER INFORMATION: /replace="Gly"
      /replace="Val"
      /replace="Ile"
      /replace="Leu"
<220> FEATURE:
<221> NAME/KEY: VARIANT
<222> LOCATION: (30)..(30)
<223> OTHER INFORMATION: /replace="Arg"
<220> FEATURE:
<221> NAME/KEY: VARIANT
<222> LOCATION: (32)..(32)
<223> OTHER INFORMATION: /replace="Asn"
      /replace="Gln"
      /replace="Thr"
      /replace="Ser"
<220> FEATURE:
<221> NAME/KEY: VARIANT
<222> LOCATION: (33)..(33)
<223> OTHER INFORMATION: /replace="Arg"
      /replace="Lys"

<400> SEQUENCE: 1

Ala Ser Cys Arg Thr Pro Lys Asp Cys Ala Asp Pro Cys Arg Lys Glu
1               5                   10                  15

Thr Gly Cys Pro Asn Ala Lys Cys Met Asn Arg Lys Cys Lys Cys Tyr
            20                  25                  30

Gly Cys

<210> SEQ ID NO 2
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
      /replace="Ile"
<220> FEATURE:
```

```
<221> NAME/KEY: VARIANT
<222> LOCATION: (2)..(2)
<223> OTHER INFORMATION: /replace="Arg"
      /replace="Lys"
<220> FEATURE:
<221> NAME/KEY: VARIANT
<222> LOCATION: (4)..(4)
<223> OTHER INFORMATION: /replace="Thr"
      /replace="Lys"
<220> FEATURE:
<221> NAME/KEY: VARIANT
<222> LOCATION: (5)..(5)
<223> OTHER INFORMATION: /replace="Gly"
      /replace="Ser"
      /replace="Asn"
      /replace="Ile"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (8)..(8)
<223> OTHER INFORMATION: /replace="Gln"
      /replace="Asn"
      /replace="Glu"
<220> FEATURE:
<221> NAME/KEY: VARIANT
<222> LOCATION: (10)..(10)
<223> OTHER INFORMATION: /replace="Tyr"
      /replace="Ile"
      /replace="Leu"
      /replace="Trp"
<220> FEATURE:
<221> NAME/KEY: VARIANT
<222> LOCATION: (11)..(11)
<223> OTHER INFORMATION: /replace="Arg"
      /replace="Pro"
      /replace="Lys"
      /replace="Glu"
      /replace="Ser"
<220> FEATURE:
<221> NAME/KEY: VARIANT
<222> LOCATION: (12)..(12)
<223> OTHER INFORMATION: /replace="His"
      /replace="Val"
<220> FEATURE:
<221> NAME/KEY: VARIANT
<222> LOCATION: (14)..(14)
<223> OTHER INFORMATION: /replace="Lys"
      /replace="Gln"
<220> FEATURE:
<221> NAME/KEY: VARIANT
<222> LOCATION: (15)..(15)
<223> OTHER INFORMATION: /replace="Asp"
      /replace="Ala"
      /replace="Arg"
<220> FEATURE:
<221> NAME/KEY: VARIANT
<222> LOCATION: (16)..(16)
<223> OTHER INFORMATION: /replace="Gln"
      /replace="Ala"
      /replace="Leu"
<220> FEATURE:
<221> NAME/KEY: VARIANT
<222> LOCATION: (21)..(21)
<223> OTHER INFORMATION: /replace="Tyr"
<220> FEATURE:
<221> NAME/KEY: VARIANT
<222> LOCATION: (22)..(22)
<223> OTHER INFORMATION: /replace="Gly"
<220> FEATURE:
<221> NAME/KEY: VARIANT
<222> LOCATION: (30)..(30)
```

```
<223> OTHER INFORMATION: /replace="Arg"
<220> FEATURE:
<221> NAME/KEY: VARIANT
<222> LOCATION: (32)..(32)
<223> OTHER INFORMATION: /replace="Asn"
<220> FEATURE:
<221> NAME/KEY: VARIANT
<222> LOCATION: (33)..(33)
<223> OTHER INFORMATION: /replace="Arg"

<400> SEQUENCE: 2

Ala Ser Cys Arg Thr Pro Lys Asp Cys Ala Asp Pro Cys Arg Lys Glu
1               5                   10                  15

Thr Gly Cys Pro Asn Ala Lys Cys Met Asn Arg Lys Cys Lys Cys Tyr
            20                  25                  30

Gly Cys

<210> SEQ ID NO 3
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
      /replace="Ile"
      /replace="Leu"
<220> FEATURE:
<221> NAME/KEY: VARIANT
<222> LOCATION: (2)..(2)
<223> OTHER INFORMATION: /replace="Arg"
      /replace="Lys"
      /replace="Thr"
      /replace="Tyr"
<220> FEATURE:
<221> NAME/KEY: VARIANT
<222> LOCATION: (4)..(4)
<223> OTHER INFORMATION: /replace="Thr"
      /replace="Lys"
      /replace="Ser"
      /replace="Tyr"
<220> FEATURE:
<221> NAME/KEY: VARIANT
<222> LOCATION: (5)..(5)
<223> OTHER INFORMATION: /replace="Gly"
      /replace="Ser"
      /replace="Asn"
      /replace="Ile"
      /replace="Lys"
      /replace="Gln"
      /replace="Ala"
      /replace="Val"
      /replace="Leu"
      /replace="Tyr"
<220> FEATURE:
<221> NAME/KEY: VARIANT
<222> LOCATION: (6)..(6)
<223> OTHER INFORMATION: /replace="Ser"
      /replace="Thr"
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (8)..(8)
<223> OTHER INFORMATION: /replace="Gln"
      /replace="Asn"
      /replace="Glu"
<220> FEATURE:
<221> NAME/KEY: VARIANT
<222> LOCATION: (10)..(10)
```

```
<223> OTHER INFORMATION: /replace="Tyr"
      /replace="Ile"
      /replace="Leu"
      /replace="Trp"
      /replace="Ser"
      /replace="Thr"
      /replace="Val"
      /replace="Leu"
      /replace="Phe"
<220> FEATURE:
<221> NAME/KEY: VARIANT
<222> LOCATION: (11)..(11)
<223> OTHER INFORMATION: /replace="Arg"
      /replace="Pro"
      /replace="Lys"
      /replace="Glu"
      /replace="Ser"
      /replace="Thr"
      /replace="Tyr"
<220> FEATURE:
<221> NAME/KEY: VARIANT
<222> LOCATION: (12)..(12)
<223> OTHER INFORMATION: /replace="His"
      /replace="Val"
      /replace="Ile"
      /replace="Leu"
      /replace="Ala"
<220> FEATURE:
<221> NAME/KEY: VARIANT
<222> LOCATION: (14)..(14)
<223> OTHER INFORMATION: /replace="Lys"
      /replace="Gln"
      /replace="Asn"
<220> FEATURE:
<221> NAME/KEY: VARIANT
<222> LOCATION: (15)..(15)
<223> OTHER INFORMATION: /replace="Asp"
      /replace="Ala"
      /replace="Arg"
      /replace="Glu"
      /replace="Val"
      /replace="Leu"
      /replace="Ile"
<220> FEATURE:
<221> NAME/KEY: VARIANT
<222> LOCATION: (16)..(16)
<223> OTHER INFORMATION: /replace="Gln"
      /replace="Ala"
      /replace="Leu"
      /replace="Asp"
      /replace="Asn"
      /replace="Val"
      /replace="Ile"
<220> FEATURE:
<221> NAME/KEY: VARIANT
<222> LOCATION: (30)..(30)
<223> OTHER INFORMATION: /replace="Arg"
<220> FEATURE:
<221> NAME/KEY: VARIANT
<222> LOCATION: (32)..(32)
<223> OTHER INFORMATION: /replace="Asn"
      /replace="Gln"
      /replace="Thr"
      /replace="Ser"
<220> FEATURE:
<221> NAME/KEY: VARIANT
<222> LOCATION: (33)..(33)
<223> OTHER INFORMATION: /replace="Arg"
      /replace="Lys"

<400> SEQUENCE: 3

Ala Ser Cys Arg Thr Pro Lys Asp Cys Ala Asp Pro Cys Arg Lys Glu
1               5                   10                  15

Thr Gly Cys Pro Asn Ala Lys Cys Met Asn Arg Lys Cys Lys Cys Tyr
            20                  25                  30

Gly Cys
```

```
<210> SEQ ID NO 4
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
      /replace="Ile"
<220> FEATURE:
<221> NAME/KEY: VARIANT
<222> LOCATION: (2)..(2)
<223> OTHER INFORMATION: /replace="Arg"
      /replace="Lys"
<220> FEATURE:
<221> NAME/KEY: VARIANT
<222> LOCATION: (4)..(4)
<223> OTHER INFORMATION: /replace="Thr"
      /replace="Lys"
<220> FEATURE:
<221> NAME/KEY: VARIANT
<222> LOCATION: (5)..(5)
<223> OTHER INFORMATION: /replace="Gly"
      /replace="Ser"
      /replace="Asn"
      /replace="Ile"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (8)..(8)
<223> OTHER INFORMATION: /replace="Gln"
      /replace="Asn"
      /replace="Glu"
<220> FEATURE:
<221> NAME/KEY: VARIANT
<222> LOCATION: (10)..(10)
<223> OTHER INFORMATION: /replace="Tyr"
      /replace="Ile"
      /replace="Leu"
      /replace="Trp"
<220> FEATURE:
<221> NAME/KEY: VARIANT
<222> LOCATION: (11)..(11)
<223> OTHER INFORMATION: /replace="Arg"
      /replace="Pro"
      /replace="Lys"
      /replace="Glu"
      /replace="Ser"
<220> FEATURE:
<221> NAME/KEY: VARIANT
<222> LOCATION: (12)..(12)
<223> OTHER INFORMATION: /replace="His"
      /replace="Val"
<220> FEATURE:
<221> NAME/KEY: VARIANT
<222> LOCATION: (14)..(14)
<223> OTHER INFORMATION: /replace="Lys"
      /replace="Gln"
<220> FEATURE:
<221> NAME/KEY: VARIANT
<222> LOCATION: (15)..(15)
<223> OTHER INFORMATION: /replace="Asp"
      /replace="Ala"
      /replace="Arg"
<220> FEATURE:
<221> NAME/KEY: VARIANT
<222> LOCATION: (16)..(16)
```

```
<223> OTHER INFORMATION: /replace="Gln"
        /replace="Ala"
        /replace="Leu"
<220> FEATURE:
<221> NAME/KEY: VARIANT
<222> LOCATION: (30)..(30)
<223> OTHER INFORMATION: /replace="Arg"
<220> FEATURE:
<221> NAME/KEY: VARIANT
<222> LOCATION: (32)..(32)
<223> OTHER INFORMATION: /replace="Asn"
<220> FEATURE:
<221> NAME/KEY: VARIANT
<222> LOCATION: (33)..(33)
<223> OTHER INFORMATION: /replace="Arg"

<400> SEQUENCE: 4

Ala Ser Cys Arg Thr Pro Lys Asp Cys Ala Asp Pro Cys Arg Lys Glu
1               5                   10                  15

Thr Gly Cys Pro Asn Ala Lys Cys Met Asn Arg Lys Cys Lys Cys Tyr
            20                  25                  30

Gly Cys

<210> SEQ ID NO 5
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
        /replace="Ile"
        /replace="Leu"
<220> FEATURE:
<221> NAME/KEY: VARIANT
<222> LOCATION: (2)..(2)
<223> OTHER INFORMATION: /replace="Arg"
        /replace="Lys"
        /replace="Thr"
        /replace="Tyr"
<220> FEATURE:
<221> NAME/KEY: VARIANT
<222> LOCATION: (4)..(4)
<223> OTHER INFORMATION: /replace="Thr"
        /replace="Lys"
        /replace="Ser"
        /replace="Tyr"
<220> FEATURE:
<221> NAME/KEY: VARIANT
<222> LOCATION: (5)..(5)
<223> OTHER INFORMATION: /replace="Gly"
        /replace="Ser"
        /replace="Asn"
        /replace="Ile"
        /replace="Lys"
        /replace="Gln"
        /replace="Ala"
        /replace="Val"
        /replace="Leu"
        /replace="Tyr"
<220> FEATURE:
<221> NAME/KEY: VARIANT
<222> LOCATION: (6)..(6)
<223> OTHER INFORMATION: /replace="Ser"
        /replace="Thr"
<220> FEATURE:
<221> NAME/KEY: VARIANT
<222> LOCATION: (7)..(7)
<223> OTHER INFORMATION: /replace="Arg"
        /replace="Pro"
<220> FEATURE:
<221> NAME/KEY: VARIANT
<222> LOCATION: (8)..(8)
```

```
<223> OTHER INFORMATION: /replace="Gln"
      /replace="Asn"
      /replace="Glu"
<220> FEATURE:
<221> NAME/KEY: VARIANT
<222> LOCATION: (10)..(10)
<223> OTHER INFORMATION: /replace="Tyr"
      /replace="Ile"
      /replace="Leu"
      /replace="Trp"
      /replace="Ser"
      /replace="Thr"
      /replace="Val"
      /replace="Leu"
      /replace="Phe"
<220> FEATURE:
<221> NAME/KEY: VARIANT
<222> LOCATION: (11)..(11)
<223> OTHER INFORMATION: /replace="Arg"
      /replace="Pro"
      /replace="Lys"
      /replace="Glu"
      /replace="Ser"
      /replace="Thr"
      /replace="Tyr"
<220> FEATURE:
<221> NAME/KEY: VARIANT
<222> LOCATION: (12)..(12)
<223> OTHER INFORMATION: /replace="His"
      /replace="Val"
      /replace="Ile"
      /replace="Leu"
      /replace="Ala"
<220> FEATURE:
<221> NAME/KEY: VARIANT
<222> LOCATION: (14)..(14)
<223> OTHER INFORMATION: /replace="Lys"
      /replace="Gln"
      /replace="Asn"
<220> FEATURE:
<221> NAME/KEY: VARIANT
<222> LOCATION: (15)..(15)
<223> OTHER INFORMATION: /replace="Asp"
      /replace="Ala"
      /replace="Arg"
      /replace="Glu"
      /replace="Val"
      /replace="Leu"
      /replace="Ile"
<220> FEATURE:
<221> NAME/KEY: VARIANT
<222> LOCATION: (16)..(16)
<223> OTHER INFORMATION: /replace="Gln"
      /replace="Ala"
      /replace="Leu"
      /replace="Asp"
      /replace="Asn"
      /replace="Val"
      /replace="Ile"
<220> FEATURE:
<221> NAME/KEY: VARIANT
<222> LOCATION: (21)..(21)
<223> OTHER INFORMATION: /replace="Tyr"
      /replace="Ser"
      /replace="Thr"
      /replace="Gln"
<220> FEATURE:
<221> NAME/KEY: VARIANT
<222> LOCATION: (22)..(22)
<223> OTHER INFORMATION: /replace="Gly"
      /replace="Val"
      /replace="Ile"
      /replace="Leu"
<220> FEATURE:
<221> NAME/KEY: VARIANT
<222> LOCATION: (30)..(30)
<223> OTHER INFORMATION: /replace="Arg"

<400> SEQUENCE: 5
```

-continued

```
Ala Ser Cys Arg Thr Pro Lys Asp Cys Ala Asp Pro Cys Arg Lys Glu
1               5                   10                  15

Thr Gly Cys Pro Asn Ala Lys Cys Met Asn Arg Lys Cys Lys Cys Tyr
            20                  25                  30

Gly Cys

<210> SEQ ID NO 6
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
      /replace="Ile"
<220> FEATURE:
<221> NAME/KEY: VARIANT
<222> LOCATION: (2)..(2)
<223> OTHER INFORMATION: /replace="Arg"
      /replace="Lys"
<220> FEATURE:
<221> NAME/KEY: VARIANT
<222> LOCATION: (4)..(4)
<223> OTHER INFORMATION: /replace="Thr"
      /replace="Lys"
<220> FEATURE:
<221> NAME/KEY: VARIANT
<222> LOCATION: (5)..(5)
<223> OTHER INFORMATION: /replace="Gly"
      /replace="Ser"
      /replace="Asn"
      /replace="Ile"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (8)..(8)
<223> OTHER INFORMATION: /replace="Gln"
      /replace="Asn"
      /replace="Glu"
<220> FEATURE:
<221> NAME/KEY: VARIANT
<222> LOCATION: (10)..(10)
<223> OTHER INFORMATION: /replace="Tyr"
      /replace="Ile"
      /replace="Leu"
      /replace="Trp"
<220> FEATURE:
<221> NAME/KEY: VARIANT
<222> LOCATION: (11)..(11)
<223> OTHER INFORMATION: /replace="Arg"
      /replace="Pro"
      /replace="Lys"
      /replace="Glu"
      /replace="Ser"
<220> FEATURE:
<221> NAME/KEY: VARIANT
<222> LOCATION: (12)..(12)
<223> OTHER INFORMATION: /replace="His"
      /replace="Val"
<220> FEATURE:
<221> NAME/KEY: VARIANT
<222> LOCATION: (14)..(14)
<223> OTHER INFORMATION: /replace="Lys"
      /replace="Gln"
<220> FEATURE:
```

```
<221> NAME/KEY: VARIANT
<222> LOCATION: (15)..(15)
<223> OTHER INFORMATION: /replace="Asp"
      /replace="Ala"
      /replace="Arg"
<220> FEATURE:
<221> NAME/KEY: VARIANT
<222> LOCATION: (16)..(16)
<223> OTHER INFORMATION: /replace="Gln"
      /replace="Ala"
      /replace="Leu"
<220> FEATURE:
<221> NAME/KEY: VARIANT
<222> LOCATION: (21)..(21)
<223> OTHER INFORMATION: /replace="Tyr"
<220> FEATURE:
<221> NAME/KEY: VARIANT
<222> LOCATION: (22)..(22)
<223> OTHER INFORMATION: /replace="Gly"
<220> FEATURE:
<221> NAME/KEY: VARIANT
<222> LOCATION: (30)..(30)
<223> OTHER INFORMATION: /replace="Arg"

<400> SEQUENCE: 6

Ala Ser Cys Arg Thr Pro Lys Asp Cys Ala Asp Pro Cys Arg Lys Glu
1               5                   10                  15

Thr Gly Cys Pro Asn Ala Lys Cys Met Asn Arg Lys Cys Lys Cys Tyr
            20                  25                  30

Gly Cys

<210> SEQ ID NO 7
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
      /replace="Ile"
      /replace="Leu"
<220> FEATURE:
<221> NAME/KEY: VARIANT
<222> LOCATION: (2)..(2)
<223> OTHER INFORMATION: /replace="Arg"
      /replace="Lys"
      /replace="Thr"
      /replace="Tyr"
<220> FEATURE:
<221> NAME/KEY: VARIANT
<222> LOCATION: (4)..(4)
<223> OTHER INFORMATION: /replace="Thr"
      /replace="Lys"
      /replace="Ser"
      /replace="Tyr"
<220> FEATURE:
<221> NAME/KEY: VARIANT
<222> LOCATION: (5)..(5)
<223> OTHER INFORMATION: /replace="Gly"
      /replace="Ser"
      /replace="Asn"
      /replace="Ile"
      /replace="Lys"
      /replace="Gln"
      /replace="Ala"
      /replace="Val"
      /replace="Leu"
      /replace="Tyr"
<220> FEATURE:
<221> NAME/KEY: VARIANT
<222> LOCATION: (6)..(6)
<223> OTHER INFORMATION: /replace="Ser"
      /replace="Thr"
```

-continued

```
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (8)..(8)
<223> OTHER INFORMATION: /replace="Gln"
      /replace="Asn"
      /replace="Glu"
<220> FEATURE:
<221> NAME/KEY: VARIANT
<222> LOCATION: (10)..(10)
<223> OTHER INFORMATION: /replace="Tyr"
      /replace="Ile"
      /replace="Leu"
      /replace="Trp"
      /replace="Ser"
      /replace="Thr"
      /replace="Val"
      /replace="Leu"
      /replace="Phe"
<220> FEATURE:
<221> NAME/KEY: VARIANT
<222> LOCATION: (11)..(11)
<223> OTHER INFORMATION: /replace="Arg"
      /replace="Pro"
      /replace="Lys"
      /replace="Glu"
      /replace="Ser"
      /replace="Thr"
      /replace="Tyr"
<220> FEATURE:
<221> NAME/KEY: VARIANT
<222> LOCATION: (12)..(12)
<223> OTHER INFORMATION: /replace="His"
      /replace="Val"
      /replace="Ile"
      /replace="Leu"
      /replace="Ala"
<220> FEATURE:
<221> NAME/KEY: VARIANT
<222> LOCATION: (14)..(14)
<223> OTHER INFORMATION: /replace="Lys"
      /replace="Gln"
      /replace="Asn"
<220> FEATURE:
<221> NAME/KEY: VARIANT
<222> LOCATION: (15)..(15)
<223> OTHER INFORMATION: /replace="Asp"
      /replace="Ala"
      /replace="Arg"
      /replace="Glu"
      /replace="Val"
      /replace="Leu"
      /replace="Ile"
<220> FEATURE:
<221> NAME/KEY: VARIANT
<222> LOCATION: (16)..(16)
<223> OTHER INFORMATION: /replace="Gln"
      /replace="Ala"
      /replace="Leu"
      /replace="Asp"
      /replace="Asn"
      /replace="Val"
      /replace="Ile"
<220> FEATURE:
<221> NAME/KEY: VARIANT
<222> LOCATION: (30)..(30)
<223> OTHER INFORMATION: /replace="Arg"

<400> SEQUENCE: 7

Ala Ser Cys Arg Thr Pro Lys Asp Cys Ala Asp Pro Cys Arg Lys Glu
1               5                   10                  15

Thr Gly Cys Pro Asn Ala Lys Cys Met Asn Arg Lys Cys Lys Cys Tyr
            20                  25                  30
```

Gly Cys

<210> SEQ ID NO 8
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
    /replace="Ile"
<220> FEATURE:
<221> NAME/KEY: VARIANT
<222> LOCATION: (2)..(2)
<223> OTHER INFORMATION: /replace="Arg"
    /replace="Lys"
<220> FEATURE:
<221> NAME/KEY: VARIANT
<222> LOCATION: (4)..(4)
<223> OTHER INFORMATION: /replace="Thr"
    /replace="Lys"
<220> FEATURE:
<221> NAME/KEY: VARIANT
<222> LOCATION: (5)..(5)
<223> OTHER INFORMATION: /replace="Gly"
    /replace="Ser"
    /replace="Asn"
    /replace="Ile"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Arg"
    /replace="Pro"
<220> FEATURE:
<221> NAME/KEY: VARIANT
<222> LOCATION: (8)..(8)
<223> OTHER INFORMATION: /replace="Gln"
    /replace="Asn"
    /replace="Glu"
<220> FEATURE:
<221> NAME/KEY: VARIANT
<222> LOCATION: (10)..(10)
<223> OTHER INFORMATION: /replace="Tyr"
    /replace="Ile"
    /replace="Leu"
    /replace="Trp"
<220> FEATURE:
<221> NAME/KEY: VARIANT
<222> LOCATION: (11)..(11)
<223> OTHER INFORMATION: /replace="Arg"
    /replace="Pro"
    /replace="Lys"
    /replace="Glu"
    /replace="Ser"
<220> FEATURE:
<221> NAME/KEY: VARIANT
<222> LOCATION: (12)..(12)
<223> OTHER INFORMATION: /replace="His"
    /replace="Val"
<220> FEATURE:
<221> NAME/KEY: VARIANT
<222> LOCATION: (14)..(14)
<223> OTHER INFORMATION: /replace="Lys"
    /replace="Gln"
<220> FEATURE:
<221> NAME/KEY: VARIANT
<222> LOCATION: (15)..(15)
<223> OTHER INFORMATION: /replace="Asp"
    /replace="Ala"
    /replace="Arg"
<220> FEATURE:

```
<221> NAME/KEY: VARIANT
<222> LOCATION: (16)..(16)
<223> OTHER INFORMATION: /replace="Gln"
      /replace="Ala"
      /replace="Leu"
<220> FEATURE:
<221> NAME/KEY: VARIANT
<222> LOCATION: (30)..(30)
<223> OTHER INFORMATION: /replace="Arg"

<400> SEQUENCE: 8

Ala Ser Cys Arg Thr Pro Lys Asp Cys Ala Asp Pro Cys Arg Lys Glu
1               5                   10                  15

Thr Gly Cys Pro Asn Ala Lys Cys Met Asn Arg Lys Cys Lys Cys Tyr
            20                  25                  30

Gly Cys

<210> SEQ ID NO 9
<211> LENGTH: 34
<212> TYPE: PRT
<213> ORGANISM: Artificial Sequence
<220> FEATURE:
<223> OTHER INFORMATION: peptide compound cgtx 538

<400> SEQUENCE: 9

Ala Ser Cys Arg Thr Pro Lys Asp Cys Ala Asp Pro Cys Arg Lys Glu
1               5                   10                  15

Thr Gly Cys Pro Asn Ala Lys Cys Met Asn Arg Lys Cys Lys Cys Tyr
            20                  25                  30

Gly Cys

<210> SEQ ID NO 10
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
      /replace="Ile"
      /replace="Leu"
<220> FEATURE:
<221> NAME/KEY: VARIANT
<222> LOCATION: (2)..(2)
<223> OTHER INFORMATION: /replace="Arg"
      /replace="Lys"
      /replace="Thr"
      /replace="Tyr"
<220> FEATURE:
<221> NAME/KEY: VARIANT
<222> LOCATION: (4)..(4)
<223> OTHER INFORMATION: /replace="Thr"
      /replace="Lys"
      /replace="Ser"
      /replace="Tyr"
<220> FEATURE:
<221> NAME/KEY: VARIANT
<222> LOCATION: (5)..(5)
<223> OTHER INFORMATION: /replace="Gly"
      /replace="Ser"
      /replace="Asn"
      /replace="Ile"
      /replace="Lys"
      /replace="Gln"
      /replace="Ala"
      /replace="Val"
      /replace="Leu"
      /replace="Tyr"
<220> FEATURE:
```

```
<221> NAME/KEY: VARIANT
<222> LOCATION: (6)..(6)
<223> OTHER INFORMATION: /replace="Ser"
       /replace="Thr"
<220> FEATURE:
<221> NAME/KEY: VARIANT
<222> LOCATION: (7)..(7)
<223> OTHER INFORMATION: /replace="Arg"
       /replace="Pro"
<220> FEATURE:
<221> NAME/KEY: VARIANT
<222> LOCATION: (10)..(10)
<223> OTHER INFORMATION: /replace="Tyr"
       /replace="Ile"
       /replace="Leu"
       /replace="Trp"
       /replace="Ser"
       /replace="Thr"
       /replace="Val"
       /replace="Leu"
       /replace="Phe"
<220> FEATURE:
<221> NAME/KEY: VARIANT
<222> LOCATION: (12)..(12)
<223> OTHER INFORMATION: /replace="His"
       /replace="Val"
       /replace="Ile"
       /replace="Leu"
       /replace="Ala"
<220> FEATURE:
<221> NAME/KEY: VARIANT
<222> LOCATION: (14)..(14)
<223> OTHER INFORMATION: /replace="Lys"
       /replace="Gln"
       /replace="Asn"
<220> FEATURE:
<221> NAME/KEY: VARIANT
<222> LOCATION: (15)..(15)
<223> OTHER INFORMATION: /replace="Asp"
       /replace="Ala"
       /replace="Arg"
       /replace="Glu"
       /replace="Val"
       /replace="Leu"
       /replace="Ile"

<400> SEQUENCE: 10

Ala Ser Cys Arg Thr Pro Lys Gln Cys Ala Arg Pro Cys Arg Lys Gln
1               5                   10                  15

Thr Gly Cys Pro Tyr Gly Lys Cys Met Asn Arg Lys Cys Lys Cys Asn
            20                  25                  30

Arg Cys

<210> SEQ ID NO 11
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
       /replace="Ile"
<220> FEATURE:
<221> NAME/KEY: VARIANT
<222> LOCATION: (2)..(2)
<223> OTHER INFORMATION: /replace="Arg"
       /replace="Lys"
<220> FEATURE:
<221> NAME/KEY: VARIANT
<222> LOCATION: (4)..(4)
<223> OTHER INFORMATION: /replace="Thr"
       /replace="Lys"
<220> FEATURE:
```

```
<221> NAME/KEY: VARIANT
<222> LOCATION: (5)..(5)
<223> OTHER INFORMATION: /replace="Gly"
      /replace="Ser"
      /replace="Asn"
      /replace="Ile"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (10)..(10)
<223> OTHER INFORMATION: /replace="Tyr"
      /replace="Ile"
      /replace="Leu"
      /replace="Trp"
<220> FEATURE:
<221> NAME/KEY: VARIANT
<222> LOCATION: (12)..(12)
<223> OTHER INFORMATION: /replace="His"
      /replace="Val"
      /replace="Ile"
      /replace="Leu"
      /replace="Ala"
<220> FEATURE:
<221> NAME/KEY: VARIANT
<222> LOCATION: (14)..(14)
<223> OTHER INFORMATION: /replace="Lys"
      /replace="Gln"
      /replace="Asn"
<220> FEATURE:
<221> NAME/KEY: VARIANT
<222> LOCATION: (15)..(15)
<223> OTHER INFORMATION: /replace="Asp"
      /replace="Ala"
      /replace="Arg"
      /replace="Glu"
      /replace="Val"
      /replace="Leu"
      /replace="Ile"

<400> SEQUENCE: 11

Ala Ser Cys Arg Thr Pro Lys Gln Cys Ala Arg Pro Cys Arg Lys Gln
1               5                   10                  15

Thr Gly Cys Pro Tyr Gly Lys Cys Met Asn Arg Lys Cys Lys Cys Asn
            20                  25                  30

Arg Cys

<210> SEQ ID NO 12
<211> LENGTH: 34
<212> TYPE: PRT
<213> ORGANISM: Artificial Sequence
<220> FEATURE:
<223> OTHER INFORMATION: peptide compound cgtx 539

<400> SEQUENCE: 12

Ala Ser Cys Arg Thr Pro Lys Gln Cys Ala Arg Pro Cys Arg Lys Gln
1               5                   10                  15

Thr Gly Cys Pro Tyr Gly Lys Cys Met Asn Arg Lys Cys Lys Cys Asn
            20                  25                  30

Arg Cys

<210> SEQ ID NO 13
<211> LENGTH: 34
<212> TYPE: PRT
```

```
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
      /replace="Ile"
      /replace="Leu"
<220> FEATURE:
<221> NAME/KEY: VARIANT
<222> LOCATION: (2)..(2)
<223> OTHER INFORMATION: /replace="Arg"
      /replace="Lys"
      /replace="Thr"
      /replace="Tyr"
<220> FEATURE:
<221> NAME/KEY: VARIANT
<222> LOCATION: (5)..(5)
<223> OTHER INFORMATION: /replace="Gly"
      /replace="Ser"
      /replace="Asn"
      /replace="Ile"
      /replace="Lys"
      /replace="Gln"
      /replace="Ala"
      /replace="Val"
      /replace="Leu"
      /replace="Tyr"
<220> FEATURE:
<221> NAME/KEY: VARIANT
<222> LOCATION: (6)..(6)
<223> OTHER INFORMATION: /replace="Ser"
      /replace="Thr"
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (14)..(14)
<223> OTHER INFORMATION: /replace="Arg"
      /replace="Gln"
      /replace="Asn"
<220> FEATURE:
<221> NAME/KEY: VARIANT
<222> LOCATION: (15)..(15)
<223> OTHER INFORMATION: /replace="Asp"
      /replace="Ala"
      /replace="Arg"
      /replace="Glu"
      /replace="Val"
      /replace="Leu"
      /replace="Ile"
<220> FEATURE:
<221> NAME/KEY: VARIANT
<222> LOCATION: (16)..(16)
<223> OTHER INFORMATION: /replace="Gln"
      /replace="Ala"
      /replace="Leu"
      /replace="Asp"
      /replace="Asn"
      /replace="Val"
      /replace="Ile"

<400> SEQUENCE: 13

Ala Ser Cys Arg Thr Pro Lys Gln Cys Tyr Pro His Cys Lys Lys Glu
1               5                   10                  15

Thr Gly Cys Pro Tyr Gly Lys Cys Met Asn Arg Lys Cys Lys Cys Asn
            20                  25                  30

Arg Cys

<210> SEQ ID NO 14
<211> LENGTH: 34
```

```
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
      /replace="Ile"
<220> FEATURE:
<221> NAME/KEY: VARIANT
<222> LOCATION: (2)..(2)
<223> OTHER INFORMATION: /replace="Arg"
      /replace="Lys"
<220> FEATURE:
<221> NAME/KEY: VARIANT
<222> LOCATION: (5)..(5)
<223> OTHER INFORMATION: /replace="Gly"
      /replace="Ser"
      /replace="Asn"
      /replace="Ile"
<220> FEATURE:
<221> NAME/KEY: VARIANT
<222> LOCATION: (6)..(6)
<223> OTHER INFORMATION: /replace="Ser"
      /replace="Thr"
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (14)..(14)
<223> OTHER INFORMATION: /replace="Arg"
      /replace="Gln"
<220> FEATURE:
<221> NAME/KEY: VARIANT
<222> LOCATION: (15)..(15)
<223> OTHER INFORMATION: /replace="Asp"
      /replace="Ala"
      /replace="Arg"
<220> FEATURE:
<221> NAME/KEY: VARIANT
<222> LOCATION: (16)..(16)
<223> OTHER INFORMATION: /replace="Gln"
      /replace="Ala"
      /replace="Leu"

<400> SEQUENCE: 14

Ala Ser Cys Arg Thr Pro Lys Gln Cys Tyr Pro His Cys Lys Lys Glu
1               5                   10                  15

Thr Gly Cys Pro Tyr Gly Lys Cys Met Asn Arg Lys Cys Lys Cys Asn
            20                  25                  30

Arg Cys

<210> SEQ ID NO 15
<211> LENGTH: 34
<212> TYPE: PRT
<213> ORGANISM: Artificial Sequence
<220> FEATURE:
<223> OTHER INFORMATION: peptide compound cgtx 540

<400> SEQUENCE: 15

Ala Ser Cys Arg Thr Pro Lys Gln Cys Tyr Pro His Cys Lys Lys Glu
1               5                   10                  15

Thr Gly Cys Pro Tyr Gly Lys Cys Met Asn Arg Lys Cys Lys Cys Asn
            20                  25                  30

Arg Cys

<210> SEQ ID NO 16
```

```
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
      /replace="Ile"
      /replace="Leu"
<220> FEATURE:
<221> NAME/KEY: VARIANT
<222> LOCATION: (2)..(2)
<223> OTHER INFORMATION: /replace="Ser"
      /replace="Lys"
      /replace="Thr"
      /replace="Tyr"
<220> FEATURE:
<221> NAME/KEY: VARIANT
<222> LOCATION: (4)..(4)
<223> OTHER INFORMATION: /replace="Thr"
      /replace="Lys"
      /replace="Ser"
      /replace="Tyr"
<220> FEATURE:
<221> NAME/KEY: VARIANT
<222> LOCATION: (5)..(5)
<223> OTHER INFORMATION: /replace="Gly"
      /replace="Ser"
      /replace="Asn"
      /replace="Ile"
      /replace="Lys"
      /replace="Gln"
      /replace="Ala"
      /replace="Val"
      /replace="Leu"
      /replace="Tyr"
<220> FEATURE:
<221> NAME/KEY: VARIANT
<222> LOCATION: (6)..(6)
<223> OTHER INFORMATION: /replace="Ser"
      /replace="Thr"
<220> FEATURE:
<221> NAME/KEY: VARIANT
<222> LOCATION: (7)..(7)
<223> OTHER INFORMATION: /replace="Lys"
      /replace="Pro"
<220> FEATURE:
<221> NAME/KEY: VARIANT
<222> LOCATION: (8)..(8)
<223> OTHER INFORMATION: /replace="Gln"
      /replace="Asn"
      /replace="Glu"
<220> FEATURE:
<221> NAME/KEY: VARIANT
<222> LOCATION: (10)..(10)
<223> OTHER INFORMATION: /replace="Tyr"
      /replace="Ile"
      /replace="Leu"
      /replace="Trp"
      /replace="Ser"
      /replace="Thr"
      /replace="Val"
      /replace="Leu"
      /replace="Phe"
<220> FEATURE:
<221> NAME/KEY: VARIANT
<222> LOCATION: (11)..(11)
<223> OTHER INFORMATION: /replace="Arg"
      /replace="Pro"
      /replace="Lys"
      /replace="Glu"
      /replace="Ser"
      /replace="Thr"
      /replace="Tyr"
<220> FEATURE:
<221> NAME/KEY: VARIANT
<222> LOCATION: (12)..(12)
```

```
<223> OTHER INFORMATION: /replace="His"
      /replace="Val"
      /replace="Ile"
      /replace="Leu"
      /replace="Ala"
<220> FEATURE:
<221> NAME/KEY: VARIANT
<222> LOCATION: (14)..(14)
<223> OTHER INFORMATION: /replace="Lys"
      /replace="Gln"
      /replace="Asn"
<220> FEATURE:
<221> NAME/KEY: VARIANT
<222> LOCATION: (15)..(15)
<223> OTHER INFORMATION: /replace="Asp"
      /replace="Ala"
      /replace="Arg"
      /replace="Glu"
      /replace="Val"
      /replace="Leu"
      /replace="Ile"
<220> FEATURE:
<221> NAME/KEY: VARIANT
<222> LOCATION: (16)..(16)
<223> OTHER INFORMATION: /replace="Gln"
      /replace="Ala"
      /replace="Leu"
      /replace="Asp"
      /replace="Asn"
      /replace="Val"
      /replace="Ile"
<220> FEATURE:
<221> NAME/KEY: VARIANT
<222> LOCATION: (32)..(32)
<223> OTHER INFORMATION: /replace="Tyr"
      /replace="Gln"
      /replace="Thr"
      /replace="Ser"
<220> FEATURE:
<221> NAME/KEY: VARIANT
<222> LOCATION: (33)..(33)
<223> OTHER INFORMATION: /replace="Gly"
      /replace="Lys"

<400> SEQUENCE: 16

Ala Arg Cys Arg Thr Pro Arg Asp Cys Ala Asp Pro Cys Arg Lys Glu
1               5                   10                  15

Thr Gly Cys Pro Tyr Gly Lys Cys Met Asn Arg Lys Cys Arg Cys Asn
            20                  25                  30

Arg Cys

<210> SEQ ID NO 17
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Val"
      /replace="Ile"
<220> FEATURE:
<221> NAME/KEY: VARIANT
<222> LOCATION: (2)..(2)
<223> OTHER INFORMATION: /replace="Ser"
      /replace="Lys"
<220> FEATURE:
<221> NAME/KEY: VARIANT
<222> LOCATION: (4)..(4)
<223> OTHER INFORMATION: /replace="Thr"
      /replace="Lys"
<220> FEATURE:
<221> NAME/KEY: VARIANT
<222> LOCATION: (5)..(5)
```

```
<223> OTHER INFORMATION: /replace="Gly"
      /replace="Ser"
      /replace="Asn"
      /replace="Ile"
<220> FEATURE:
<221> NAME/KEY: VARIANT
<222> LOCATION: (6)..(6)
<223> OTHER INFORMATION: /replace="Ser"
      /replace="Thr"
<220> FEATURE:
<221> NAME/KEY: VARIANT
<222> LOCATION: (7)..(7)
<223> OTHER INFORMATION: /replace="Lys"
      /replace="Pro"
<220> FEATURE:
<221> NAME/KEY: VARIANT
<222> LOCATION: (8)..(8)
<223> OTHER INFORMATION: /replace="Gln"
      /replace="Asn"
      /replace="Glu"
<220> FEATURE:
<221> NAME/KEY: VARIANT
<222> LOCATION: (10)..(10)
<223> OTHER INFORMATION: /replace="Tyr"
      /replace="Ile"
      /replace="Leu"
      /replace="Trp"
<220> FEATURE:
<221> NAME/KEY: VARIANT
<222> LOCATION: (11)..(11)
<223> OTHER INFORMATION: /replace="Arg"
      /replace="Pro"
      /replace="Lys"
      /replace="Glu"
      /replace="Ser"
<220> FEATURE:
<221> NAME/KEY: VARIANT
<222> LOCATION: (12)..(12)
<223> OTHER INFORMATION: /replace="His"
      /replace="Val"
<220> FEATURE:
<221> NAME/KEY: VARIANT
<222> LOCATION: (14)..(14)
<223> OTHER INFORMATION: /replace="Lys"
      /replace="Gln"
<220> FEATURE:
<221> NAME/KEY: VARIANT
<222> LOCATION: (15)..(15)
<223> OTHER INFORMATION: /replace="Asp"
      /replace="Ala"
      /replace="Arg"
<220> FEATURE:
<221> NAME/KEY: VARIANT
<222> LOCATION: (16)..(16)
<223> OTHER INFORMATION: /replace="Gln"
      /replace="Ala"
      /replace="Leu"
<220> FEATURE:
<221> NAME/KEY: VARIANT
<222> LOCATION: (32)..(32)
<223> OTHER INFORMATION: /replace="Tyr"
<220> FEATURE:
<221> NAME/KEY: VARIANT
<222> LOCATION: (33)..(33)
<223> OTHER INFORMATION: /replace="Gly"

<400> SEQUENCE: 17

Ala Arg Cys Arg Thr Pro Arg Asp Cys Ala Asp Pro Cys Arg Lys Glu
1               5                   10                  15

Thr Gly Cys Pro Tyr Gly Lys Cys Met Asn Arg Lys Cys Arg Cys Asn
            20                  25                  30

Arg Cys

<210> SEQ ID NO 18
<211> LENGTH: 34
```

```
<212> TYPE: PRT
<213> ORGANISM: Artificial Sequence
<220> FEATURE:
<223> OTHER INFORMATION: peptide compound cgtx 541

<400> SEQUENCE: 18

Ala Arg Cys Arg Thr Pro Arg Asp Cys Ala Asp Pro Cys Arg Lys Glu
1               5                  10                  15

Thr Gly Cys Pro Tyr Gly Lys Cys Met Asn Arg Lys Cys Arg Cys Asn
            20                  25                  30

Arg Cys

<210> SEQ ID NO 19
<211> LENGTH: 34
<212> TYPE: PRT
<213> ORGANISM: Artificial Sequence
<220> FEATURE:
<223> OTHER INFORMATION: peptide compound cgtx 542

<400> SEQUENCE: 19

Ala Arg Cys Arg Thr Ser Arg Asn Cys Ala Lys Pro Cys Arg Lys Gln
1               5                  10                  15

Thr Gly Cys Pro Tyr Gly Lys Cys Met Asn Arg Lys Cys Arg Cys Asn
            20                  25                  30

Arg Cys

<210> SEQ ID NO 20
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (4)..(4)
<223> OTHER INFORMATION: /replace="Arg"
      /replace="Lys"
      /replace="Ser"
      /replace="Tyr"
<220> FEATURE:
<221> NAME/KEY: VARIANT
<222> LOCATION: (5)..(5)
<223> OTHER INFORMATION: /replace="Thr"
      /replace="Gly"
      /replace="Ser"
      /replace="Ile"
      /replace="Lys"
      /replace="Gln"
      /replace="Ala"
      /replace="Val"
      /replace="Leu"
      /replace="Tyr"
<220> FEATURE:
<221> NAME/KEY: VARIANT
<222> LOCATION: (6)..(6)
<223> OTHER INFORMATION: /replace="Ser"
      /replace="Thr"
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (8)..(8)
<223> OTHER INFORMATION: /replace="Asp"
      /replace="Asn"
      /replace="Glu"
<220> FEATURE:
<221> NAME/KEY: VARIANT
<222> LOCATION: (10)..(10)
```

```
<223> OTHER INFORMATION: /replace="Ala"
      /replace="Ile"
      /replace="Leu"
      /replace="Trp"
      /replace="Ser"
      /replace="Thr"
      /replace="Val"
      /replace="Leu"
      /replace="Phe"
<220> FEATURE:
<221> NAME/KEY: VARIANT
<222> LOCATION: (11)..(11)
<223> OTHER INFORMATION: /replace="Asp"
      /replace="Arg"
      /replace="Lys"
      /replace="Glu"
      /replace="Ser"
      /replace="Thr"
      /replace="Tyr"
<220> FEATURE:
<221> NAME/KEY: VARIANT
<222> LOCATION: (12)..(12)
<223> OTHER INFORMATION: /replace="Pro"
      /replace="Val"
      /replace="Ile"
      /replace="Leu"
      /replace="Ala"
<220> FEATURE:
<221> NAME/KEY: VARIANT
<222> LOCATION: (14)..(14)
<223> OTHER INFORMATION: /replace="Arg"
      /replace="Gln"
      /replace="Asn"
<220> FEATURE:
<221> NAME/KEY: VARIANT
<222> LOCATION: (15)..(15)
<223> OTHER INFORMATION: /replace="Asp"
      /replace="Ala"
      /replace="Arg"
      /replace="Glu"
      /replace="Val"
      /replace="Leu"
      /replace="Ile"
<220> FEATURE:
<221> NAME/KEY: VARIANT
<222> LOCATION: (16)..(16)
<223> OTHER INFORMATION: /replace="Gln"
      /replace="Ala"
      /replace="Leu"
      /replace="Asp"
      /replace="Asn"
      /replace="Val"
      /replace="Ile"

<400> SEQUENCE: 20

Ile Ser Cys Thr Asn Pro Lys Gln Cys Tyr Pro His Cys Lys Lys Glu
1               5                   10                  15

Thr Gly Cys Pro Tyr Gly Lys Cys Met Asn Arg Lys Cys Lys Cys Asn
            20                  25                  30

Arg Cys

<210> SEQ ID NO 21
<211> LENGTH: 34
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (4)..(4)
<223> OTHER INFORMATION: /replace="Arg"
      /replace="Lys"
<220> FEATURE:
<221> NAME/KEY: VARIANT
<222> LOCATION: (5)..(5)
```

```
<223> OTHER INFORMATION: /replace="Thr"
      /replace="Gly"
      /replace="Ser"
      /replace="Ile"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Arg"
      /replace="Pro"
<220> FEATURE:
<221> NAME/KEY: VARIANT
<222> LOCATION: (8)..(8)
<223> OTHER INFORMATION: /replace="Asp"
      /replace="Asn"
      /replace="Glu"
<220> FEATURE:
<221> NAME/KEY: VARIANT
<222> LOCATION: (10)..(10)
<223> OTHER INFORMATION: /replace="Ala"
      /replace="Ile"
      /replace="Leu"
      /replace="Trp"
<220> FEATURE:
<221> NAME/KEY: VARIANT
<222> LOCATION: (11)..(11)
<223> OTHER INFORMATION: /replace="Asp"
      /replace="Arg"
      /replace="Lys"
      /replace="Glu"
      /replace="Ser"
<220> FEATURE:
<221> NAME/KEY: VARIANT
<222> LOCATION: (12)..(12)
<223> OTHER INFORMATION: /replace="Pro"
      /replace="Val"
<220> FEATURE:
<221> NAME/KEY: VARIANT
<222> LOCATION: (14)..(14)
<223> OTHER INFORMATION: /replace="Arg"
      /replace="Gln"
<220> FEATURE:
<221> NAME/KEY: VARIANT
<222> LOCATION: (15)..(15)
<223> OTHER INFORMATION: /replace="Asp"
      /replace="Ala"
      /replace="Arg"
<220> FEATURE:
<221> NAME/KEY: VARIANT
<222> LOCATION: (16)..(16)
<223> OTHER INFORMATION: /replace="Gln"
      /replace="Ala"
      /replace="Leu"

<400> SEQUENCE: 21

Ile Ser Cys Thr Asn Pro Lys Gln Cys Tyr Pro His Cys Lys Lys Glu
1               5                   10                  15

Thr Gly Cys Pro Tyr Gly Lys Cys Met Asn Arg Lys Cys Lys Cys Asn
            20                  25                  30

Arg Cys

<210> SEQ ID NO 22
<211> LENGTH: 34
<212> TYPE: PRT
<213> ORGANISM: Artificial Sequence
<220> FEATURE:
<223> OTHER INFORMATION: peptide compound cgtx 545

<400> SEQUENCE: 22

Ile Ser Cys Thr Asn Pro Lys Gln Cys Tyr Pro His Cys Lys Lys Glu
1               5                   10                  15
```

```
    Thr Gly Cys Pro Tyr Gly Lys Cys Met Asn Arg Lys Cys Lys Cys Asn
                 20                  25                  30

Arg Cys

<210> SEQ ID NO 23
<211> LENGTH: 38
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Gln"
      /replace="Ser"
      /replace="Tyr"
      /replace="Asn"
<220> FEATURE:
<221> NAME/KEY: VARIANT
<222> LOCATION: (2)..(2)
<223> OTHER INFORMATION: /replace="Phe"
      /replace="Val"
      /replace="Ala"
      /replace="Leu"
      /replace="Trp"
<220> FEATURE:
<221> NAME/KEY: VARIANT
<222> LOCATION: (3)..(3)
<223> OTHER INFORMATION: /replace="Thr"
      /replace="Tyr"
      /replace="Ser"
      /replace="Val"
      /replace="Ala"
      /replace="Leu"
<220> FEATURE:
<221> NAME/KEY: VARIANT
<222> LOCATION: (6)..(6)
<223> OTHER INFORMATION: /replace="Ser"
      /replace="Thr"
      /replace="Tyr"
      /replace="Arg"
<220> FEATURE:
<221> NAME/KEY: VARIANT
<222> LOCATION: (8)..(8)
<223> OTHER INFORMATION: /replace="Arg"
      /replace="Lys"
      /replace="Ser"
      /replace="Tyr"
<220> FEATURE:
<221> NAME/KEY: VARIANT
<222> LOCATION: (9)..(9)
<223> OTHER INFORMATION: /replace="Thr"
      /replace="Gly"
      /replace="Asn"
      /replace="Ile"
      /replace="Lys"
      /replace="Gln"
      /replace="Ala"
      /replace="Val"
      /replace="Leu"
      /replace="Tyr"
<220> FEATURE:
<221> NAME/KEY: VARIANT
<222> LOCATION: (10)..(10)
<223> OTHER INFORMATION: /replace="Ser"
      /replace="Thr"
<220> FEATURE:
<221> NAME/KEY: VARIANT
<222> LOCATION: (11)..(11)
<223> OTHER INFORMATION: /replace="Arg"
      /replace="Pro"
<220> FEATURE:
<221> NAME/KEY: VARIANT
<222> LOCATION: (12)..(12)
<223> OTHER INFORMATION: /replace="Asp"
      /replace="Asn"
```

```
        /replace="Glu"
<220> FEATURE:
<221> NAME/KEY: VARIANT
<222> LOCATION: (14)..(14)
<223> OTHER INFORMATION: /replace="Ala"
        /replace="Tyr"
        /replace="Ile"
        /replace="Trp"
        /replace="Ser"
        /replace="Thr"
        /replace="Val"
        /replace="Leu"
        /replace="Phe"
<220> FEATURE:
<221> NAME/KEY: VARIANT
<222> LOCATION: (15)..(15)
<223> OTHER INFORMATION: /replace="Asp"
        /replace="Arg"
        /replace="Lys"
        /replace="Glu"
        /replace="Ser"
        /replace="Thr"
        /replace="Tyr"
<220> FEATURE:
<221> NAME/KEY: VARIANT
<222> LOCATION: (16)..(16)
<223> OTHER INFORMATION: /replace="His"
        /replace="Val"
        /replace="Ile"
        /replace="Leu"
        /replace="Ala"
<220> FEATURE:
<221> NAME/KEY: VARIANT
<222> LOCATION: (18)..(18)
<223> OTHER INFORMATION: /replace="Arg"
        /replace="Gln"
        /replace="Asn"
<220> FEATURE:
<221> NAME/KEY: VARIANT
<222> LOCATION: (19)..(19)
<223> OTHER INFORMATION: /replace="Lys"
        /replace="Asp"
        /replace="Arg"
        /replace="Glu"
        /replace="Val"
        /replace="Leu"
        /replace="Ile"
<220> FEATURE:
<221> NAME/KEY: VARIANT
<222> LOCATION: (20)..(20)
<223> OTHER INFORMATION: /replace="Glu"
        /replace="Ala"
        /replace="Leu"
        /replace="Asp"
        /replace="Asn"
        /replace="Val"
        /replace="Ile"
<220> FEATURE:
<221> NAME/KEY: VARIANT
<222> LOCATION: (25)..(25)
<223> OTHER INFORMATION: /replace="Asn"
        /replace="Ser"
        /replace="Thr"
        /replace="Gln"
<220> FEATURE:
<221> NAME/KEY: VARIANT
<222> LOCATION: (26)..(26)
<223> OTHER INFORMATION: /replace="Ala"
        /replace="Val"
        /replace="Ile"
        /replace="Leu"
<220> FEATURE:
<221> NAME/KEY: VARIANT
<222> LOCATION: (34)..(34)
<223> OTHER INFORMATION: /replace="Arg"
<220> FEATURE:
<221> NAME/KEY: VARIANT
<222> LOCATION: (36)..(36)
<223> OTHER INFORMATION: /replace="Tyr"
```

```
        /replace="Gln"
        /replace="Thr"
        /replace="Ser"
<220> FEATURE:
<221> NAME/KEY: VARIANT
<222> LOCATION: (37)..(37)
<223> OTHER INFORMATION: /replace="Gly"
        /replace="Lys"

<400> SEQUENCE: 23

Thr Ile Ile Asn Val Lys Cys Thr Ser Pro Lys Gln Cys Leu Pro Pro
1               5                   10                  15

Cys Lys Ala Gln Thr Gly Cys Pro Tyr Gly Lys Cys Met Asn Arg Lys
            20                  25                  30

Cys Lys Cys Asn Arg Cys
        35

<210> SEQ ID NO 24
<211> LENGTH: 38
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (1)..(1)
<223> OTHER INFORMATION: /replace="Gln"
<220> FEATURE:
<221> NAME/KEY: VARIANT
<222> LOCATION: (2)..(2)
<223> OTHER INFORMATION: /replace="Phe"
<220> FEATURE:
<221> NAME/KEY: VARIANT
<222> LOCATION: (3)..(3)
<223> OTHER INFORMATION: /replace="Thr"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (8)..(8)
<223> OTHER INFORMATION: /replace="Arg"
        /replace="Lys"
<220> FEATURE:
<221> NAME/KEY: VARIANT
<222> LOCATION: (9)..(9)
<223> OTHER INFORMATION: /replace="Thr"
        /replace="Gly"
        /replace="Asn"
        /replace="Ile"
<220> FEATURE:
<221> NAME/KEY: VARIANT
<222> LOCATION: (10)..(10)
<223> OTHER INFORMATION: /replace="Ser"
<220> FEATURE:
<221> NAME/KEY: VARIANT
<222> LOCATION: (11)..(11)
<223> OTHER INFORMATION: /replace="Arg"
        /replace="Pro"
<220> FEATURE:
<221> NAME/KEY: VARIANT
<222> LOCATION: (12)..(12)
<223> OTHER INFORMATION: /replace="Asp"
        /replace="Asn"
        /replace="Glu"
<220> FEATURE:
<221> NAME/KEY: VARIANT
<222> LOCATION: (14)..(14)
<223> OTHER INFORMATION: /replace="Ala"
        /replace="Tyr"
        /replace="Ile"
        /replace="Trp"
<220> FEATURE:
<221> NAME/KEY: VARIANT
```

```
<222> LOCATION: (15)..(15)
<223> OTHER INFORMATION: /replace="Asp"
      /replace="Arg"
      /replace="Lys"
      /replace="Glu"
      /replace="Ser"
<220> FEATURE:
<221> NAME/KEY: VARIANT
<222> LOCATION: (16)..(16)
<223> OTHER INFORMATION: /replace="His"
      /replace="Val"
<220> FEATURE:
<221> NAME/KEY: VARIANT
<222> LOCATION: (18)..(18)
<223> OTHER INFORMATION: /replace="Arg"
      /replace="Gln"
<220> FEATURE:
<221> NAME/KEY: VARIANT
<222> LOCATION: (19)..(19)
<223> OTHER INFORMATION: /replace="Lys"
      /replace="Asp"
      /replace="Arg"
<220> FEATURE:
<221> NAME/KEY: VARIANT
<222> LOCATION: (20)..(20)
<223> OTHER INFORMATION: /replace="Glu"
      /replace="Ala"
      /replace="Leu"
<220> FEATURE:
<221> NAME/KEY: VARIANT
<222> LOCATION: (25)..(25)
<223> OTHER INFORMATION: /replace="Asn"
<220> FEATURE:
<221> NAME/KEY: VARIANT
<222> LOCATION: (26)..(26)
<223> OTHER INFORMATION: /replace="Ala"
<220> FEATURE:
<221> NAME/KEY: VARIANT
<222> LOCATION: (34)..(34)
<223> OTHER INFORMATION: /replace="Arg"
<220> FEATURE:
<221> NAME/KEY: VARIANT
<222> LOCATION: (36)..(36)
<223> OTHER INFORMATION: /replace="Tyr"
<220> FEATURE:
<221> NAME/KEY: VARIANT
<222> LOCATION: (37)..(37)
<223> OTHER INFORMATION: /replace="Gly"

<400> SEQUENCE: 24

Thr Ile Ile Asn Val Lys Cys Thr Ser Pro Lys Gln Cys Leu Pro Pro
1               5                   10                  15

Cys Lys Ala Gln Thr Gly Cys Pro Tyr Gly Lys Cys Met Asn Arg Lys
                20                  25                  30

Cys Lys Cys Asn Arg Cys
            35

<210> SEQ ID NO 25
<211> LENGTH: 38
<212> TYPE: PRT
<213> ORGANISM: Artificial Sequence
<220> FEATURE:
<223> OTHER INFORMATION: peptide compound cgtx 544

<400> SEQUENCE: 25

Thr Ile Ile Asn Val Lys Cys Thr Ser Pro Lys Gln Cys Leu Pro Pro
1               5                   10                  15

Cys Lys Ala Gln Thr Gly Cys Pro Tyr Gly Lys Cys Met Asn Arg Lys
                20                  25                  30

Cys Lys Cys Asn Arg Cys
            35
```

```
<210> SEQ ID NO 26
<211> LENGTH: 38
<212> TYPE: PRT
<213> ORGANISM: Artificial Sequence
<220> FEATURE:
<223> OTHER INFORMATION: peptide compound cgtx 547

<400> SEQUENCE: 26

Gln Phe Thr Asn Val Ser Cys Thr Thr Ser Lys Glu Cys Trp Ser Val
1               5                   10                  15

Cys Gln Arg Leu Thr Gly Cys Pro Tyr Gly Lys Cys Met Asn Arg Lys
            20                  25                  30

Cys Lys Cys Asn Arg Cys
        35

<210> SEQ ID NO 27
<211> LENGTH: 39
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (3)..(3)
<223> OTHER INFORMATION: /replace="Ile"
      /replace="Phe"
      /replace="Val"
      /replace="Ala"
      /replace="Leu"
      /replace="Trp"
<220> FEATURE:
<221> NAME/KEY: VARIANT
<222> LOCATION: (7)..(7)
<223> OTHER INFORMATION: /replace="Lys"
      /replace="Thr"
      /replace="Tyr"
      /replace="Arg"
<220> FEATURE:
<221> NAME/KEY: VARIANT
<222> LOCATION: (9)..(9)
<223> OTHER INFORMATION: /replace="Arg"
      /replace="Lys"
      /replace="Ser"
      /replace="Tyr"
<220> FEATURE:
<221> NAME/KEY: VARIANT
<222> LOCATION: (10)..(10)
<223> OTHER INFORMATION: /replace="Thr"
      /replace="Ser"
      /replace="Asn"
      /replace="Ile"
      /replace="Lys"
      /replace="Gln"
      /replace="Ala"
      /replace="Val"
      /replace="Leu"
      /replace="Tyr"
<220> FEATURE:
<221> NAME/KEY: VARIANT
<222> LOCATION: (11)..(11)
<223> OTHER INFORMATION: /replace="Pro"
      /replace="Thr"
<220> FEATURE:
<221> NAME/KEY: VARIANT
<222> LOCATION: (12)..(12)
<223> OTHER INFORMATION: /replace="Arg"
      /replace="Lys"
<220> FEATURE:
<221> NAME/KEY: VARIANT
<222> LOCATION: (13)..(13)
<223> OTHER INFORMATION: /replace="Asp"
      /replace="Asn"
      /replace="Glu"
<220> FEATURE:
```

```
<221> NAME/KEY: VARIANT
<222> LOCATION: (15)..(15)
<223> OTHER INFORMATION: /replace="Ala"
      /replace="Tyr"
      /replace="Leu"
      /replace="Trp"
      /replace="Ser"
      /replace="Thr"
      /replace="Val"
      /replace="Leu"
      /replace="Phe"
<220> FEATURE:
<221> NAME/KEY: VARIANT
<222> LOCATION: (16)..(16)
<223> OTHER INFORMATION: /replace="Asp"
      /replace="Arg"
      /replace="Pro"
      /replace="Glu"
      /replace="Ser"
      /replace="Thr"
      /replace="Tyr"
<220> FEATURE:
<221> NAME/KEY: VARIANT
<222> LOCATION: (17)..(17)
<223> OTHER INFORMATION: /replace="His"
      /replace="Val"
      /replace="Ile"
      /replace="Leu"
      /replace="Ala"
<220> FEATURE:
<221> NAME/KEY: VARIANT
<222> LOCATION: (19)..(19)
<223> OTHER INFORMATION: /replace="Arg"
      /replace="Gln"
      /replace="Asn"
<220> FEATURE:
<221> NAME/KEY: VARIANT
<222> LOCATION: (20)..(20)
<223> OTHER INFORMATION: /replace="Lys"
      /replace="Ala"
      /replace="Arg"
      /replace="Glu"
      /replace="Val"
      /replace="Leu"
      /replace="Ile"
<220> FEATURE:
<221> NAME/KEY: VARIANT
<222> LOCATION: (21)..(21)
<223> OTHER INFORMATION: /replace="Glu"
      /replace="Gln"
      /replace="Leu"
      /replace="Asp"
      /replace="Asn"
      /replace="Val"
      /replace="Ile"
<220> FEATURE:
<221> NAME/KEY: VARIANT
<222> LOCATION: (26)..(26)
<223> OTHER INFORMATION: /replace="Asn"
      /replace="Ser"
      /replace="Thr"
      /replace="Gln"
<220> FEATURE:
<221> NAME/KEY: VARIANT
<222> LOCATION: (27)..(27)
<223> OTHER INFORMATION: /replace="Ala"
      /replace="Val"
      /replace="Ile"
      /replace="Leu"
<220> FEATURE:
<221> NAME/KEY: VARIANT
<222> LOCATION: (35)..(35)
<223> OTHER INFORMATION: /replace="Arg"
<220> FEATURE:
<221> NAME/KEY: VARIANT
<222> LOCATION: (37)..(37)
<223> OTHER INFORMATION: /replace="Tyr"
      /replace="Gln"
      /replace="Thr"
```

```
        /replace="Ser"
<220> FEATURE:
<221> NAME/KEY: VARIANT
<222> LOCATION: (38)..(38)
<223> OTHER INFORMATION: /replace="Gly"
        /replace="Lys"

<400> SEQUENCE: 27

Gly Val Pro Ile Asn Val Ser Cys Thr Gly Ser Pro Gln Cys Ile Lys
1               5                   10                  15

Pro Cys Lys Asp Ala Thr Gly Cys Pro Tyr Gly Lys Cys Met Asn Arg
            20                  25                  30

Lys Cys Lys Cys Asn Arg Cys
        35

<210> SEQ ID NO 28
<211> LENGTH: 39
<212> TYPE: PRT
<213> ORGANISM: Artificial Sequence
<220> FEATURE:
<223> OTHER INFORMATION: peptide compound
<220> FEATURE:
<221> NAME/KEY: VARIANT
<222> LOCATION: (3)..(3)
<223> OTHER INFORMATION: /replace="Ile"
        /replace="Phe"
<220> FEATURE:
<221> NAME/KEY: VARIANT
<222> LOCATION: (7)..(7)
<223> OTHER INFORMATION: /replace="Lys"
<220> FEATURE:
<221> NAME/KEY: VARIANT
<222> LOCATION: (9)..(9)
<223> OTHER INFORMATION: /replace="Arg"
        /replace="Lys"
<220> FEATURE:
<221> NAME/KEY: VARIANT
<222> LOCATION: (10)..(10)
<223> OTHER INFORMATION: /replace="Thr"
        /replace="Ser"
        /replace="Asn"
        /replace="Ile"
<220> FEATURE:
<221> NAME/KEY: VARIANT
<222> LOCATION: (11)..(11)
<223> OTHER INFORMATION: /replace="Pro"
<220> FEATURE:
<221> NAME/KEY: VARIANT
<222> LOCATION: (12)..(12)
<223> OTHER INFORMATION: /replace="Arg"
        /replace="Lys"
<220> FEATURE:
<221> NAME/KEY: VARIANT
<222> LOCATION: (13)..(13)
<223> OTHER INFORMATION: /replace="Asp"
        /replace="Asn"
        /replace="Glu"
<220> FEATURE:
<221> NAME/KEY: VARIANT
<222> LOCATION: (15)..(15)
<223> OTHER INFORMATION: /replace="Ala"
        /replace="Tyr"
        /replace="Leu"
        /replace="Trp"
<220> FEATURE:
<221> NAME/KEY: VARIANT
<222> LOCATION: (16)..(16)
<223> OTHER INFORMATION: /replace="Asp"
        /replace="Arg"
        /replace="Pro"
        /replace="Glu"
        /replace="Ser"
<220> FEATURE:
<221> NAME/KEY: VARIANT
<222> LOCATION: (17)..(17)
```

```
<223> OTHER INFORMATION: /replace="His"
      /replace="Val"
<220> FEATURE:
<221> NAME/KEY: VARIANT
<222> LOCATION: (19)..(19)
<223> OTHER INFORMATION: /replace="Arg"
      /replace="Gln"
<220> FEATURE:
<221> NAME/KEY: VARIANT
<222> LOCATION: (20)..(20)
<223> OTHER INFORMATION: /replace="Lys"
      /replace="Ala"
      /replace="Arg"
<220> FEATURE:
<221> NAME/KEY: VARIANT
<222> LOCATION: (21)..(21)
<223> OTHER INFORMATION: /replace="Glu"
      /replace="Gln"
      /replace="Leu"
<220> FEATURE:
<221> NAME/KEY: VARIANT
<222> LOCATION: (26)..(26)
<223> OTHER INFORMATION: /replace="Asn"
<220> FEATURE:
<221> NAME/KEY: VARIANT
<222> LOCATION: (27)..(27)
<223> OTHER INFORMATION: /replace="Ala"
<220> FEATURE:
<221> NAME/KEY: VARIANT
<222> LOCATION: (35)..(35)
<223> OTHER INFORMATION: /replace="Arg"
<220> FEATURE:
<221> NAME/KEY: VARIANT
<222> LOCATION: (37)..(37)
<223> OTHER INFORMATION: /replace="Tyr"
<220> FEATURE:
<221> NAME/KEY: VARIANT
<222> LOCATION: (38)..(38)
<223> OTHER INFORMATION: /replace="Gly"

<400> SEQUENCE: 28

Gly Val Pro Ile Asn Val Ser Cys Thr Gly Ser Pro Gln Cys Ile Lys
1               5                   10                  15

Pro Cys Lys Asp Ala Thr Gly Cys Pro Tyr Gly Lys Cys Met Asn Arg
            20                  25                  30

Lys Cys Lys Cys Asn Arg Cys
        35

<210> SEQ ID NO 29
<211> LENGTH: 39
<212> TYPE: PRT
<213> ORGANISM: Artificial Sequence
<220> FEATURE:
<223> OTHER INFORMATION: peptide compound cgtx 543

<400> SEQUENCE: 29

Gly Val Pro Ile Asn Val Ser Cys Thr Gly Ser Pro Gln Cys Ile Lys
1               5                   10                  15

Pro Cys Lys Asp Ala Thr Gly Cys Pro Tyr Gly Lys Cys Met Asn Arg
            20                  25                  30

Lys Cys Lys Cys Asn Arg Cys
        35

<210> SEQ ID NO 30
<211> LENGTH: 39
<212> TYPE: PRT
<213> ORGANISM: Artificial Sequence
<220> FEATURE:
<223> OTHER INFORMATION: peptide compound cgtx 546

<400> SEQUENCE: 30
```

```
Gly Val Ile Ile Asn Val Lys Cys Lys Ile Ser Arg Gln Cys Leu Glu
1               5                   10                  15

Pro Cys Lys Lys Ala Thr Gly Cys Pro Tyr Gly Lys Cys Met Asn Arg
            20                  25                  30

Lys Cys Lys Cys Asn Arg Cys
        35

<210> SEQ ID NO 31
<211> LENGTH: 39
<212> TYPE: PRT
<213> ORGANISM: Artificial Sequence
<220> FEATURE:
<223> OTHER INFORMATION: peptide compound cgtx 548

<400> SEQUENCE: 31

Gly Val Pro Ile Asn Val Lys Cys Thr Gly Ser Pro Gln Cys Leu Lys
1               5                   10                  15

Pro Cys Lys Asp Ala Thr Gly Cys Pro Tyr Gly Lys Cys Met Asn Arg
            20                  25                  30

Lys Cys Lys Cys Asn Arg Cys
        35

<210> SEQ ID NO 32
<211> LENGTH: 34
<212> TYPE: PRT
<213> ORGANISM: Heterometrus spinifer

<400> SEQUENCE: 32

Ala Ser Cys Arg Thr Pro Lys Asp Cys Ala Asp Pro Cys Arg Lys Glu
1               5                   10                  15

Thr Gly Cys Pro Tyr Gly Lys Cys Met Asn Arg Lys Cys Lys Cys Asn
            20                  25                  30

Arg Cys
```

KV1.3 POTASSIUM CHANNEL ANTAGONISTS

CROSS-REFERENCE TO RELATED PATENT APPLICATIONS

This application is a U.S. National Phase Application under 35 U.S.C. § 371 of International Patent Application No. PCT/EP2015/060073, filed May 7, 2015, and claims priority to Great Britain Application No. 1408135.0, filed May 8, 2014, each of which are incorporated by reference in their entireties. The International Application was published on Nov. 12, 2015, as International Publication No. WO/2015/169901 A1.

FIELD OF THE INVENTION

The present invention relates to compounds which are capable of selectively binding to and inhibiting the activity of the potassium channel Kv1.3. The invention also relates to pharmaceutical compositions comprising such compounds and to the use of said compounds and said pharmaceutical compositions for the treatment or prevention of autoimmune diseases, obesity, parodontitis and/or tissue transplant rejection.

BACKGROUND OF THE INVENTION

Autoimmune diseases are a group of more than 80 distinct diseases that emerge when a host's immune response fails to distinguish foreign antigens from self molecules (autoantigens), thereby eliciting an aberrant immune response. The causes of autoimmune diseases are still obscure, however they are thought to be caused by a combination of genetic and environmental factors.

Immuno-inflammatory disorders like multiple sclerosis, psoriasis and rheumatoid arthritis share a common pathogenic principle. Their pathogenesis is characterized by autoreactive memory T cells mediating chronic inflammatory processes upon stimulation. In particular, repeated antigenic challenge, usually occurring in autoimmune diseases, causes long-lived central memory cells ($T_{CM}$), which like naïve cells, home to lymph nodes to encounter their cognate antigen, to differentiate into short-lived effector memory cells ($T_{EM}$) that do not need to home to lymph nodes for antigen-induced activation. Activated $T_{EM}$ cells change into $T_{EM}$ effectors, which migrate rapidly to sites of inflammation where they produce large amounts of proinflammatory cytokines. CD8$^+$ $T_{EM}$ cells further produce high amounts of perform and are thus highly destructive.

The current treatments for autoimmune diseases include the systemic use of anti-inflammatory drugs and potent immunosuppressive and immunomodulatory agents. However, these drugs cause numerous adverse side effects including e.g. suppression of the immune system as a whole, with the risk of infection and neoplasia. Furthermore, in some patients said drugs are unable to induce clinically significant remissions.

The voltage-gated Kv1.3 K$^+$ channel is one of 76 potassium channels in the human genome and has been found to be present in human T lymphocytes. All human T cells express the Kv1.3 channel as well as the calcium-activated KCa3.1, which together provide the counter-balancing potassium efflux for the calcium influx that is necessary for T cell activation and proliferation. The number of channels expressed by a given cell depends on its state of activation and differentiation. Antigen or mitogen stimulated CD4$^+$ and CD8$^+$ $T_{EM}$ cells exhibit an approximately 4- to 5-fold increased expression of Kv1.3, while human naïve or $T_{CM}$ cells up-regulate the calcium-activated KCa3.1 channel to regulate membrane potential and Ca2$^+$ signaling in the activated state.

In view of this differential overexpression in $T_{EM}$ cells, the Kv1.3 channel constitutes a promising new $T_{EM}$-cell-specific therapeutic target for the treatment of autoimmune diseases, whose pathogenesis involves autoreactive $T_{EM}$ cells such as e.g. multiple sclerosis, rheumatoid arthritis, psoriasis and type-1 diabetes, but also for other chronic inflammatory diseases, such as e.g. parodontitits.

Furthermore, there is indication that Kv1.3 channels play a role in the regulation of body weight. The Kv1.3 channel thus also constitutes a promising target for the treatment of obesity.

Therefore, there is an ongoing need for Kv1.3 channel specific therapeutic compounds that exhibit a strong and specific interaction with the Kv1.3 channel and are capable of blocking or reducing its activity.

OBJECTIVE AND SUMMARY OF THE INVENTION

It is one objective of the present invention to provide compounds, which are capable of specifically binding to and inhibiting or reducing the activity of the potassium channel Kv1.3. It is a further objective of the present invention to provide such inhibitory compounds and pharmaceutical compositions comprising such inhibitory compounds for use in the treatment of autoimmune diseases, such as e.g. multiple sclerosis, rheumatoid arthritis, psoriasis and/or type-1 diabetes, obesity and/or parodontitis.

These and other objectives as they will become apparent from the ensuing description and claims are attained by the subject matter of the independent claims. Some of the preferred embodiments are defined by the dependent claims.

In a first aspect, the present invention relates to a compound comprising or consisting of an amino acid sequence:

(SEQ ID No.: 23)
$X_1$-$X_2$-$X_3$-N-V-$X_4$-C-$X_5$-$X_6$-$X_7$-$X_8$-$X_9$-C-$X_{10}$-$X_{11}$-$X_{12}$-C-$X_{13}$-

$X_{14}$-$X_{15}$-T-G-C-P-$X_{16}$-$X_{17}$-K-C-M-N-R-K-C-$X_{18}$-C-$X_{19}$-$X_{20}$-C, wherein $X_1$=T,Q,S,Y,N; $X_2$=I,F,V,A,L,W; $X_3$=I,T,Y,S,V,A,L; $X_4$=K,S,T,Y,R; $X_5$=R,T,K,S,Y; $X_6$=T,G,S,N,I,K,Q,A,V,L,Y; $X_7$=P,S,T; $X_8$=R,K,P; $X_9$=D,Q,N,E; $X_{10}$=A,Y,I,L,W,S,T,V,L,F; $X_{11}$=D,R,P,K,E,S,T,Y; $X_{12}$=P,H,V,I,L,A; $X_{13}$=R,K,Q,N; $X_{14}$=K,D,A,R,E,V,L,I; $X_{15}$=E,Q,A,L,D,N,V,I; $X_{16}$=Y,N,S,T,Q; $X_{17}$=A,G,V,I,L; $X_{18}$=K,R, $X_{19}$=Y,N,Q,T,S and $X_{20}$=G,R,K.

In a variation of the first aspect, the present invention relates to a compound comprising or consisting of an amino acid sequence:

(SEQ ID No.: 23)
$X_1$-$X_2$-$X_3$-N-V-$X_4$-C-$X_5$-$X_6$-$X_7$-$X_8$-$X_9$-C-$X_{10}$-$X_{11}$-$X_{12}$-C-$X_{13}$-

$X_{14}$-$X_{15}$-T-G-C-P-$X_{16}$-$X_{17}$-K-C-M-N-R-K-C-$X_{18}$-C-$X_{19}$-$X_{20}$-C, wherein $X_1$=T,Q,S,Y,N; $X_2$=I,F,V,A,L,W; $X_3$=I,T,Y,S,V,A,L; $X_4$=K,S,T,Y,R; $X_5$=R,T,K,S,Y; $X_6$=T,G,S,N,I,K,Q,A,V,L,Y; $X_7$=P,S,T; $X_8$=R,K,P; $X_9$=D,Q,N,E; $X_{10}$=A,Y,I,L,W,S,T,V,L,F; $X_{11}$=D,R,P,K,E,S,T,Y; $X_{12}$=P,H,V,I,L,A; $X_{13}$=R,K, Q,N; $X_{14}$=K,D,A,R,E,V,L,I; $X_{15}$=E,Q,A,L,D,N,V,I; $X_{16}$=Y, N,S,T,Q; $X_{17}$=A,G,V,I,L; $X_{18}$=K,R, $X_{19}$=Y,N,Q,T,S and $X_{20}$=G,R,K; and wherein the compound is capable of selectively binding to the potassium channel Kv1.3.

In a second aspect, the present invention relates to a compound comprising or consisting of an amino acid sequence:

(SEQ ID No: 1)
$X_1$-$X_2$-C-$X_3$-$X_4$-$X_5$-$X_6$-$X_7$-C-$X_8$-$X_9$-$X_{10}$-C-$X_{11}$-$X_{12}$-$X_{13}$-T-G-

C-P-$X_{14}$-$X_{15}$-K-C-M-N-R-K-C-$X_{16}$-C-$X_{17}$-$X_{18}$-C;

wherein $X_1$=A,V,I,L; $X_2$=S,R,K,T,Y; $X_3$=R,T,K,S,Y; $X_4$=T, G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V, I,L,A; $X_{11}$=R,K,Q,N; $X_{12}$=K,D,A,R,E,V,L,I; $X_{13}$=E,Q,A,L, D,N,V,I; $X_{14}$=Y,N,S,T,Q; $X_{15}$=A,G,V,I,L; $X_{16}$=K,R, $X_{17}$=Y, N,Q,T,S and $X_{18}$=G,R,K.

In a variation of the second aspect another aspect, the present invention relates to a compound comprising or consisting of an amino acid sequence according to SEQ ID No:1, wherein $X_1$=A,V,I,L; $X_2$=S,R,K,T,Y; $X_3$=R,T,K,S,Y; $X_4$=T, G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V, I,L,A; $X_{11}$=R,K,Q,N; $X_{12}$=K,D,A,R,E,V,L,I; $X_{13}$=E,Q,A,L, D,N,V,I; $X_{14}$=Y,N,S,T,Q; $X_{15}$=A,G,V,I,L; $X_{16}$=K,R, $X_{17}$=Y, N,Q,T,S and $X_{18}$=G,R,K; and wherein the compound is capable of selectively binding to the potassium channel Kv1.3.

In a third aspect, the present invention relates to a compound comprising or consisting of an amino acid sequence:

(SEQ ID No.: 27)
G-V-$X_1$-I-N-V-$X_2$-C-$X_3$-$X_4$-$X_5$-$X_6$-$X_7$-C-$X_8$-$X_9$-$X_{10}$-C-$X_{11}$-

$X_{12}$-$X_{13}$-T-G-C-P-$X_{14}$-$X_{15}$-K-C-M-N-R-K-C-$X_{16}$-C-$X_{17}$-

$X_{18}$-C;

wherein $X_1$=P,I,F,V,A,L,W; $X_2$=K,S,T,Y,R; $X_3$=R,T,K,S,Y; $X_4$=T,G,S,N,I,K,Q,A,V,L,Y; $X_5$=P,S,T; $X_6$=R,K,P; $X_7$=D,Q, N,E; $X_8$=A,Y,I,L,W,S,T,V,L,F; $X_9$=D,R,P,K,E,S,T,Y; $X_{10}$=P, H,V,I,L,A; $X_{11}$=R,K,Q,N; $X_{12}$=K,D,A,R,E,V,L,I; $X_{13}$=E,Q, A,L,D,N,V,I; $X_{14}$=Y,N,S,T,Q; $X_{15}$=A,G,V,I,L; $X_{16}$=K,R, $X_{17}$=Y,N,Q,T,S and $X_{18}$=G,R,K.

In a variation of the third aspect, the present invention relates to a compound comprising or consisting of an amino acid sequence according to SEQ ID No.:27, wherein $X_1$=P,I,F,V,A,L,W; $X_2$=K,S,T,Y,R; $X_3$=R,T,K,S,Y; $X_4$=T,G,S,N,I,K,Q,A,V,L,Y; $X_5$=P,S,T; $X_6$=R,K,P; $X_7$=D,Q, N,E; $X_8$=A,Y,I,L,W,S,T,V,L,F; $X_9$=D,R,P,K,E,S,T,Y; $X_{10}$=P, H,V,I,L,A; $X_{11}$=R,K,Q,N; $X_{12}$=K,D,A,R,E,V,L,I; $X_{13}$=E,Q, A,L,D,N,V,I; $X_{14}$=Y,N,S,T,Q; $X_{15}$=A,G,V,I,L; $X_{16}$=K,R, $X_{17}$=Y,N,Q,T,S and $X_{18}$=G,R,K; and wherein the compound is capable of selectively binding to the potassium channel Kv1.3.

In another aspect the present invention relates to a nucleic acid sequence encoding for an amino acid sequence according to the invention.

In yet another aspect the invention further provides a vector comprising a nucleic acid sequence according to the invention.

In still another aspect the present invention also provides a host cell comprising a nucleic acid sequence or a vector according to the invention.

In still another aspect the present invention relates to a pharmaceutical composition comprising a compound according to the invention.

The present invention in a further aspect also relates to a compound according to the invention or a pharmaceutical composition according to the invention for use in the treatment or prevention of an auto immune disease, obesity, parodontitis and/or tissue transplant rejection.

The present invention in another aspect also relates to the use of a compound according to the invention or a pharmaceutical composition according to the invention in the manufacture of a medicament for treating or preventing an auto immune disease, obesity, parodontitis and/or tissue transplant rejection.

In another aspect the present invention relates to a method of treating or preventing an auto immune disease, obesity, parodontitis and/or tissue transplant rejection in a mammal by administering a compound according to the invention or a pharmaceutical composition according to the invention to a mammal in need thereof.

The invention in a further aspect also provides a method of manufacturing a compound, a nucleic acid sequence, a vector or a pharmaceutical composition according to the invention.

BRIEF DESCRIPTION OF THE FIGURES

Figure 1A:
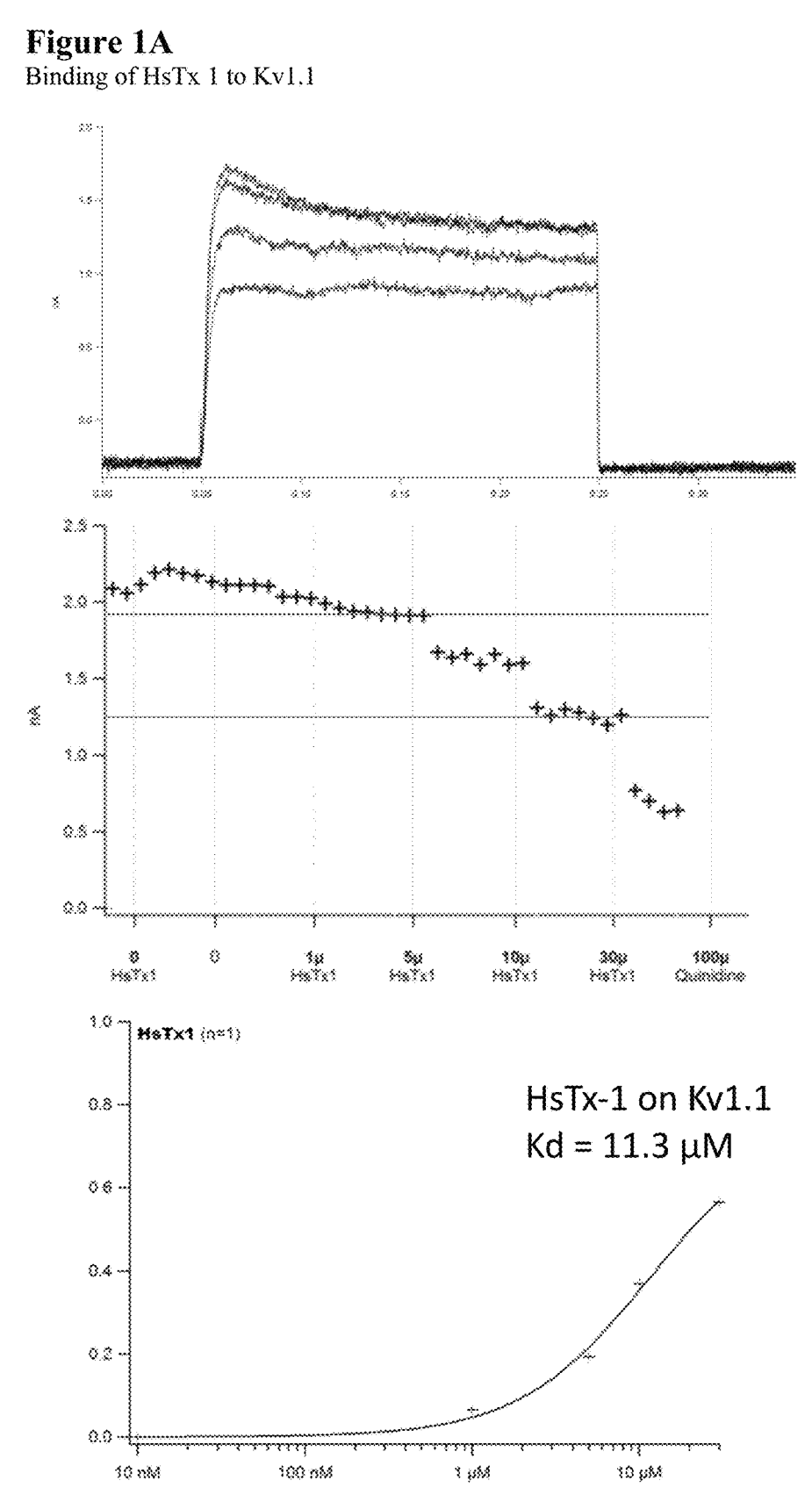
Figure 1B:
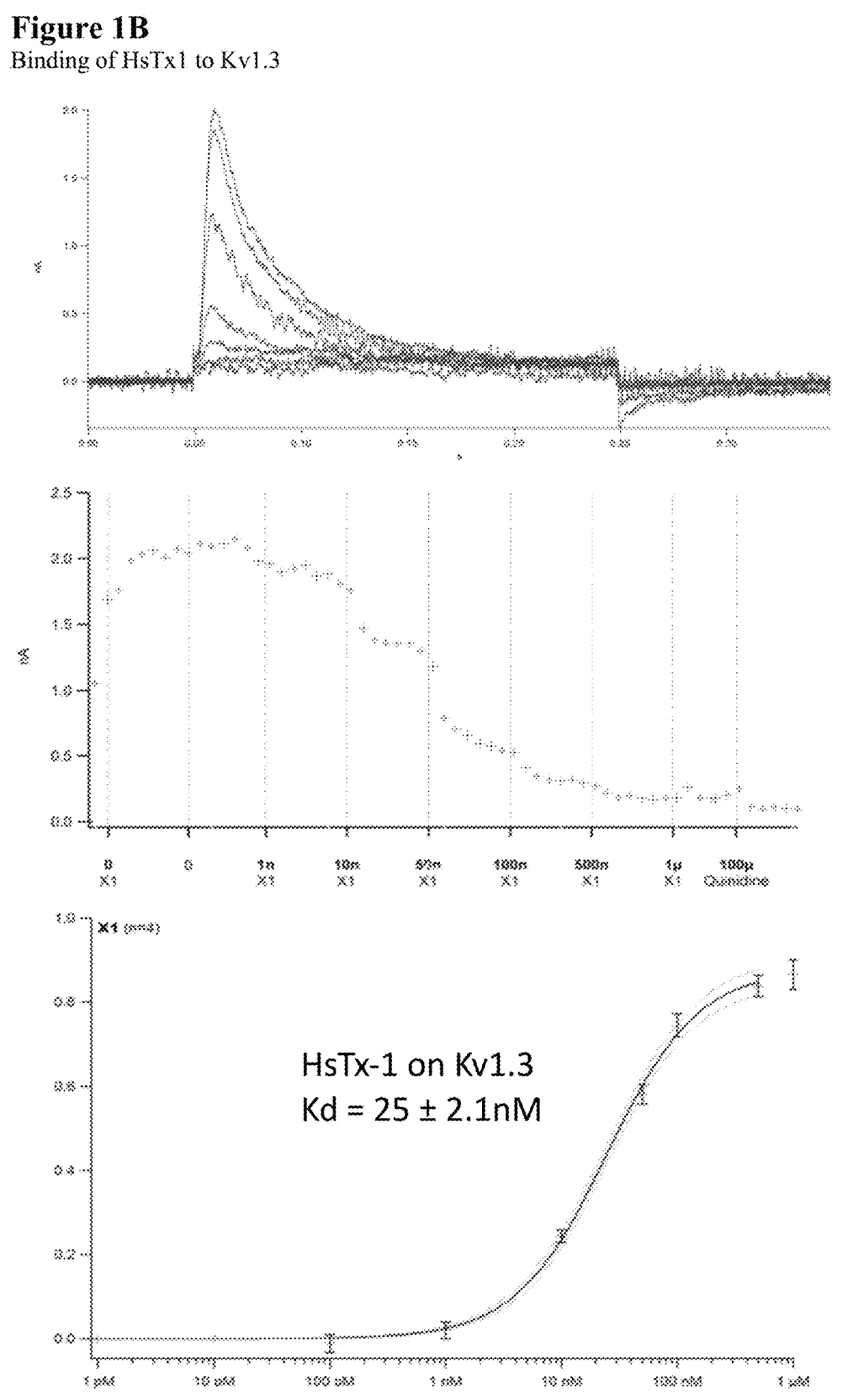

FIGS. 1A-1F Measurement of Kv1.3 (FIGS. 1B and 1E), Kv1.5 (FIGS. 1C and 1F) and Kv1.1 (FIGS. 1A and 1D) channel inhibition by patch-clamp.

FIG. 2 Sequence listing cgtx 538-548.

Figure 1C:
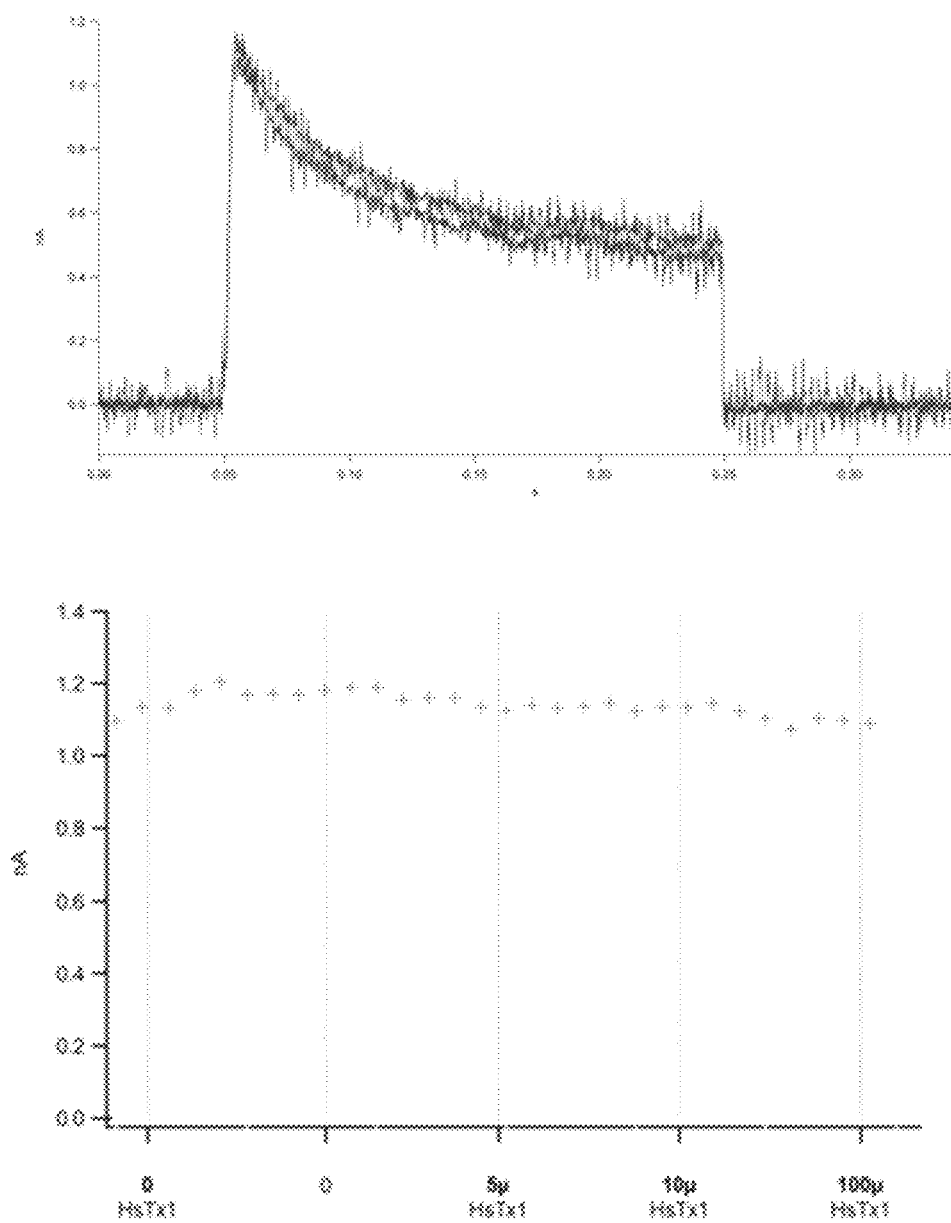
Figure 1D:
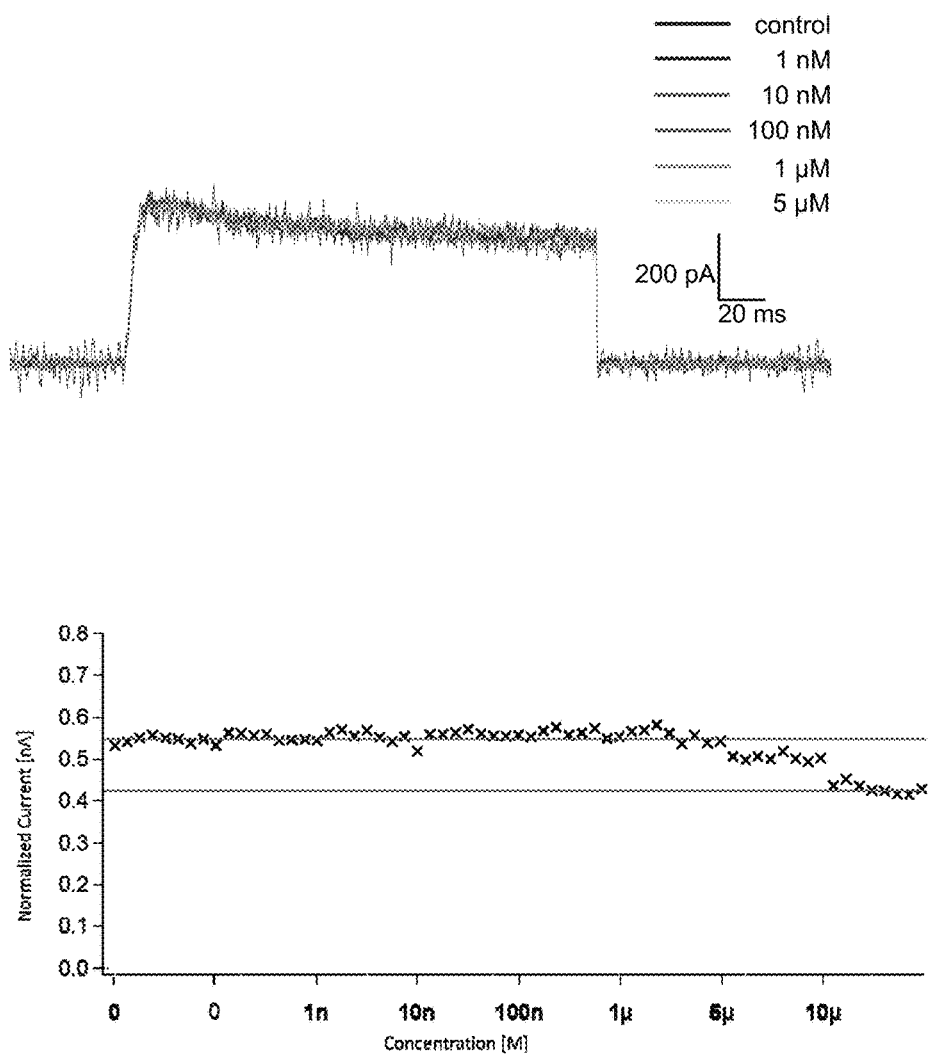
Figure 1E:
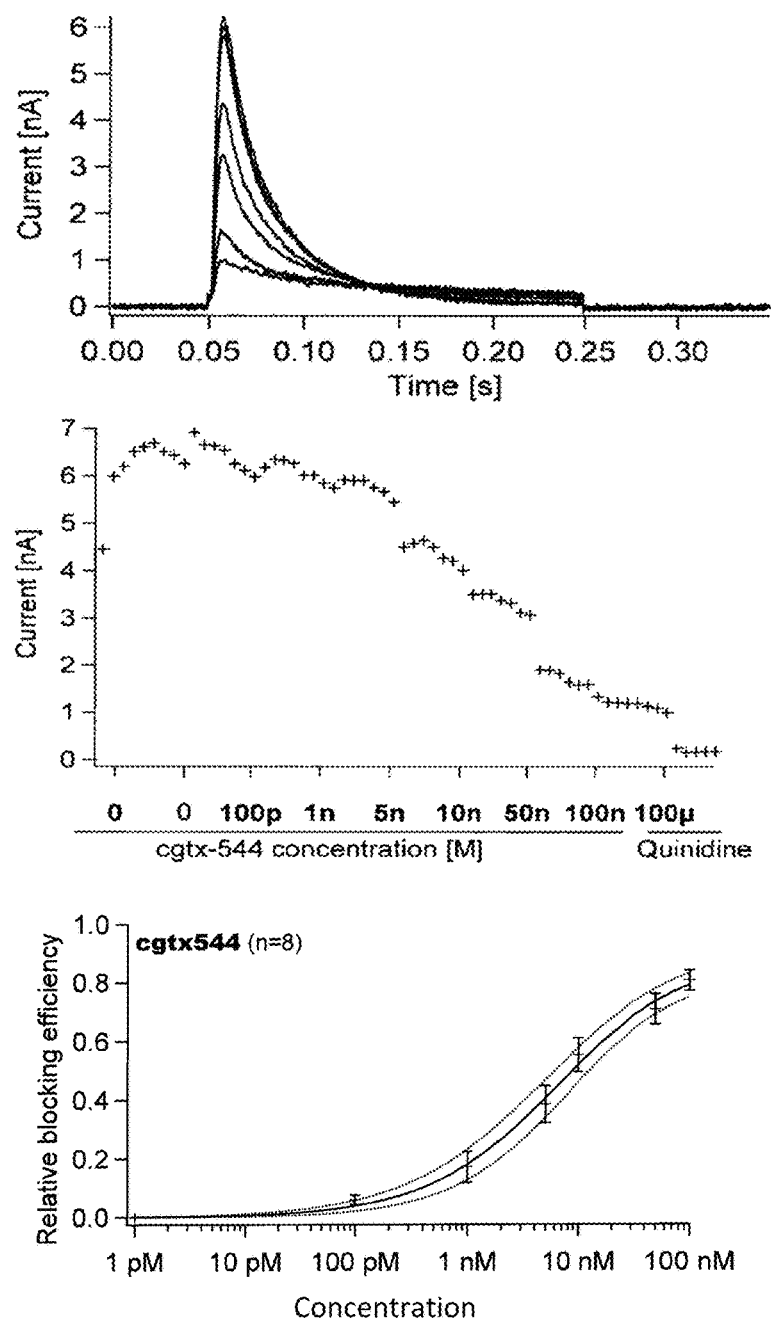
Figure 1F:
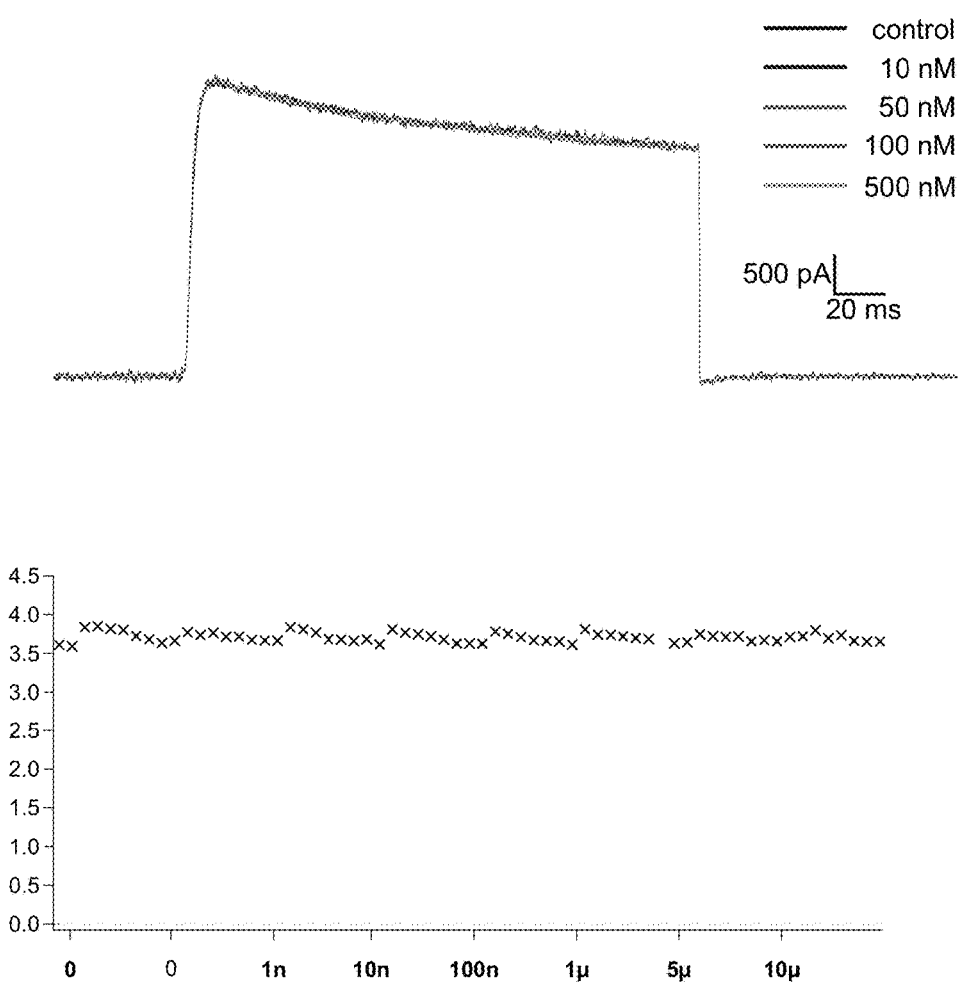

Compound 1: cgtx 538
Compound 2: cgtx 539
Compound 3: cgtx 540
Compound 4: cgtx 541
Compound 5: cgtx 542
Compound 6: cgtx 543
Compound 7: cgtx-544
Compound 8: cgtx 547

Left, example traces of hERG currents after application of external solution (black), compound application (blue) and quinidine (grey). The right panel shows the changes of peak current amplitude over time. Dotted lines indicate the compound application. The effect of each compound concentration was evaluated for 10 or 20 sweeps. All compounds seemed to have no or only little effect on hERG. Instead, quinidine did fully block the current. Note that a run down from begin of the compound application to the end of recorded sweeps occurred.

FIG. 4 Representative voltage dependent activation of Kv1.3 channels expressed in Sf21 cells (A) and endogenously expressed in $T_{EM}$ cells (B). (C) Pulse protocol for voltage dependent Kv1.3 activation.

Figure 5:
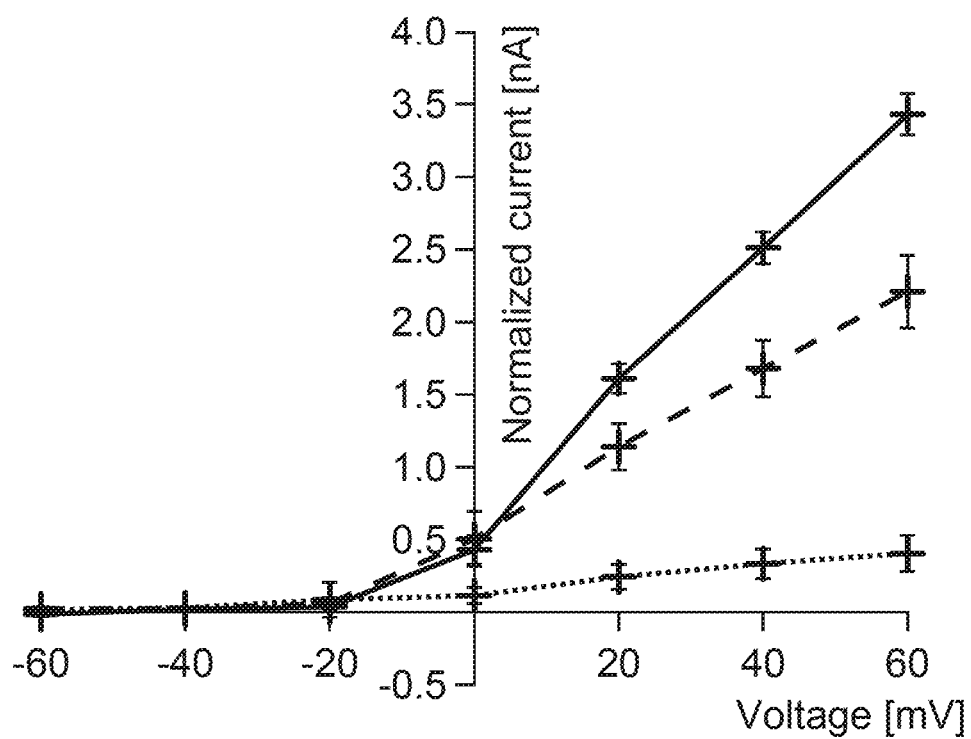

FIG. 5 Characteristic normalized voltage-current-correlation of Kv1.3 channels expressed in Sf21 (middle and upper lines) and $T_{EM}$ cells (lower line); n=41, n=12 and n=29, respectively. With the Sf21 Baculovirus expression system it is possible to express high amounts of Kv1.3 potassium channels.

Figure 6A:
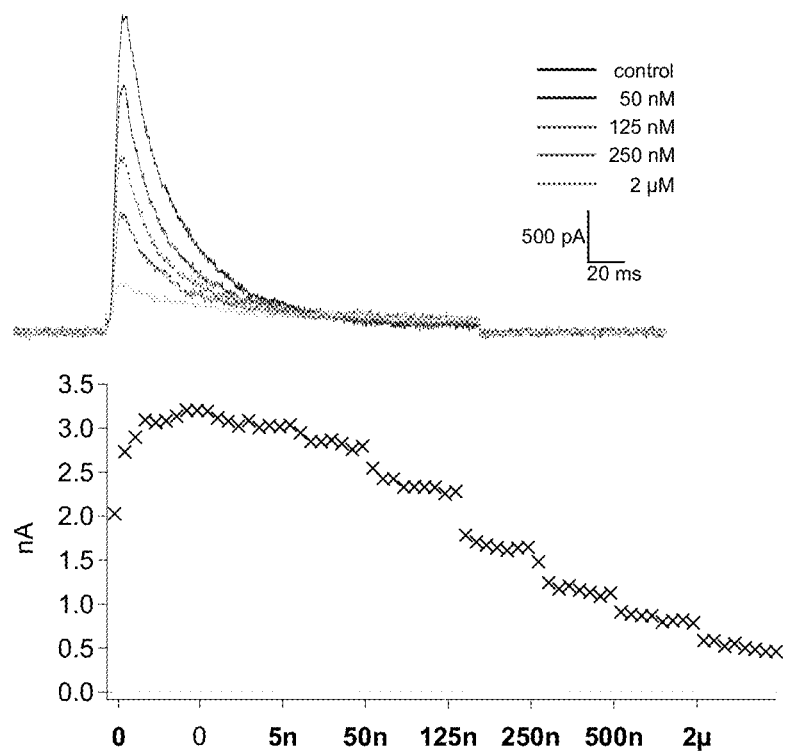
Figure 6B:
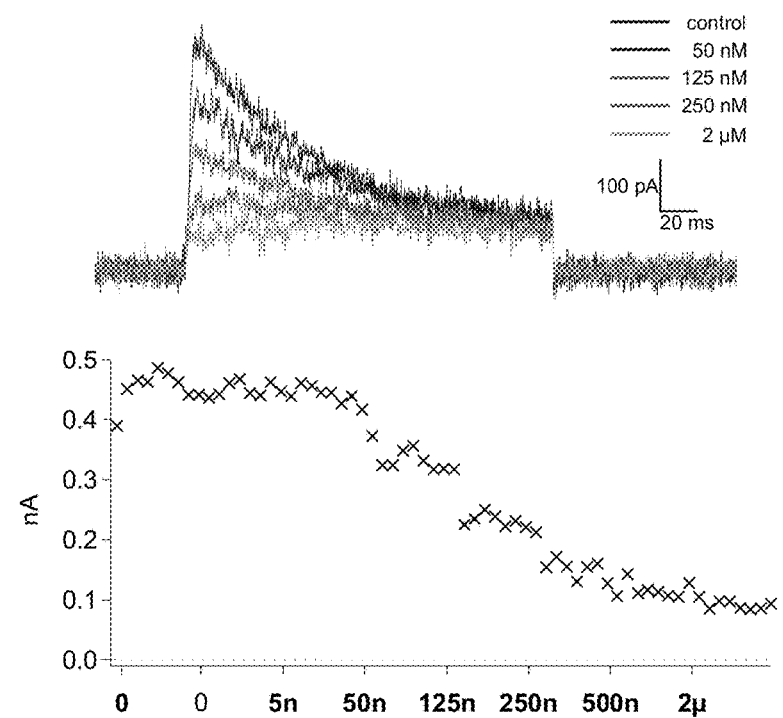

FIGS. 6A-6B Comparison of $T_{EM}$ cells and Sf21 cells. Block of Kv1.3 channels expressed in Sf21 (FIG. 6A) and $T_{EM}$ (FIG. 6B) cells by cgtx-544. Representative raw current traces and time dose responses in the presence of increasing concentrations of the Kv1.3 antagonistic peptide are shown.

Figure 7:
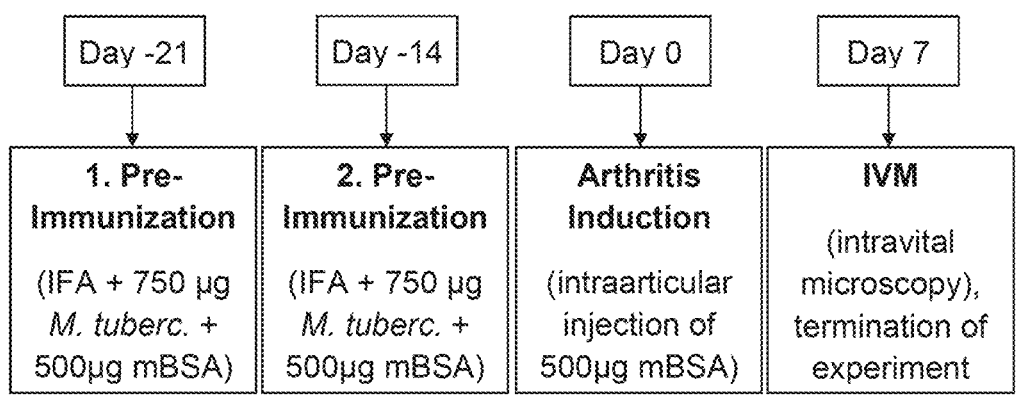
Figure 8:
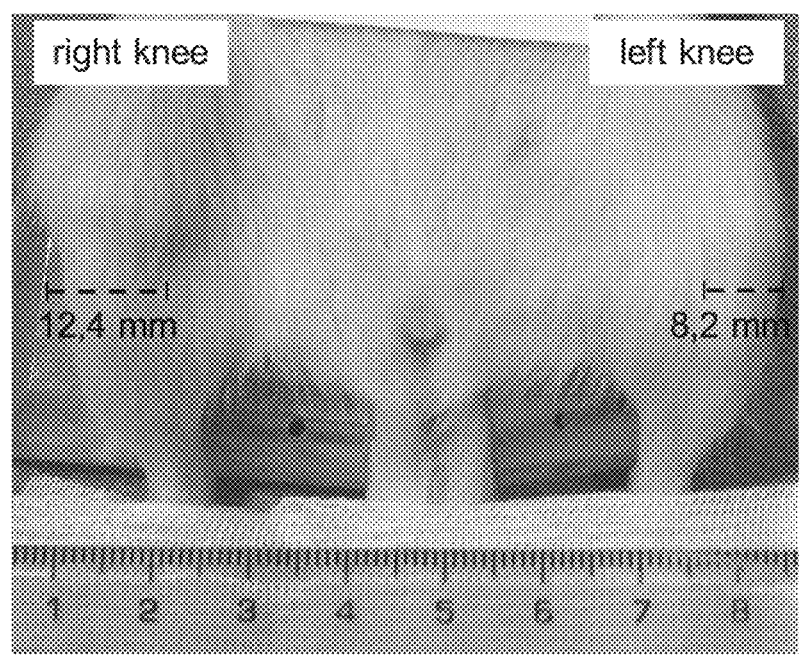
Figure 9:
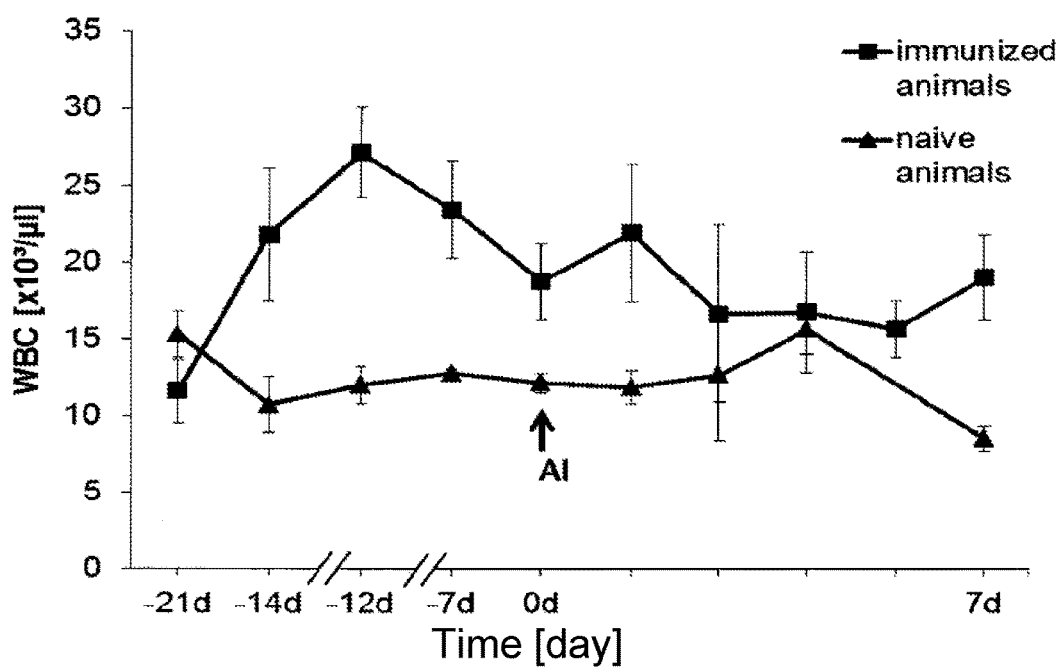
Figure 10:
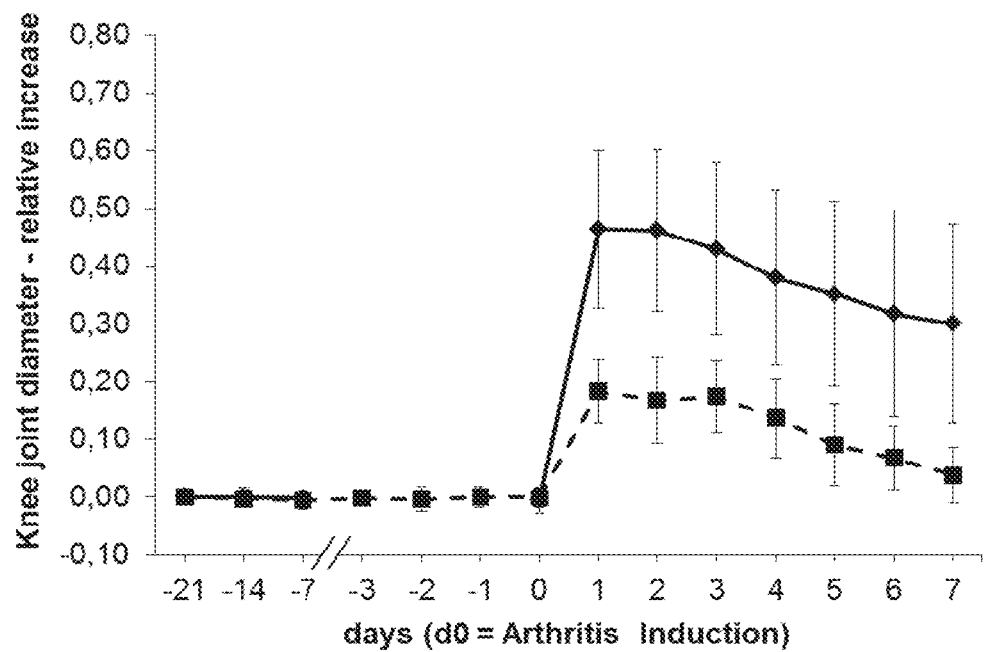

FIG. 7 Schematic representation of the local induction of arthritis in the rat knee FIG. 8 Swelling of the knee joint after induction of local arthritis FIG. 9 Immune status of experimental animals based on WBC counts in peripheral blood; AI: arthritis induction, naive animals=NaCl "immunized animals", immunized animals=animals treated with Freuds Adjuvant incl. mBSA FIG. 10 Difference of the swelling of the knee joint between cgtx-544 treated and untreated control animals (each group: n=14; solid line with rhombuses: untreated control animals; dash line with squares: cgtx-544 treated animals)

Figure 11:
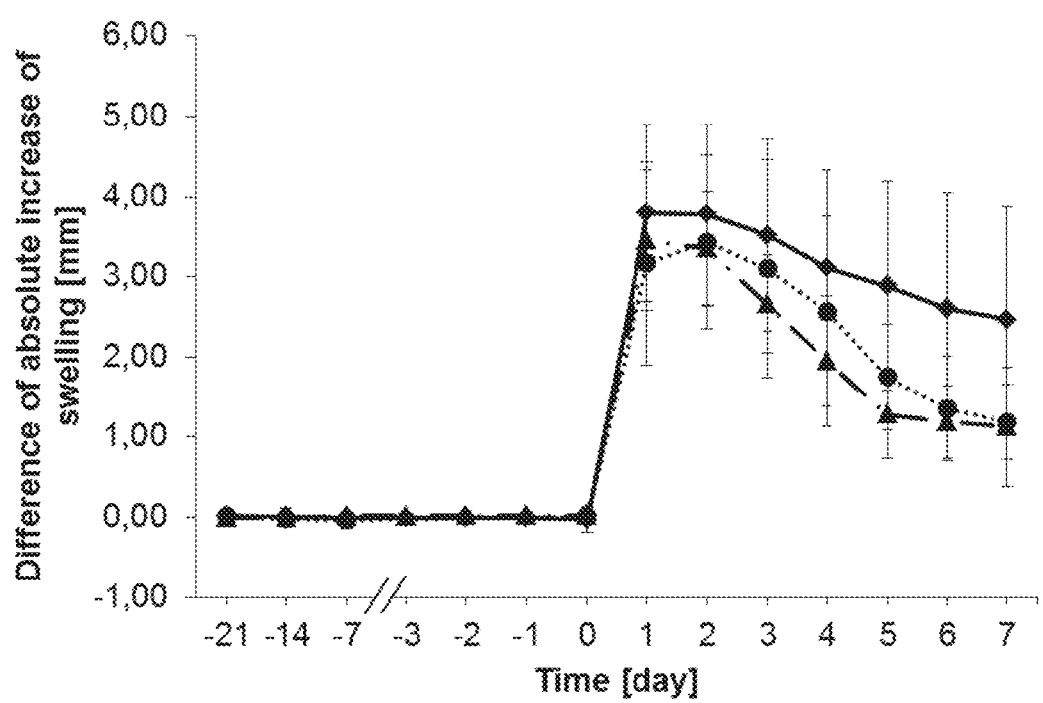

FIG. 11 Time course of difference of the absolute knee swelling increase in arthritic rats with Methotrexate (MTX) standard therapy. After two immunizations on day −21 and day −14 the antigen-induced arthritis (AIA) was induced by intra-articular injection of methylated BSA on day 0. The high-dose MTX therapy received an application of 1 mg/kg bodyweight MTX 1×weekly s.c. starting on day −21 up to day 0. The low-dose MTX therapy received a daily application of 100 µg/kg bodyweight MTX i.v. starting at day −3 up to day 6 and the vehicle control group received a daily application of 0.9% NaCl i.v. starting at day 0 up to day 6. The absolute increase of knee swelling is the difference between non-induced knee values and arthritis induced knee values separately for each group. Values are means±SD. Dotted line with filled circles: MTX s.c. 1×weekly group (group J, n=7); Long dash-dot line with triangles: MTX i.v. 1×daily group (group L, n=7); Solid line with rhombuses: vehicle (NaCl) control group (group H, n=14).

Figure 12:
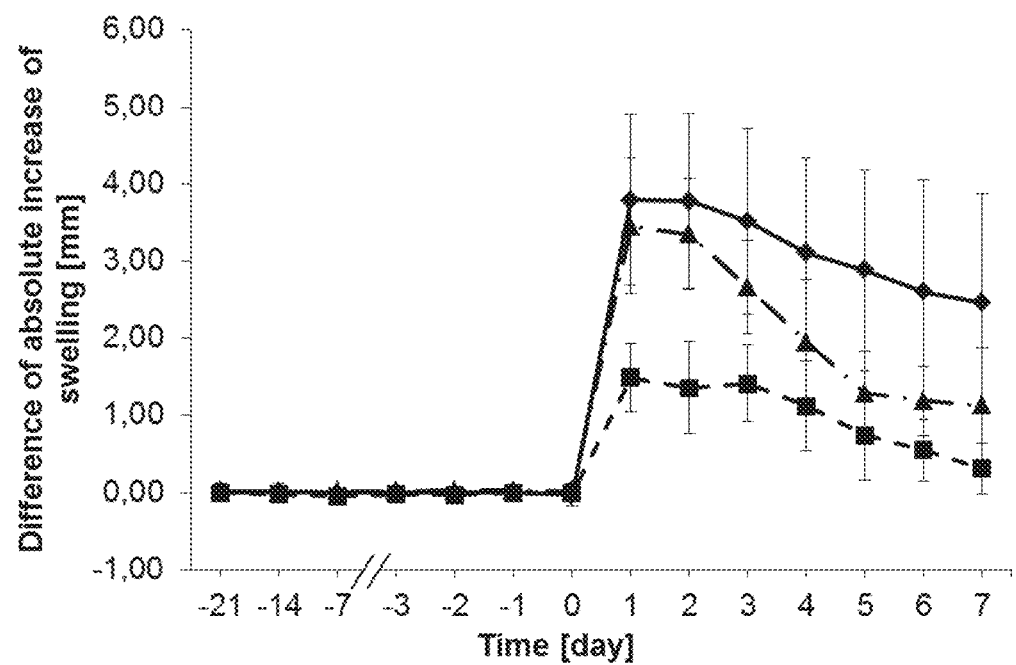

FIG. 12 Time course of difference of the absolute knee swelling increase in arthritic rats with Methotrexate (MTX) standard therapy in comparison to cgtx-544 peptide therapy. After two immunizations on day −21 and day −14 the antigen-induced arthritis (AIA) was induced by intra-articular injection of methylated BSA on day 0. The low-dose MTX therapy received a daily application of 100 µg/kg bodyweight MTX i.v. starting on day −3 up to day 6. In comparison the cgtx-544 therapy group received a daily application of 1 mg/kg bodyweight cgtx-544 i.v. starting on day −3 up to day 6 and the vehicle control group received also a daily application of 0.9% NaCl i.v. starting on day 0. The absolute increase of knee swelling is the difference between non-induced knee values and arthritis induced knee values separately for each group. Values are means±SD. Long-dash dot line with triangles: MTX i.v. 1×daily group (group L, n=7); Dash line with squares: cgtx-544 therapy group (group I; n=14); Solid line with rhombuses: vehicle (NaCl) control group (group H, n=14).

Figure 13:
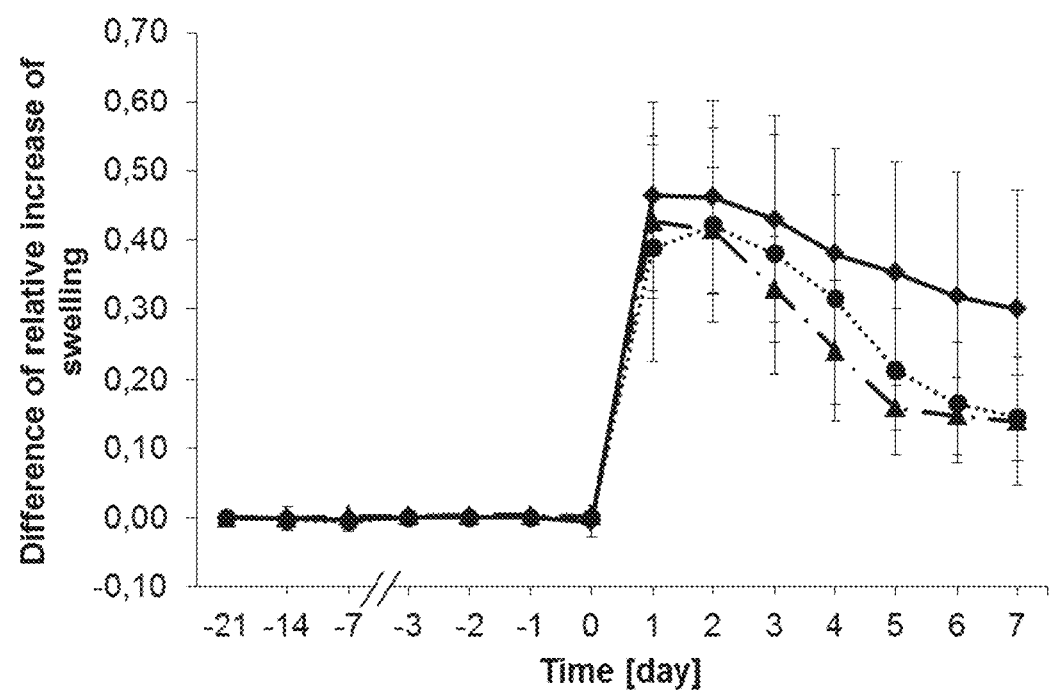

FIG. 13 Time course of difference of the relative knee swelling increase in arthritic rats with Methotrexate (MTX) standard therapy. After two immunizations on day −21 and day −14 the antigen-induced arthritis (AIA) was induced by intra-articular injection of methylated BSA on day 0. The high-dose MTX therapy received an application of 1 mg/kg bodyweight MTX 1×weekly s.c. starting on day −21 up to day 0. The low-dose MTX therapy received a daily application with 100 µg/kg bodyweight MTX i.v. starting at day −3 up to day 6 and the vehicle control group received a daily application of 0.9% NaCl i.v. starting at day 0 up to day 6. The relative increase of knee swelling is the difference between non-induced knee values and arthritis induced knee values separately for each group after normalization of the values. Normalized values (day −21=1) are means±SD. Dotted line with filled circles: MTX s.c. 1×weekly group (group J, n=7); Long dash-dot line with triangles: MTX i.v. 1×daily group (group L, n=7); Solid line with rhombuses: vehicle (NaCl) control group (group H, n=14).

Figure 14:
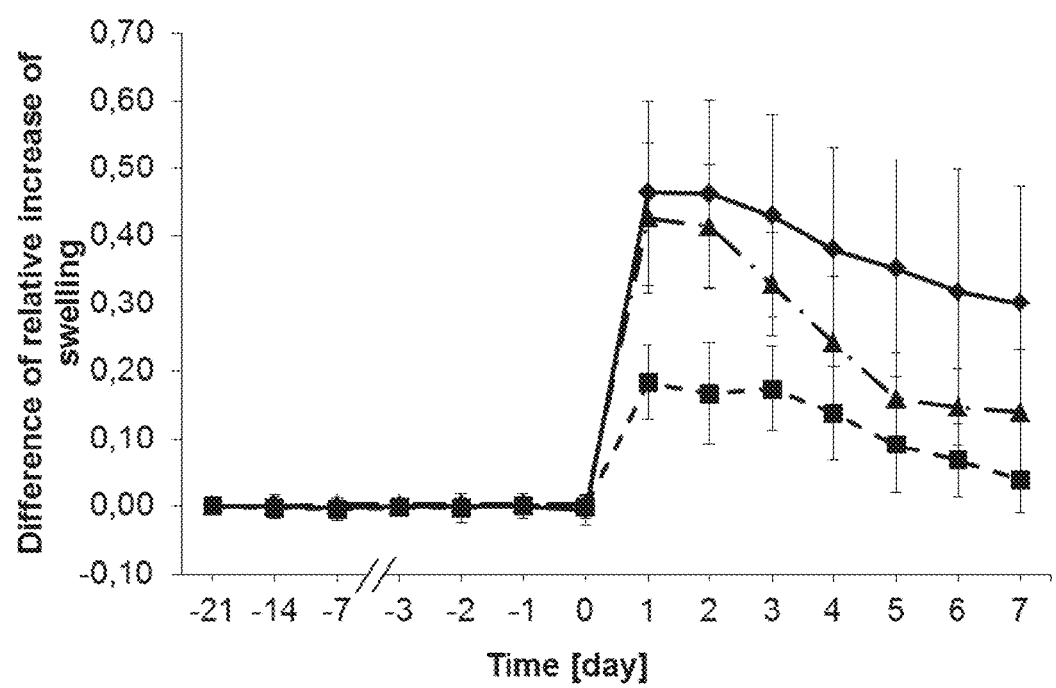

FIG. 14 Time course of difference of the relative knee swelling increase in arthritic rats with Methotrexate (MTX) standard therapy in comparison with cgtx-544 therapy. After two immunizations on day −21 and day −14 the antigen-induced arthritis (AIA) was induced by intra-articular injection of methylated BSA on day 0. The low-dose MTX therapy received a daily application of 100 µg/kg bodyweight MTX i.v. starting on day −3 up to day 6. In comparison the cgtx-544 therapy group received a daily application of 1 mg/kg bodyweight cgtx-544 i.v. starting on day −3 up to day 6 and the vehicle control group received also a daily application of 0.9% NaCl i.v. starting on day 0. The relative increase of knee swelling is the difference of non-induced knee values from arthritis induced knee values separately for each group after normalization of the values. Normalized values (day −21=1) are means±SD. Long dash-dot line with triangles: MTX i.v. 1×daily group (group L, n=7); Dash line with squares: cgtx-544 peptide therapy group (group I; n=14); Solid line with rhombuses: vehicle (NaCl) control group (group H, n=14).

Figure 15:
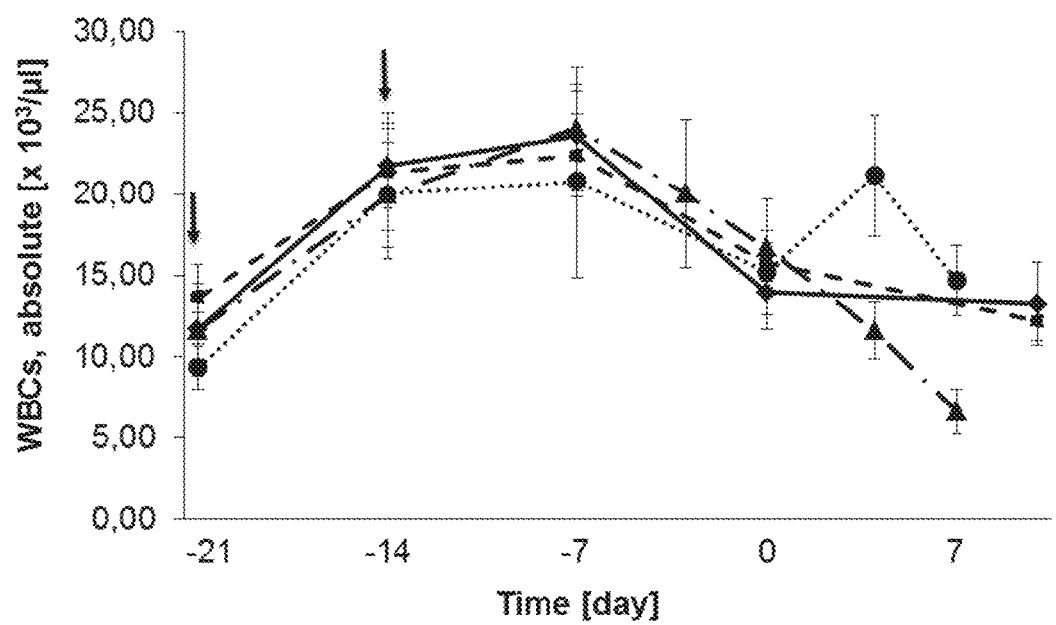

FIG. 15 Immune status of arthritic rats with Methotrexate (MTX) standard therapy in comparison to cgtx-544 therapy. White blood cell (WBC) count absolute; values are means±SD (n=7). Dotted line with filled circles: MTX s.c. 1×weekly group (group J, n=7); Long dash-dot line with triangles: MTX i.v. 1×daily group (group L, n=7); Dash line with squares: cgtx-544 peptide therapy i.v. 1×daily group (group I, n=7); Solid line with rhombuses: vehicle (NaCl) control i.v. 1×daily group (group H, n=7). Black arrows: immunization time with *M. tuberculosis* (750 µg) and mBSA. EDTA whole blood was measured with Sysmex XT-2000i.V.

FIG. 16 Neutrophil granulocytes in arthritic rats with Methotrexate (MTX) standard therapy in comparison to cgtx-544 therapy. A. Absolute values are means±SD (n=7). Dotted line with filled circles: MTX s.c. 1×weekly group (group J, n=7); Long dash-dot line with triangles: MTX i.v. 1×daily group (group L, n=7); Dash line with squares: cgtx-544 therapy i.v. 1×daily group (group I, n=7); Solid line with rhombuses: vehicle (NaCl) control i.v. 1×daily group (group H, n=7). Black arrows: immunization time with *M. tuberculosis* (750 µg) and mBSA. B. Relative neutrophils (in %) referred to the whole amount of WBC. Values are means±SD (n=7). Dotted line with filled circles: MTX s.c. 1×weekly group (group J, n=7); Long dash-dot line with triangles: MTX i.v. 1×daily group (group L, n=7); Dash line with squares: cgtx-544 therapy i.v. 1×daily group (group I, n=7); Solid line with rhombuses: vehicle (NaCl) control i.v. 1×daily group (group H, n=7). Black arrows (are supposed to days −21 and −14): immunization time with *M. tuberculosis* (750 µg) and mBSA. EDTA whole blood was measured with Sysmex XT-2000i.V.

FIG. 17 Time course of lymphocytes in arthritic rats with Methotrexate (MTX) standard therapy in comparison to cgtx-544 therapy. A. Absolute values are means±SD (n=7). Dotted line with filled circles: MTX s.c. 1×weekly group (group J, n=7); Long dash-dot line with triangles: MTX i.v. 1×daily group (group L, n=7); Dash line with squares: cgtx-544-peptide therapy i.v. 1×daily group (group I, n=7); Solid line with rhombuses: vehicle (NaCl) control i.v. 1×daily group (group H, n=7). Black arrows: immunization time with *M. tuberculosis* (750 µg) and mBSA. B. Percentage of lymphocytes in arthritic rats with Methotrexate (MTX) standard therapy in comparison to cgtx-544 therapy—Relative lymphocytes (in %) referred to the whole amount of WBCs. Values are means±SD (n=7). Dotted line with filled circles: MTX s.c. 1×weekly group (group J, n=7); Long dash-dot line with triangles: MTX i.v. 1×daily group (group L, n=7); Dash line with squares: cgtx-544 therapy i.v. 1×daily group (group I, n=7); Solid line with rhombuses: vehicle (NaCl) control i.v. 1×daily group (group H, n=7). Black arrows: immunization time with *M. tuberculosis* (750 μg) and mBSA. EDTA whole blood was measured with Sysmex XT-2000i.V.

Figure 18:
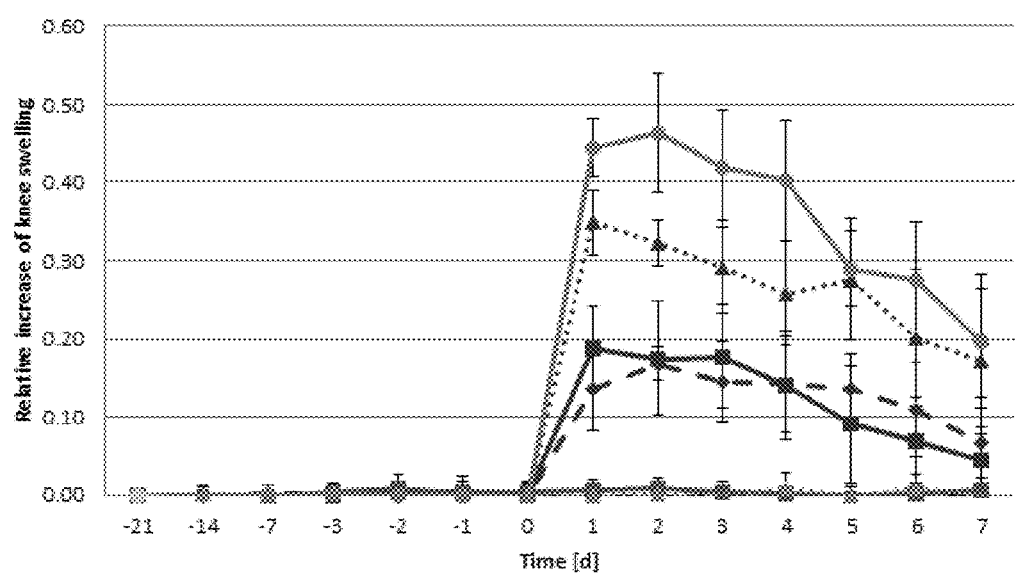

FIG. 18 Preventive treatment and dose dependency—Time course of relative increase of knee diameters (high/medium/low dose). Values are means±SD. Long dash-dot line with triangles: cgtx-544 peptide 5 mg/kg bodyweight therapy group (group N, n=5); Dash line with black squares: cgtx-544 peptide 1 mg/kg bodyweight therapy group (group I, n=14); Dotted line with filled circles: cgtx-544 peptide 0.1 mg/kg bodyweight therapy group (group M, n=5); Solid line with rhombuses: vehicle (NaCl) control group (group H #15-19, n=5). Solid lines with white squares: no increase of uninduced knee diameters (groups I, N, M and H; left uninduced knees).

Figure 19A:
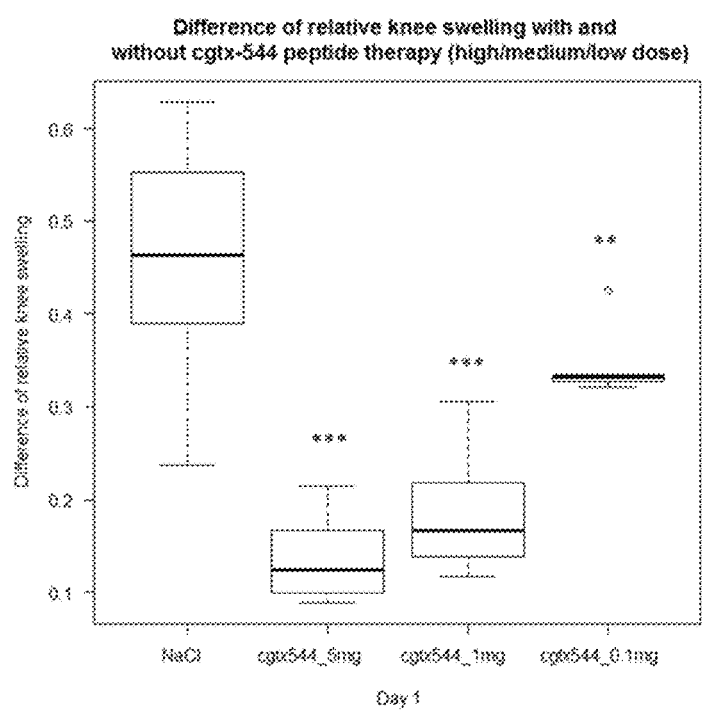
Figure 19B:
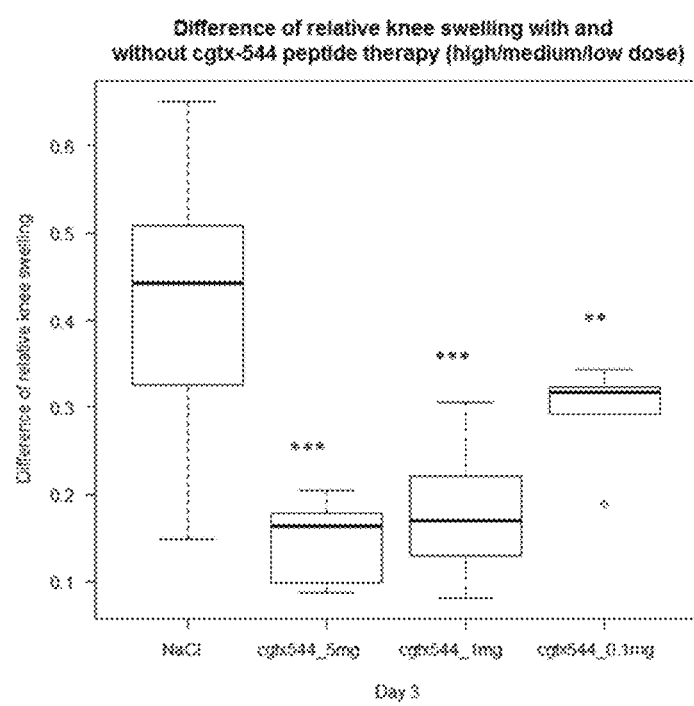

FIGS. 19A-19B Statistical analysis of cgtx-544 efficacy results: Difference of relative knee swelling with and without cgtx-544 peptide therapy (high/medium/low dose) on day 1(FIG. 19A) and day 3(FIG. 19B) after arthritis induction. All box plots are showing median, interquartile range, sample minimum and maximum. For the analysis of significance vehicle control was compared to therapy groups. *P<0.05, P<0.01, *P<0.001.

Figure 20:
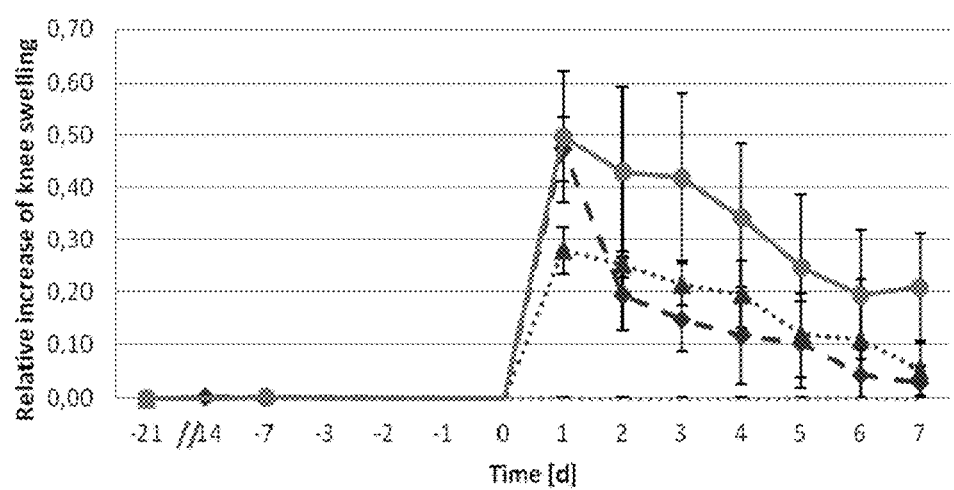

FIG. 20 Curative Treatment—Start of treatment on d=0 or d=1—Time course of difference of knee diameters (intra-individual, substraction ind./unind.) in arthritic rats with and without cgtx-544 peptide therapy (treatment start at d0 and d1). Values are means±SD. Long dash-dot line with triangles—start of treatment at d1: cgtx-544 peptide 1 mg/kg bodyweight therapy group (group Q, n=7); Dotted line with filled circles—start of treatment at d0: cgtx-544 peptide 1 mg/kg bodyweight therapy group (group P, n=6); Solid line with rhombuses: vehicle (NaCl) control group (group H). Solid lines with white squares: no increase of uninduced knee diameters (groups Q, P and H; left uninduced knees).

Figure 21A:
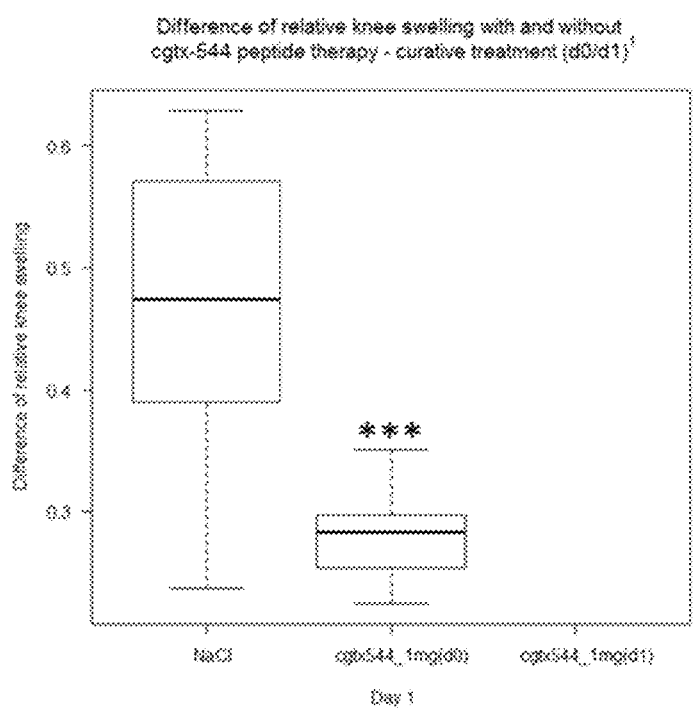
Figure 21B:
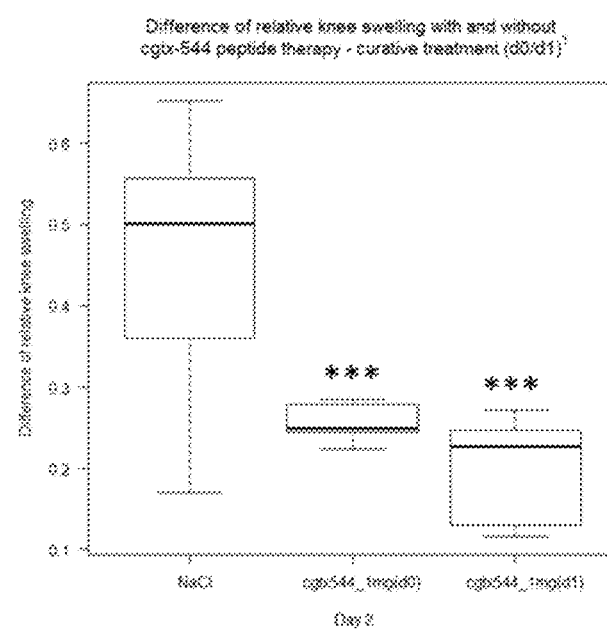
Figure 21C:
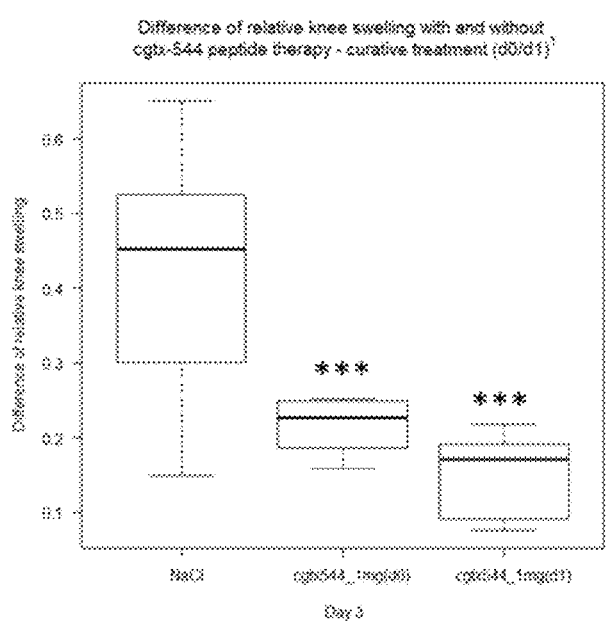

FIGS. 21A-21C Statistical analysis of cgtx-544 efficacy results on day 1(FIG. 21A), day 2(FIG. 21B) and day 3(FIG. 21C) after arthritis induction: Difference of relative knee swelling with and without cgtx-544 peptide therapy—curative treatment (starting d0/d1) All box plots are showing median, interquartile range, sample minimum and maximum. For the analysis of significance vehicle control was compared to therapy groups. *P<0.05, P<0.01, *P<0.001.

Figure 22:
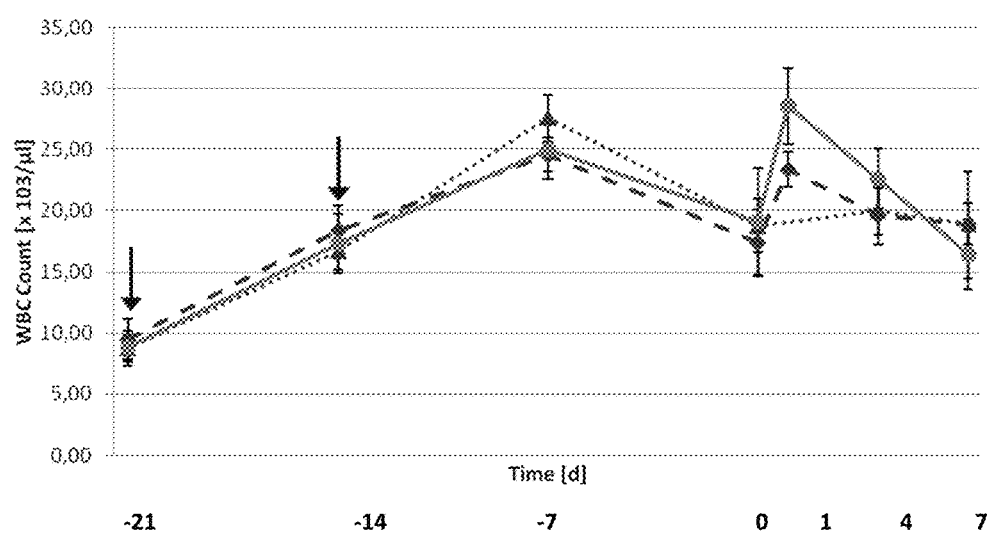

FIG. 22 Curative Treatment—Start of treatment on d=0 or d=1—Time course of WBC count in arthritic rats with and without cgtx-544 peptide therapy (treatment start at d0 and d1). White blood cell (WBC) count absolute; values are means±SD. Long dash-dot line with triangles—start of treatment at d1: cgtx-544(Mix) peptide 1 mg/kg bodyweight therapy group (group Q, n=7); Dotted line with filled circles—start of treatment at d0: cgtx-544 peptide 1 mg/kg bodyweight therapy group (group P, n=6); Solid line with rhombuses: vehicle (NaCl) control group (group H, n=5). Black arrows: immunization time with *M. tuberculosis* (750 μg) and mBSA.

Figure 23:
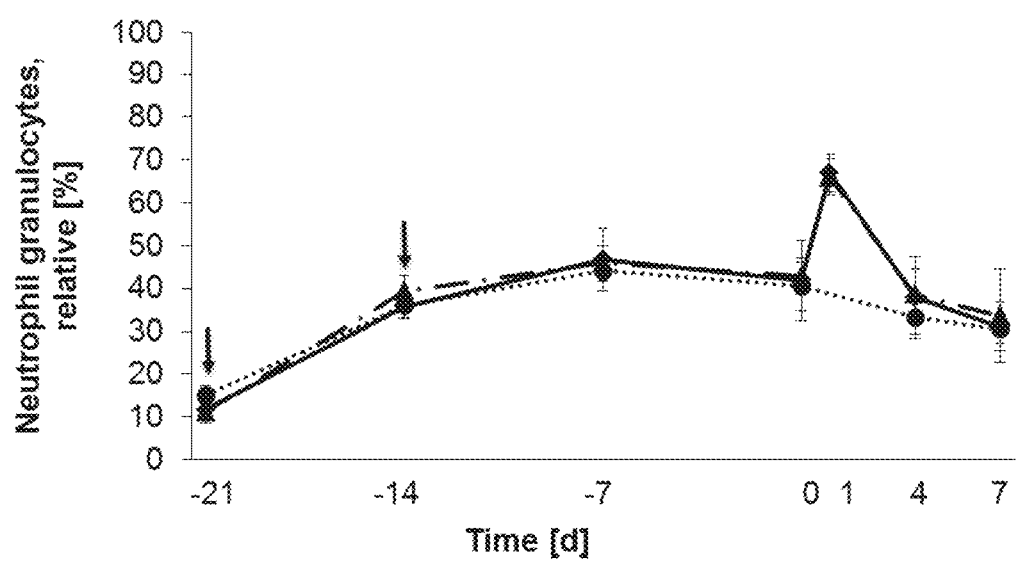

FIG. 23 Curative Treatment—Start of treatment on d=0 or d=1—Time course of relative amount of neutrophil granulocytes in percent of WBC in arthritic rats with and without cgtx-544 peptide therapy (treatment start at d0 and d1). Neutrophils (in %) relative to the whole amount of WBC. Values are means±SD. Long dash-dot line with triangles—start of treatment at d1: cgtx-544 peptide 1 mg/kg bodyweight therapy group (group Q, n=7); Dotted line with filled circles—start of treatment at d0: cgtx-544 peptide 1 mg/kg bodyweight therapy group (group P, n=6); Solid line with rhombuses: vehicle (NaCl) control group (group H, n=5). Black arrows: immunization time with *M. tuberculosis* (750 μg) and mBSA.

Figure 24:
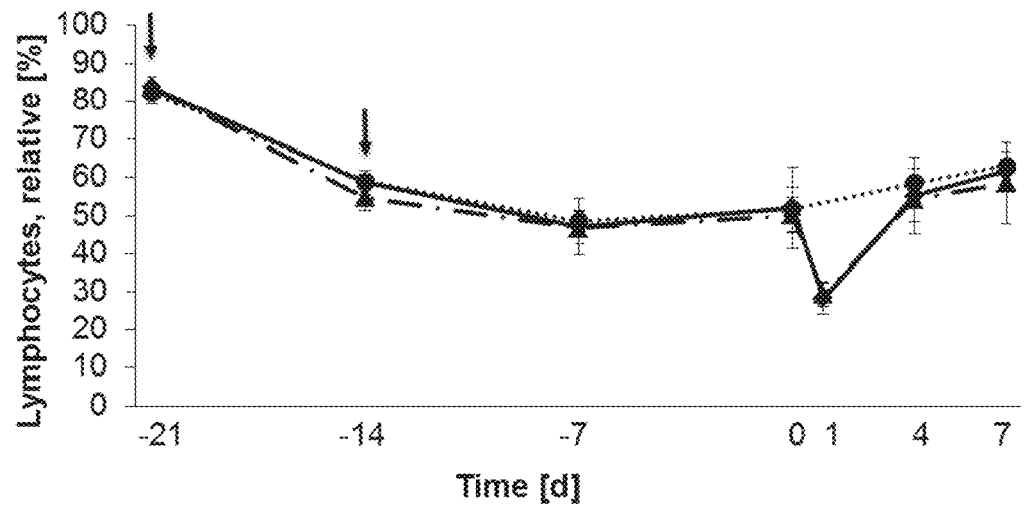

FIG. 24 Curative Treatment—Start of treatment on d=0 or d=1—Time course of relative amount of lymphocytes in percent of WBC in arthritic rats with and without cgtx-544 peptide therapy (treatment start at d0 and d1). Lymphocytes (in %) relative to the whole amount of WBCs. Values are means±SD. Long dash-dot line with triangles—start of treatment at d1: cgtx-544 peptide 1 mg/kg bodyweight therapy group (group Q, n=7); Dotted line with filled circles—start of treatment at d0: cgtx-544 peptide 1 mg/kg bodyweight therapy group (group P, n=6); Solid line with rhombuses: vehicle (NaCl) control group (group H, n=5). Black arrows: immunization time with *M. tuberculosis* (750 μg) and mBSA.

Figure 25:
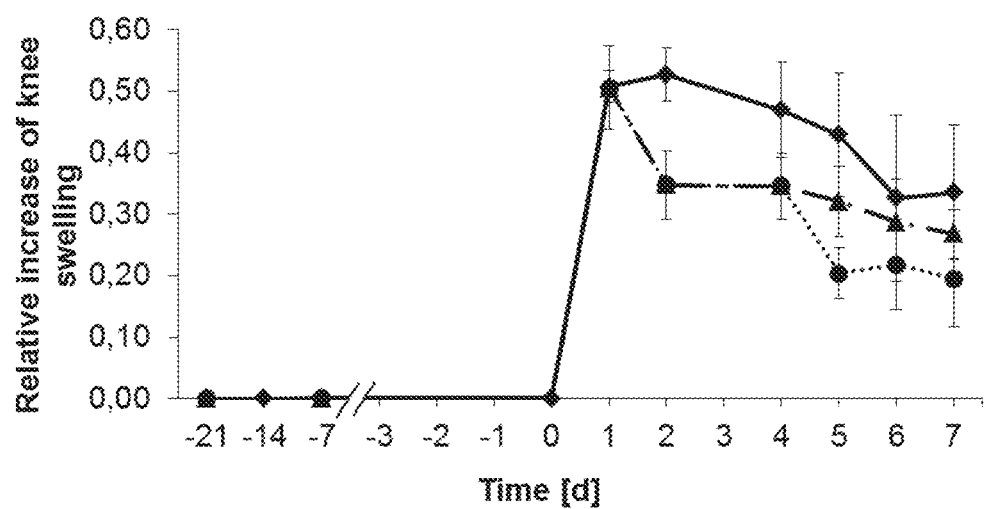

FIG. 25 Curative treatment (once per week or twice per week)—Time course of relative increase of knee joint diameter. Values are means±SD. Long dash-dot line with triangles—single treatment at d1: cgtx-544 peptide 1 mg/kg bodyweight therapy group (group R6-10, n=5); Dotted line with filled circles—single treatment at d1 and d4: cgtx-544 peptide 1 mg/kg bodyweight therapy group (group R1-5, n=5); both groups combined until day 4. Solid line with rhombuses: vehicle (NaCl) control group (group H, n=5).

FIG. 26 Curative treatment (once per week or twice per week)—Statistical analysis of cgtx-544 efficacy: Difference of relative knee swelling with and without cgtx-544 peptide therapy on day 2(A) and day 5(B) after arthritis induction. All box plots are showing median, interquartile range, sample minimum and maximum. For the analysis of significance vehicle control was compared to therapy groups. *p<0.05, p<0.01, *p<0.001.

FIG. 27 Analysis of mBSA specific antibodies. In the experimental groups H and I all animals have produced antibodies against the antigen mBSA during the immunization and AIA induction period. In the control group F (naïve animals) specific mBSA antibodies could not be detected.

FIG. 28 Statistical analysis of MTX efficacy results: Difference of relative knee swelling with and without MTX therapy (high/low dose) on day 1(A) and day 3(B) after arthritis induction. All box plots are showing median, interquartile range, sample minimum and maximum. For the analysis of significance vehicle control was compared to therapy groups. *P<0.05, P<0.01, *P<0.001, n.s. not significant.

Figure 29:
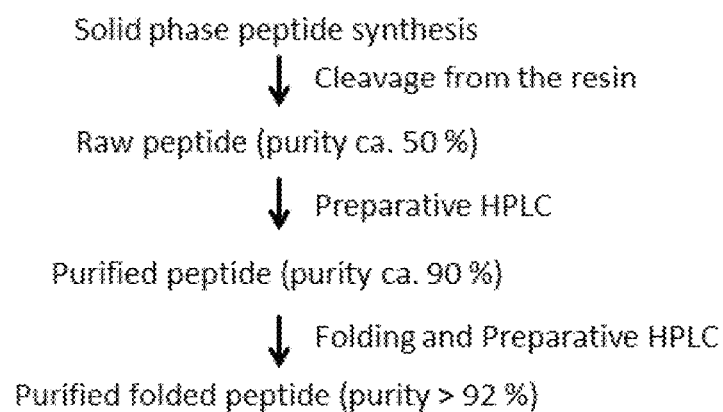

FIG. 29 Peptide synthesis scheme.

Figure 30:
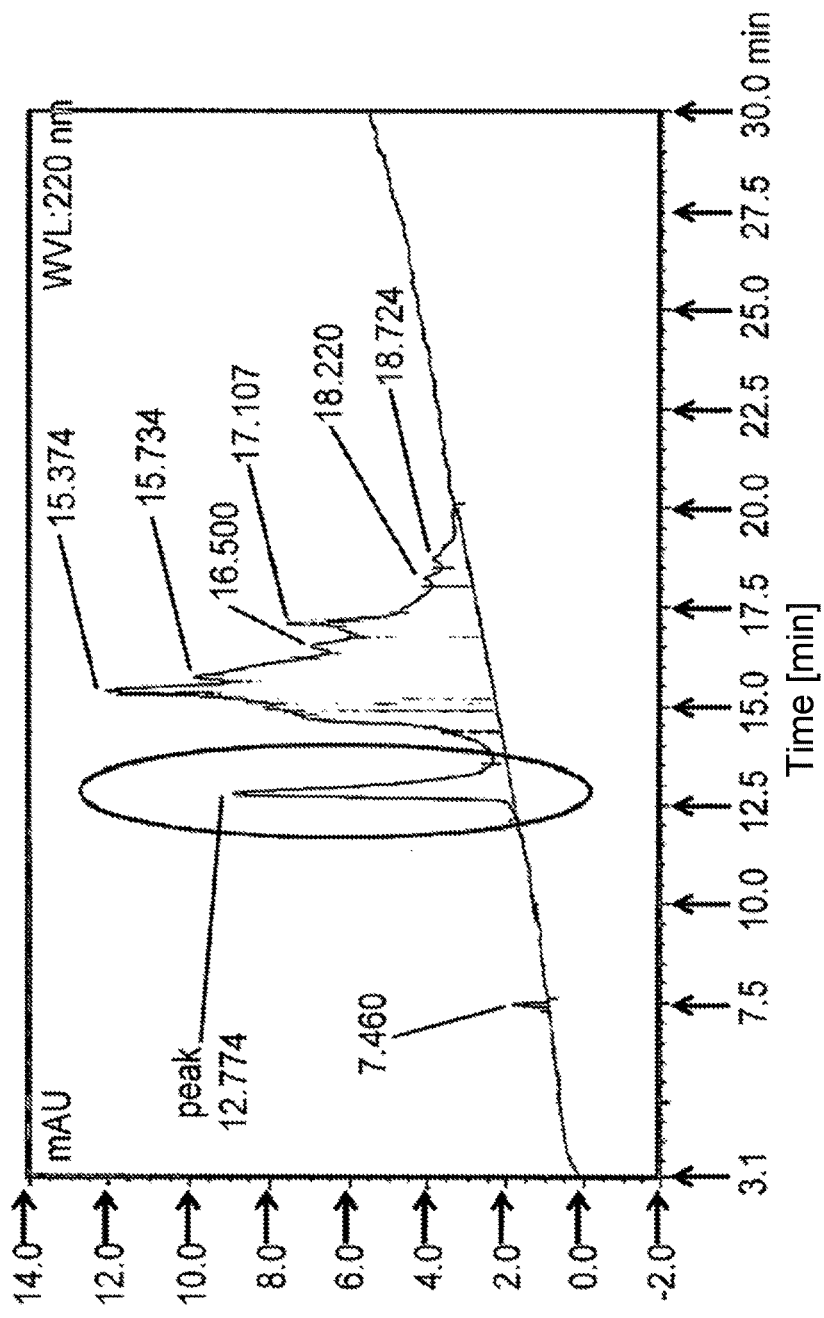

FIG. 30 UPLC profile of the cgtx-544 peptide after folding.

FIG. 31 IC50 of cgtx-544(Sing). A. cgtx-544(Sing) displayed an IC50 value of 6.9 nM when results are fitted to the Hill curve. B. Stepwise current reduction with increasing cgtx-544(Sing) concentrations. C. Current traces during measurement at different cgtx-544(Sing) concentrations.

Figure 32:
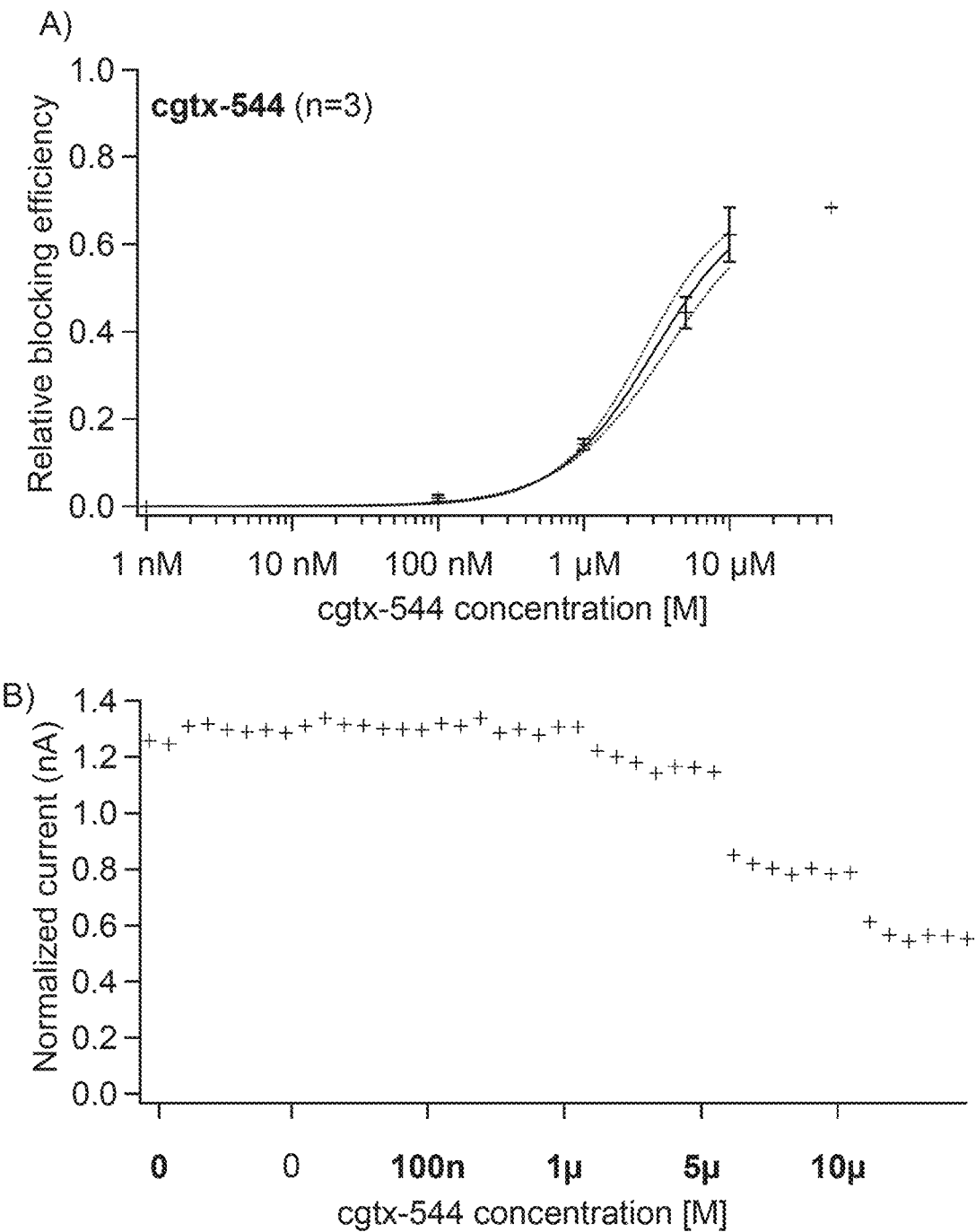

FIG. 32 Selectivity of cgtx-544(Sing). A. cgtx-544(Sing) displayed an IC50 value of about 6 μM on Kv1.1 when results are fitted to the Hill curve. B. Stepwise current reduction with increasing cgtx-544(Sing) concentrations on Kv1.1. C. Current traces during measurement at different cgtx-544(Sing) concentrations on Kv1.1. D. A 10 μM solution of cgtx-544(Sing) did not induce a significant reduction of Kv1.5 currents, while the currents were sensitive to quinidine. E. A 100 nM solution of cgtx-544(Sing) did not alter the Kv1.2 currents in stably transfected CHO cells. Concentrations >1 μM resulted in only slightly reduced currents. The IC50 was established at 2.5 μM.

FIG. 33 Decay of cgtx-544(Sing) in human serum at 37° C. A known amount of cgtx-544(Sing) was added to human blood serum from 3 blood donors and incubated at 37° C. for a period of 57 days. The blocking activity of the peptide was measured on Kv1.3 channels over this period. The peptide remains stable for 16 h, and it can still be detected after 45 days. At 57 days the blocking effect is no longer visible. Decay is depicted as the reduction of concentration of cgtx-544 (Sing) as determined by: C(t)=IC50 (t0/IC50(t) ·C0. The decay is fitted by a simple decay curve: C(t)=C0.2 (−t/t½), where C0 is the initial concentration of peptide in solution, t0 is the 0 min incubation at 37° C. point, and t½ is the half-life.

FIG. 34 Decrease of cgtx-544(Sing) in the serum of treated rats after i.v. injection. The concentration of unbound circulating cgtx-544(Sing) was calculated on the basis of a standard curve. Standard error of the mean is depicted in the error bars (n=6).

FIG. 35 A. Prolonged incubation of cgtx-544 results in a picomolar IC50 value. The Kv1.3 currents were normalized to the initial peak currents and the full block by the non-specific potassium channel blocker quinidine (data not shown). While under control conditions (upper curve, n=11) currents are stable for at least 10 minutes, a single application (arrow) of cgtx-544 (lower curve, n=13) causes a block which increases over time. B. Dose response curve of cgtx-544 at prolonged incubation times. In a black dash line a dose-response curve for cgtx-544 with short incubation times is shown. The black solid curve results when cgtx-544 is incubated with Kv1.3 channels for prolonged times, i.e. 15 min. The observed block of 20% with short incubation times (white dot) compared to the 60% block with long incubation times (black dot) results in a left shift of the dose-response curve and therefore the IC50 (horizontal dotted line), is lower. C. IC50 values of cgtx-544 on Kv1.3 and Kv1.1 with long and short incubation times.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. One and three letter amino acid abbreviations used herein correspond to IUPAC nomenclature (see e.g. European Journal of Biochemistry, 138:9-37, 1984).

The following definitions are introduced:

As used in this specification and in the intended claims, the singular forms of "a" and "an" also include the respective plurals unless the context clearly dictates otherwise.

It is to be understood that the term "comprise", and variations such as "comprises" and "comprising" is not limiting. For the purpose of the present invention the term "consisting of" is considered to be a preferred embodiment of the term "comprising". If hereinafter a group is defined to comprise at least a certain number of embodiments, this is meant to also encompass a group which preferably consists of these embodiments only.

The terms "about" and "approximately" in the context of the present invention denote an interval of accuracy that a person skilled in the art will understand to still ensure the technical effect of the feature in question. The term typically encompasses a deviation from the indicated numerical value of ±10% and preferably of ±5%.

The term "peptide" as used herein refers to a molecular chain of amino acids and does not refer to a specific length of the product; thus, polypeptides, oligopeptides and proteins are included within the definition of peptide. Peptides according to the definition may be both naturally occurring peptides and synthetic peptides that may include naturally or non-naturally occurring amino acids. Further included within the definition are functional derivatives of the peptides, i.e. peptides that are chemically modified, e.g. by modifying a side chain, a free amino and/or carboxy-terminus of a natural or non-naturally occurring amino acid, preferably without changing the identity of the respective amino acid. For example, the side chain or a free amino or carboxy-terminus of an amino acid of a peptide may be modified by e.g. glycosylation, amidation, phosphorylation, ubiquitination, carboxylation e.t.c. In a preferred embodiment a peptide according to the invention may be modified by PEGylation, HESylation or PASylation.

The compounds disclosed herein have surprisingly been found by the inventors of the present invention to be capable of selectively binding to the Kv1.3 potassium channel over other potassium channels, such as e.g. Kv1.1, Kv 1.2, Kv1.5, Kv1.6, IKCa1, hERG or large-conductance Ca2+-activated K+ channels (BK channels). Given the prevalence of Kv1.3 in $T_{EM}$ cells, the compounds according to the present invention therefore constitute powerful therapeutic agents for $T_{EM}$-cell mediated diseases, such as e.g. auto immune diseases. Furthermore, the disclosed compounds provide the advantage of reduced side effects, as they do not substantially modulate the activity of other potassium channels distributed to other types of cells or tissues.

The invention thus generally relates to compounds which are capable of selectively binding to the Kv1.3 potassium channel over other potassium channels, such as e.g. Kv1.1. Such compounds are contemplated for use in the treatment or prevention of autoimmune diseases. Such compounds may be selected from the group consisting of a peptide, an antibody or a small molecule. In a particularly preferred embodiment said compound is a peptide as described for a first, second and third aspect of the invention and variants thereof.

An antibody capable of selectively binding to the potassium channel Kv1.3 may be a monoclonal or polyclonal antibody. In some embodiments the antibody may also be selected from antibody variants or fragments such as e.g. single chain antibodies, diabodies, minibodies, single chain Fv fragments (sc(Fv)), $sc(Fv)_2$ antibodies, Fab fragments or a $F(ab')_2$ fragments, provided that said antibody variants or fragments are capable of selectively binding to the potassium channel Kv1.3.

The term "small molecule" as used herein refers to small organic compounds having low molecular weight.

A small molecule may be a synthetic compound not known to occur in nature or a naturally-occurring compound isolated from or known to occur in natural sources, such as e.g. cells, plants, fungi, animals and the like. A small molecule in the context of the present invention preferably has a molecular weight of less than 5000 Dalton, more preferably of less than 4000 Dalton, more preferably less than 3000 Dalton, more preferably less than 2000 Dalton or even more preferably less than 1000 Dalton. In a particularly preferred embodiment a small molecule in the context of the present invention has a molecular weight of less than 800 Dalton.

In another preferred embodiment a small molecule in the context of the present invention has a molecular weight of 50 to 3000 Dalton, preferably of 100 to 2000 Dalton, more preferably of 100 to 1500 Dalton and even more preferably of 100 to 1000 Dalton. Most preferably a small molecule in the context of the present invention has a molecular weight of 100 to 800 Dalton.

Small molecules capable of selectively binding to the potassium channel Kv1.3 may e.g. be identified by screening small compound libraries.

The present invention in a first, second, and third aspect and variations thereof thus relates to peptide compounds which are capable of selectively binding to the potassium channel Kv1.3. Preferably, said compounds are capable of selectively binding to the potassium channel Kv1.3 over other potassium channels, such as e.g. Kv1.1, Kv 1.2, Kv1.5, Kv1.6, IKCa1, hERG or large-conductance Ca2+-activated K+ channels (BK channels). In a particularly preferred embodiment, compounds according the invention are capable of selectively binding to the potassium channel Kv1.3 over the potassium channel Kv1.1.

In a first aspect, the compound according to the invention comprises or consists of an amino acid sequence:

(SEQ ID No.: 23)
$X_1-X_2-X_3-N-V-X_4-C-X_5-X_6-X_7-X_8-X_9-C-X_{10}-X_{11}-X_{12}-C-X_{13}-$
$X_{14}-X_{15}-T-G-C-P-X_{16}-X_{17}-K-C-M-N-R-K-C-X_{18}-C-X_{19}-X_{20}-C,$ wherein $X_1$=T,Q,S,Y,N; $X_2$=I,F,V,A,L,W; $X_3$=I,T,Y,S,V,A,L; $X_4$=K,S,T,Y,R; $X_5$=R,T,K,S,Y; $X_6$=T,G,S,N,I,K,Q,A,V,L,Y; $X_7$=P,S,T; $X_8$=R,K,P; $X_9$=D,Q,N,E; $X_{10}$=A,Y,I,L,W,S,T,V,L,F; $X_{11}$=D,R,P,K,E,S,T,Y; $X_{12}$=P,H,V,I,L,A; $X_{13}$=R,K,Q,N; $X_{14}$=K,D,A,R,E,V,L,I; $X_{15}$=E,Q,A,L,D,N,V,I; $X_{16}$=Y,N,S,T,Q; $X_{17}$=A,G,V,I,L; $X_{18}$=K,R, $X_{19}$=Y,N,Q,T,S and $X_{20}$=G,R,K.

In a variation of the first aspect, the present invention also relates to a compound comprising or consisting of an amino acid sequence according to SEQ ID No: 23,
wherein $X_1$=T,Q,S,Y,N; $X_2$=I,F,V,A,L,W; $X_3$=I,T,Y,S,V,A,L; $X_4$=K,S,T,Y,R; $X_5$=R,T,K,S,Y; $X_6$=T,G,S,N,I,K,Q,A,V,L,Y; $X_7$=P,S,T; $X_8$=R,K,P; $X_9$=D,Q,N,E; $X_{10}$=A,Y,I,L,W,S,T,V,L,F; $X_{11}$=D,R,P,K,E,S,T,Y; $X_{12}$=P,H,V,I,L,A; $X_{13}$=R,K,Q,N; $X_{14}$=K,D,A,R,E,V,L,I; $X_{15}$=E,Q,A,L,D,N,V,I; $X_{16}$=Y,N,S,T,Q; $X_{17}$=A,G,V,I,L; $X_{18}$=K,R, $X_{19}$=Y,N,Q,T,S and $X_{20}$=G,R,K; and
wherein the compound is capable of selectively binding to the potassium channel Kv1.3.

In a preferred embodiment of the first aspect, the compound according to the invention comprises or consists of an amino acid sequence:

(SEQ ID No.: 24)
$X_1-X_2-X_3-N-V-X_4-C-X_5-X_6-X_7-X_8-X_9-C-X_{10}-X_{11}-X_{12}-C-X_{13}-$
$X_{14}-X_{15}-T-G-C-P-X_{16}-X_{17}-K-C-M-N-R-K-C-X_{18}-C-X_{19}-X_{20}-C;$ wherein $X_1$=T,Q; $X_2$=I,F; $X_3$=I,T; $X_4$=K,S; $X_5$=R,T,K; $X_6$=T,G,S,N,I; $X_7$=P,S; $X_8$=R,K,P; $X_9$=D,Q,N,E; $X_{10}$=A,Y,I,L,W; $X_{11}$=D,R,P,K,E,S; $X_{12}$=P,H,V; $X_{13}$=R,K,Q; $X_{14}$=K,D,A,R; $X_{15}$=E,Q,A,L; $X_{16}$=Y,N; $X_{17}$=A,G; $X_{18}$=K,R, $X_{19}$=Y,N and $X_{20}$=G,R.

In a preferred embodiment of the variation of the first aspect, the present invention also relates to a compound comprising or consisting of an amino acid sequence according to SEQ ID No: 24,
wherein $X_1$=T,Q; $X_2$=I,F; $X_3$=I,T; $X_4$=K,S; $X_5$=R,T,K; $X_6$=T,G,S,N,I; $X_7$=P,S; $X_8$=R,K,P; $X_9$=D,Q,N,E; $X_{10}$=A,Y,I,L,W; $X_{11}$=D,R,P,K,E,S; $X_{12}$=P,H,V; $X_{13}$=R,K,Q; $X_{14}$=K,D,A,R; $X_{15}$=E,Q,A,L; $X_{16}$=Y,N; $X_{17}$=A,G; $X_{18}$=K,R, $X_{19}$=Y,N and $X_{20}$=G,R; and
wherein the compound is capable of selectively binding to the potassium channel Kv1.3.

In a more preferred embodiment of the first aspect and its variation, the compound according to the invention comprises or consists of an amino acid sequence of SEQ ID No.25 (cgtx-544) or SEQ ID No.26 (cgtx 547). In this context, another more preferred embodiment of the first aspect and its variations, the compound according to the invention comprises or consists of an amino acid sequence which has at least about 50%, at least about 60%, at least about 70%, at least about 80%, at least about 90%, at least about 95%, at least about 96%, at least about 97%, at least about 98% or at least about 99% percentage identity to SEQ ID No.25 (cgtx-544). The determination of percent identity between two sequences is preferably accomplished using the mathematical algorithm of Karlin and Altschul (1993) Proc. Natl. Acad. Sci USA 90: 5873-5877. Such an algorithm is e.g. incorporated into the BLASTn and BLASTp programs of Altschul et al. (1990) J. Mol. Biol. 215: 403-410. The determination of percent identity is preferably performed with the standard parameters of the BLASTn and BLASTp programs. BLAST polynucleotide searches are preferably performed with the BLASTn program. For the general parameters, the "Max Target Sequences" box may be set to 100, the "Short queries" box may be ticked, the "Expect threshold" box may be set to 10 and the "Word Size" box may be set to 28. For the scoring parameters the "Match/mismatch Scores" may be set to 1, -2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "Mask lower case letters" box may not be ticked. BLAST protein searches are preferably performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension:1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked."

In an even more preferred embodiment of the first aspect and its variation, the compound according to the invention comprises or consists of an amino acid sequence of SEQ ID No.25 (cgtx-544).

The embodiments described hereinafter refer preferably to compounds of the first aspect of the invention and its variation. However, it needs to be understood that these embodiments, e.g. the length of peptides as discussed hereinafter, the selectivity to Kv1.3 vs. Kv1.1 etc. also apply to compounds of the second and third aspects of the invention and their variation as well as preferred embodiments thereof as described hereinafter.

In a further preferred embodiment a compound according to the invention is a peptide.

If the compound according to the invention is a peptide, a compound according to the invention preferably has a length of less than 1000 amino acids, less than 500 amino acids, less than 200 amino acids, preferably of less than 150 amino acids, of less than 100 amino acids, less than 90 amino acids, less than 80 amino acids, less than 70 amino acids, less than 60 amino acids, less than 50 amino acids or less than 40 amino acids.

In a further preferred embodiment a compound according to the invention has a length of between at least 20 and 1000 amino acids, preferably between at least 25 and 500 amino acids, more preferably between at least 30 and 200 amino acids, more preferably between at least 34 and 150 amino acids, more preferably between at least 34 and 100 amino acids, more preferably between at least 34 and 90 amino acids, and even more preferably between at least 34 and 80 amino acids, between at least 34 and 70 amino acids, between 34 and 60 amino acids, between 34 and 50 amino acids or between 34 and 40 amino acids.

In a more preferred embodiment a compound according to the invention essentially consists of the amino acid sequence as indicated.

The amino acids comprised in the compounds according to the invention may be L- or D-amino acids. Preferably, the amino acids comprised in the compounds according to the invention are L-amino acids. In some embodiments, in particular in cases where high resistance to proteolysis is desired, D-amino acids may be preferred.

Compounds inhibiting the activity of different potassium channels at the same time might have significant side effects if applied to a living organism due to the differential distribution of different potassium channels to different types of cells. The present invention therefore provides compounds, which are capable of selectively binding to the potassium channel Kv1.3 in comparison to other potassium channels, in particular in comparison to the potassium channel Kv1.1.

The term "selectively binding" as used herein refers to the preferential binding of a compound according to the invention to the Kv1.3 channel over other ion channels and particularly over other potassium channels like e.g. Kv1.1, Kv 1.2, Kv1.5, Kv1.6, IKCa1, hERG or large-conductance Ca2+-activated K+ channels (BK channels).

Preferably, a compound according to the invention is capable of selectively binding to the potassium channel Kv1.3 over the potassium channel Kv1.1. In this case, a compound according to the invention binds to the Kv1.3 channel with a substantially higher affinity than to the Kv1.1 channel.

In the context of the present invention the toxin HsTx 1 is not considered as a compound which is capable of selective binding to the potassium channel Kv1.3, as it also binds to and potently inhibits Kv1.1 channels.

In a preferred embodiment a compound which according to the invention selectively binds to Kv1.3, binds to the potassium channel Kv1.3 with a $K_d$ value that is at least 2 fold, 5 fold, 10 fold, 100 fold, 1000 fold, 2000 fold, preferably at least 3000, 4000, 5000, 6000, 7000, 8000, 9000 or 10000 fold lower in comparison to the $K_d$ value with which said compound binds to the Kv1.1 channel. In a further preferred embodiment a compound which according to the invention selectively binds to Kv1.3, binds to the potassium channel Kv1.3 with a $K_d$ value that is at least 4000, 5000 or 10000 fold lower in comparison to the $K_d$ value with which said compound binds to other potassium channels like e.g. Kv1.1, Kv 1.2, Kv1.5, Kv1.6, IKCa1, hERG or large-conductance Ca2+-activated K+ channels (BK channels).

In a particularly preferred embodiment a compound which according to the invention selectively binds to Kv1.3, binds to the potassium channel Kv1.3 with a $K_d$ value that is at least 4000, 5000 or 10000 fold lower in comparison to the $K_d$ value with which said compound binds to the Kv1.1 channel.

In a preferred embodiment, a compound according to the invention binds to the potassium channel Kv1.3 typically with a $K_d$ value of between about 0.1 nM and about 250 nM, between about 0.5 nM and about 250 nM, between about 1 nM and about 225 nM, between about 1 nM and about 200 nM, even more preferably between about 1 nM and about 100 nM, and most preferably between about 1 nM and about 50 nM.

A compound according to the invention binds to other potassium channels, such as e.g. Kv1.1, Kv 1.2, Kv1.5, Kv1.6, IKCa1, hERG or large-conductance Ca2+-activated K+ channels (BK channels) preferably with a $K_d$ value higher than 0.1 mM, higher than 0.2 mM, higher than 0.3 mM, higher than 0.4 mM or higher than 0.5 mM. In a particularly preferred embodiment a compound according to the invention binds to the Kv1.1 channel with a $K_d$ value higher than 0.1 mM, higher than 0.2 mM, higher than 0.3 mM, higher than 0.4 mM or higher than 0.5 mM.

A compound according to the invention thus preferably binds to the potassium channel Kv1.3 with a $K_d$ value of between about 0.5 and about 200 nM such as about 1 or 2 nM and about 200 nM and to the Kv1.1 channel with a $K_d$ value higher than 0.1 mM, higher than 0.2 mM, higher than 0.3 mM, higher than 0.4 mM or higher than 0.5 mM. More preferably, a compound according to the invention binds to the potassium channel Kv1.3 with a $K_d$ value of between about 0.5 and about 100 nM such as about 1 or 2 nM and about 100 nM and to the Kv1.1 channel with a $K_d$ value higher than 0.1 mM, higher than 0.2 mM, higher than 0.3 mM, higher than 0.4 mM or higher than 0.5 mM. Even more preferably, a compound according to the invention binds to the potassium channel Kv1.3 with a $K_d$ value of between about 0.5 and about 50 nM such as about 1 or 2 nM and about 50 nM and to the Kv1.1 channel with a $K_d$ value higher than 0.5 mM.

A compound according to the invention is preferably capable of selectively binding to and blocking or reducing the activity of the potassium channel Kv1.3. A compound according to the invention may reduce the activity of the potassium channel Kv1.3 by at least 10%, at least 20%, at least 30%, at least 40%, at least 50%, at least 60%, at least 70%, more preferably at least 80%, at least 90%, at least 91%, at least 92%, at least 93%, at least 94%, at least 95%, at least 96%, at least 97%, at least 98% or at least 99% when compared to a control. In some preferred embodiments a compound according to the invention may block the activity of the the potassium channel Kv1.3 by 100%.

The ability of a compound according to the invention to selectively bind to and block or reduce the activity of the Kv1.3 channel may be tested by assays known in the art. For example, in one approach mammalian cell lines expressing Kv1.3 or another potassium channel, such as e.g. Kv1.1, Kv1.2, Kv1.5, Kv1.6, IKCa1, hERG or large-conductance Ca2+-activated K+ channels (BK channels), may be contacted with the compounds of the invention and channel currents may be measured by the patch clamp method as e.g. described in Grissmer et al. (Mol Pharmacol 45; 1227-34 (1994)) or herein below in the example section.

Each compound may e.g. be tested at different concentrations. The $K_d$ value of the compounds according to the invention may then e.g. be determined by fitting the Hill equation to the measured reduction of peak current.

It is to be understood that methods for determining the $K_d$ as described e.g. in Example 2 do not take the number of channels which are measured into account which is why for the purposes of the present disclosure the $K_d$ corresponds to the IC50 value so that the terms $K_d$ and IC50 are used synonymously herein. It is to understood that lower Kd values may be observed when completely folded and purified peptides are used vs mixtures comprising incompletely folded peptides (see Example 2).

In some embodiments a compound according to the invention may have attached to its N-terminal amino group or its C-terminal carboxy group an antibody or other molecule which is capable of recognizing and targeting a $T_{EM}$ cell.

The compounds of the present invention may be prepared using techniques known in the art. For example a peptide may be synthesized using solid phase Fmoc chemistry, e.g. according to the principles initially described by Merrifield (J. Am. Chem. Soc. 85; 7129 (1963)) as modified subsequently by Meienhofer et al. (J. Peptide Prot. Res. 13; 35 (1979)) and Fields, et al., Peptide Res. 4; 95 (1991)). Such synthesis may e.g. be carried out on automated peptide synthesizers. Once synthesized, sequences may be verified using an automated peptide sequencer.

The Potassium channels mentioned in the context of the present invention, such as e.g. the potassium channels Kv1.1, Kv 1.2, Kv1.3, Kv1.5, Kv1.6, IKCa1, hERG or large-conductance Ca2+-activated K+ channels (BK channels), are well known in the art. Therefore, the average skilled person can easily retrieve the polynucleotide and amino acid sequences of these channels and orthologous and splice isoforms thereof from any suitable public database such as e.g. the NCBI database.

In a second aspect, the present invention relates to a compound comprising or consisting of an amino acid sequence:

(SEQ ID No: 1)
$X_1-X_2-C-X_3-X_4-X_5-X_6-X_7-C-X_8-X_9-X_{10}-C-X_{11}-X_{12}-X_{13}-T-G-$
$C-P-X_{14}-X_{15}-K-C-M-N-R-K-C-X_{16}-C-X_{17}-X_{18}-C;$ wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,S,T,Q; $X_{15}$=A,G,V,I,L; $X_{16}$=K,R, $X_{17}$=Y,N,Q,T,S and $X_{18}$=G,R,K.

In a preferred embodiment, said compound is not HsTx 1 (SEQ ID NO: 32).

In a variation of the second aspect, the present invention also relates to a compound comprising or consisting of an amino acid sequence according to SEQ ID No: 1,
wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,S,T,Q; $X_{15}$=A,G,V,I,L; $X_{16}$=K,R, $X_{17}$=Y,N,Q,T,S and $X_{18}$=G,R,K; and
wherein the compound is capable of selectively binding to the potassium channel Kv1.3.

In a preferred embodiment, said compound is not HsTx 1.

In a preferred embodiment of the second aspect, the compound according to the invention comprises or consists of an amino acid sequence:

(SEQ ID No: 2)
$X_1-X_2-C-X_3-X_4-X_5-X_6-X_7-C-X_8-X_9-X_{10}-C-X_{11}-X_{12}-X_{13}-T-G-$
$C-P-X_{14}-X_{15}-K-C-M-N-R-K-X_{16}-C-X_{17}-X_{18}-C;$ wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N; $X_{15}$=A,G; $X_{16}$=K,R, $X_{17}$=Y,N and $X_{18}$=G,R; and
wherein the compound is capable of selectively binding to the potassium channel Kv1.3.

In a preferred embodiment, said compound is not HsTx 1.

In a preferred embodiment of the variation of the second aspect, the present invention also relates to a compound comprising or consisting of an amino acid sequence according to SEQ ID No: 2,
wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N; $X_{15}$=A,G; $X_{16}$=K,R, $X_{17}$=Y,N and $X_{18}$=G,R; and
wherein the compound is capable of selectively binding to the potassium channel Kv1.3.

In a preferred embodiment, said compound is not HsTx 1.

In a preferred embodiment of the second aspect, the compound according to the invention comprises or consists of an amino acid sequence:

(SEQ ID No.: 3)
$X_1-X_2-C-X_3-X_4-X_5-X_6-X_7-C-X_8-X_9-X_{10}-C-X_{11}-X_{12}-X_{13}-T-G-$
$C-P-N-A-K-C-M-N-R-K-C-X_{14}-C-X_{15}-X_{16}-C;$ wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=K,R, $X_{15}$=Y,N,Q,T,S and $X_{16}$=G,R,K.

In a preferred embodiment of the variation of the second aspect, the present invention also relates to a compound comprising or consisting of an amino acid sequence according to SEQ ID No: 3,
wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=K,R, $X_{15}$=Y,N,Q,T,S and $X_{16}$=G,R,K; and
wherein the compound is capable of selectively binding to the potassium channel Kv1.3.

In a more preferred embodiment of the second aspect, the compound according to the invention comprises or consists of an amino acid sequence:

(SEQ ID No.: 4)
$X_1-X_2-C-X_3-X_4-X_5-X_6-X_7-C-X_8-X_9-X_{10}-C-X_{11}-X_{12}-X_{13}-T-G-$
$C-P-N-A-K-C-M-N-R-K-C-X_{14}-C-X_{15}-X_{16}-C;$ wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=K,R, $X_{15}$=Y,N and $X_{16}$=G,R.

In a more preferred embodiment of the variation of the second aspect, the present invention also relates to a compound comprising or consisting of an amino acid sequence according to SEQ ID No: 4,
wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=K,R, $X_{15}$=Y,N and $X_{16}$=G,R; and
wherein the compound is capable of selectively binding to the potassium channel Kv1.3.

In another preferred embodiment of the second aspect, the compound according to the invention comprises or consists of an amino acid sequence:

(SEQ ID No.: 5)
$X_1$-$X_2$-C-$X_3$-$X_4$-$X_5$-$X_6$-$X_7$-C-$X_8$-$X_9$-$X_{10}$-C-$X_{11}$-$X_{12}$-$X_{13}$-T-G-

C-P-$X_{14}$-$X_{15}$-K-C-M-N-R-K-C-$X_{16}$-C-Y-G-C;

wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,S,T,Q; $X_{15}$=A,G,V,I,L and $X_{16}$=K,R.

In another preferred embodiment of the variation of the second aspect, the present invention also relates to a compound comprising or consisting of an amino acid sequence according to SEQ ID No: 5,
wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,S,T,Q; $X_{15}$=A,G,V,I,L and $X_{16}$=K,R; and
wherein the compound is capable of selectively binding to the potassium channel Kv1.3.

In a more preferred embodiment of the second aspect, the compound according to the invention comprises or consists of an amino acid sequence:

(SEQ ID No.: 6)
$X_1$-$X_2$-C-$X_3$-$X_4$-$X_5$-$X_6$-$X_7$-C-$X_8$-$X_9$-$X_{10}$-C-$X_{11}$-$X_{12}$-$X_{13}$-T-G-

C-P-$X_{14}$-$X_{15}$-K-C-M-N-R-K-C-$X_{16}$-C-Y-G-C;

wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N; $X_{15}$=A,G and $X_{16}$=K,R.

In a more preferred embodiment of the variation of the second aspect, the present invention also relates to a compound comprising or consisting of an amino acid sequence according to SEQ ID No: 6,
wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N; $X_{15}$=A,G and $X_{16}$=K,R; and
wherein the compound is capable of selectively binding to the potassium channel Kv1.3.

In another preferred embodiment of the second aspect, the compound according to the invention comprises or consists of an amino acid sequence:

(SEQ ID No.: 7)
$X_1$-$X_2$-C-$X_3$-$X_4$-$X_5$-$X_6$-$X_7$-C-$X_8$-$X_9$-$X_{10}$-C-$X_{11}$-$X_{12}$-$X_{13}$-T-G-

C-P-N-A-K-C-M-N-R-K-C-$X_{14}$-C-Y-G-C;

wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I and $X_{14}$=K,R.

In another preferred embodiment of the variation of the second aspect, the present invention also relates to a compound comprising or consisting of an amino acid sequence according to SEQ ID No: 7,
wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I and $X_{14}$=K,R; and
wherein the compound is capable of selectively binding to the potassium channel Kv1.3.

In a more preferred embodiment of the second aspect, the compound according to the invention comprises or consists of an amino acid sequence:

(SEQ ID No.: 8)
$X_1$-$X_2$-C-$X_3$-$X_4$-$X_5$-$X_6$-$X_7$-C-$X_8$-$X_9$-$X_{10}$-C-$X_{11}$-$X_{12}$-$X_{13}$-T-G-

C-P-N-A-K-C-M-N-R-K-C-$X_{14}$-C-Y-G-C;

wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L and $X_{14}$=K,R.

In a more preferred embodiment of the variation of the second aspect, the present invention also relates to a compound comprising or consisting of an amino acid sequence according to SEQ ID No: 8,
wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L and $X_{14}$=K,R; and
wherein the compound is capable of selectively binding to the potassium channel Kv1.3.

In an even more preferred embodiment of the second aspect, the compound according to the invention comprises or consists of an amino acid sequence according to SEQ ID No.: 9 (cgtx 538).

In another preferred embodiment of the second aspect, the compound according to the invention comprises or consists of an amino acid sequence:

(SEQ ID No.: 10)
$X_1$-$X_2$-C-$X_3$-$X_4$-$X_5$-$X_6$-Q-C-$X_7$-R-$X_8$-C-$X_9$-$X_{10}$-Q-T-G-C-P-Y-

G-K-C-M-N-R-K-C-K-C-N-R-C;

wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=A,Y,I,L,W,S,T,V,L,F; $X_8$=P,H,V,I,L,A; $X_9$=R,K,Q,N and $X_{10}$=K,D,A,R,E,V,L,I.

In another preferred embodiment of the variation of the second aspect, the present invention also relates to a compound comprising or consisting of an amino acid sequence according to SEQ ID No: 10,
wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=A,Y,I,L,W,S,T,V,L,F; $X_8$=P,H,V,I,L,A; $X_9$=R,K,Q,N and $X_{10}$=K,D,A,R,E,V,L,I; and wherein the compound is capable of selectively binding to the potassium channel Kv1.3.

In a more preferred embodiment of the second aspect, the compound according to the invention comprises or consists of an amino acid sequence:

(SEQ ID No.: 11)
$X_1$-$X_2$-C-$X_3$-$X_4$-$X_5$-$X_6$-Q-C-$X_7$-R-$X_8$-C-$X_9$-$X_{10}$-Q-T-G-C-P-Y-G-K-C-M-N-R-K-C-K-C-N-R-C;

wherein $X_1$=A,V,I; $X_2$=S,R,K; $X_3$=R,T,K; $X_4$=T,G,S,N,I; $X_5$=P,S; $X_6$=R,K,P; $X_7$=A,Y,I,L,W; $X_8$=P,H,V,I,L,A; $X_9$=R,K,Q,N and $X_{10}$=K,D,A,R,E,V,L,I.

In a more preferred embodiment of the variation of the second aspect, the present invention also relates to a compound comprising or consisting of an amino acid sequence according to SEQ ID No: 11,
wherein $X_1$=A,V,I; $X_2$=S,R,K; $X_3$=R,T,K; $X_4$=T,G,S,N,I; $X_5$=P,S; $X_6$=R,K,P; $X_7$=A,Y,I,L,W; $X_8$=P,H,V,I,L,A; $X_9$=R,K,Q,N and $X_{10}$=K,D,A,R,E,V,L,I; and
wherein the compound is capable of selectively binding to the potassium channel Kv1.3.

In an even more preferred embodiment of the second aspect, the compound according to the invention comprises or consists of an amino acid sequence according to SEQ ID No.12 (cgtx 539).

In another preferred embodiment of the second aspect, the compound according to the invention comprises or consists of an amino acid sequence:

(SEQ ID No: 13)
$X_1$-$X_2$-C-R-$X_3$-$X_4$-$X_5$-Q-C-Y-P-H-C-$X_6$-$X_7$-$X_8$-T-G-C-P-Y-G-K-C-M-N-R-K-C-K-C-N-R-C;

wherein $X_1$=A,V,I,L; $X_2$=S,R,K,T,Y; $X_3$=T,G,S,N,I,K,Q,A,V,L,Y; $X_4$=P,S,T; $X_5$=R,K,P; $X_6$=R,K,Q,N; $X_7$=K,D,A,R,E,V,L,I and $X_8$=E,Q,A,L,D,N,V,I.

In another preferred embodiment of the variation of the second aspect, the present invention also relates to a compound comprising or consisting of an amino acid sequence according to SEQ ID No: 13,
wherein $X_1$=A,V,I,L; $X_2$=S,R,K,T,Y; $X_3$=T,G,S,N,I,K,Q,A,V,L,Y; $X_4$=P,S,T; $X_5$=R,K,P; $X_6$=R,K,Q,N; $X_7$=K,D,A,R,E,V,L,I and $X_8$=E,Q,A,L,D,N,V,I; and
wherein the compound is capable of selectively binding to the potassium channel Kv1.3.

In a more preferred embodiment of the second aspect, the compound according to the invention comprises or consists of an amino acid sequence:

(SEQ ID No.: 14)
$X_1$-$X_2$-C-R-$X_3$-$X_4$-$X_5$-Q-C-Y-P-H-C-$X_6$-$X_7$-$X_8$-T-G-C-P-Y-G-K-C-M-N-R-K-C-K-C-N-R-C;

wherein $X_1$=A,V,I; $X_2$=S,R,K; $X_3$=T,G,S,N,I; $X_4$=P,S,T; $X_5$=R,K,P; $X_6$=R,K,Q; $X_7$=K,D,A,R and $X_8$=E,Q,A,L; and
wherein the compound is capable of selectively binding to the potassium channel Kv1.3.

In a more preferred embodiment of the variation of the second aspect, the present invention also relates to a compound comprising or consisting of an amino acid sequence according to SEQ ID No: 14,
wherein $X_1$=A,V,I; $X_2$=S,R,K; $X_3$=T,G,S,N,I; $X_4$=P,S,T; $X_5$=R,K,P; $X_6$=R,K,Q; $X_7$=K,D,A,R and $X_8$=E,Q,A,L; and
wherein the compound is capable of selectively binding to the potassium channel Kv1.3.

In an even more preferred embodiment of the second aspect the compound according to the invention comprises an amino acid sequence according to SEQ ID No.15 (cgtx 540).

In another preferred embodiment of the second aspect, the compound according to the invention comprises or consists of an amino acid sequence:

(SEQ ID No.: 16)
$X_1$-$X_2$-C-$X_3$-$X_4$-$X_5$-$X_6$-$X_7$-C-$X_8$-$X_9$-$X_{10}$-C-$X_{11}$-$X_{12}$-$X_{13}$-T-G-C-P-Y-G-K-C-M-N-R-K-C-R-C-$X_{14}$-$X_{15}$-C;

wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,Q,T,S and $X_{15}$=G,R,K.

In another preferred embodiment of the variation of the second aspect, the present invention also relates to a compound comprising or consisting of an amino acid sequence according to SEQ ID No: 16,
wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,Q,T,S and $X_{15}$=G,R,K; and
wherein the compound is capable of selectively binding to the potassium channel Kv1.3.

In a more preferred embodiment of the second aspect, the compound according to the invention comprises or consists of an amino acid sequence:

(SEQ ID No.: 17)
$X_1$-$X_2$-C-$X_3$-$X_4$-$X_5$-$X_6$-$X_7$-C-$X_8$-$X_9$-$X_{10}$-C-$X_{11}$-$X_{12}$-$X_{13}$-T-G-C-P-Y-G-K-C-M-N-R-K-C-R-C-$X_{14}$-$X_{15}$-C;

wherein $X_1$=A,V,I; $X_2$=S,R,K; $X_3$=R,T,K; $X_4$=T,G,S,N,I; $X_5$=P,S,T; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N and $X_{15}$=G,R.

In a more preferred embodiment of the variation of the second aspect, the present invention also relates to a compound comprising or consisting of an amino acid sequence according to SEQ ID No: 17,
wherein $X_1$=A,V,I; $X_2$=S,R,K; $X_3$=R,T,K; $X_4$=T,G,S,N,I; $X_5$=P,S,T; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N and $X_{15}$=G,R; and
wherein the compound is capable of selectively binding to the potassium channel Kv1.3.

In an even more particularly preferred embodiment of the second aspect, the compound according to the invention comprises or consists of an amino acid sequence according to SEQ ID No.18 (cgtx 541) or SEQ ID No.19 (cgtx 542).

In another preferred embodiment of the second aspect, the compound according to the invention comprises or consists of an amino acid sequence:

(SEQ ID No.: 20)
I-S-C-$X_1$-$X_2$-$X_3$-$X_4$-$X_5$-C-$X_6$-$X_7$-$X_8$-C-$X_9$-$X_{10}$-$X_{11}$-T-G-C-P-Y-G-K-C-M-N-R-K-C-K-C-N-R-C;

wherein $X_1$=R,T,K,S,Y; $X_2$=T,G,S,N,I,K,Q,A,V,L,Y; $X_3$=P,S,T; $X_4$=R,K,P; $X_5$=D,Q,N,E; $X_6$=A,Y,I,L,W,S,T,V,L,F; $X_7$=D,R,P,K,E,S,T,Y; $X_8$=P,H,V,I,L,A; $X_9$=R,K,Q,N; $X_{10}$=K,D,A,R,E,V,L,I and $X_{11}$=E,Q,A,L,D,N,V,I.

In another preferred embodiment of the variation of the second aspect, the present invention also relates to a compound comprising or consisting of an amino acid sequence according to SEQ ID No: 20,
wherein $X_1$=R,T,K,S,Y; $X_2$=T,G,S,N,I,K,Q,A,V,L,Y; $X_3$=P,S,T; $X_4$=R,K,P; $X_5$=D,Q,N,E; $X_6$=A,Y,I,L,W,S,T,V,L,F; $X_7$=D,R,P,K,E,S,T,Y; $X_8$=P,H,V,I,L,A; $X_9$=R,K,Q,N; $X_{10}$=K,D,A,R,E,V,L,I and $X_{11}$=E,Q,A,L,D,N,V,I; and
wherein the compound is capable of selectively binding to the potassium channel Kv1.3.

In a more preferred embodiment of the second aspect, the compound according to the invention comprises or consists of an amino acid sequence:

(SEQ ID No.: 21)
I-S-C-$X_1$-$X_2$-$X_3$-$X_4$-$X_5$-C-$X_6$-$X_7$-$X_8$-C-$X_9$-$X_{10}$-$X_{11}$-T-G-C-P-Y-G-K-C-M-N-R-K-C-K-C-N-R-C;

wherein $X_1$=R,T,K; $X_2$=T,G,S,N,I; $X_3$=P,S; $X_4$=R,K,P; $X_5$=D,Q,N,E; $X_6$=A,Y,I,L,W; $X_7$=D,R,P,K,E,S; $X_8$=P,H,V; $X_9$=R,K,Q; $X_{10}$=K,D,A,R and $X_{11}$=E,Q,A,L.

In a more preferred embodiment of the variation of the second aspect, the present invention also relates to a compound comprising or consisting of an amino acid sequence according to SEQ ID No: 21,
wherein $X_1$=R,T,K; $X_2$=T,G,S,N,I; $X_3$=P,S; $X_4$=R,K,P; $X_5$=D,Q,N,E; $X_6$=A,Y,I,L,W; $X_7$=D,R,P,K,E,S; $X_8$=P,H,V; $X_9$=R,K,Q; $X_{10}$=K,D,A,R and $X_{11}$=E,Q,A,L; and
wherein the compound is capable of selectively binding to the potassium channel Kv1.3.

In an even more preferred embodiment of the second aspect, the compound according to the invention comprises or consists of an amino acid sequence according to SEQ ID No.22 (cgtx 545).

In a third aspect, the compound according to the invention comprises or consists of an amino acid sequence:

(SEQ ID No.: 27)
G-V-$X_1$-I-N-V-$X_2$-C-$X_3$-$X_4$-$X_5$-$X_6$-$X_7$-C-$X_8$-$X_9$-$X_{10}$-C-$X_{11}$-$X_{12}$-$X_{13}$-T-G-C-P-$X_{14}$-$X_{15}$-K-C-M-N-R-K-C-$X_{16}$-C-$X_{17}$-$X_{18}$-C;

wherein $X_1$=P,I,F,V,A,L,W; $X_2$=K,S,T,Y,R; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,S,T,Q; $X_{15}$=A,G,V,I,L; $X_{16}$=K,R, $X_{17}$=Y,N,Q,T,S and $X_{18}$=G,R,K.

In a variation of the third aspect, the present invention also relates to a compound comprising or consisting of an amino acid sequence according to SEQ ID No: 27,
wherein $X_1$=P,I,F,V,A,L,W; $X_2$=K,S,T,Y,R; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,S,T,Q; $X_{15}$=A,G,V,I,L; $X_{16}$=K,R, $X_{17}$=Y,N,Q,T,S and $X_{18}$=G,R,K; and
wherein the compound is capable of selectively binding to the potassium channel Kv1.3.

In a preferred embodiment of the third aspect, the compound according to the invention comprises or consists of an amino acid sequence:

(SEQ ID No.: 28)
G-V-$X_1$-I-N-V-$X_2$-C-$X_3$-$X_4$-$X_5$-$X_6$-$X_7$-C-$X_8$-$X_9$-$X_{10}$-C-$X_{11}$-$X_{12}$-$X_{13}$-T-G-C-P-$X_{14}$-$X_{15}$-K-C-M-N-R-K-C-$X_{16}$-C-$X_{17}$-$X_{18}$-C;

wherein $X_1$=P,I,F; $X_2$=K,S; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N; $X_{15}$=A,G; $X_{16}$=K,R, $X_{17}$=Y,N and $X_{18}$=G,R.

In a preferred embodiment of the variation of the third aspect, the present invention also relates to a compound comprising or consisting of an amino acid sequence according to SEQ ID No: 28,
wherein $X_1$=P,I,F; $X_2$=K,S; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N; $X_{15}$=A,G; $X_{16}$=K,R, $X_{17}$=Y,N and $X_{18}$=G,R; and
wherein the compound is capable of selectively binding to the potassium channel Kv1.3.

In a particularly preferred embodiment of the third aspect, the compound according to the invention comprises or consists of an amino acid sequence according of SEQ ID No.29 (cgtx 543), SEQ ID No.30 (cgtx 546) or SEQ ID No.31 (cgtx 548).

Thus, it is particularly preferred that the compound according to the invention comprises or consists of an amino acid sequence according to SEQ ID NO. 9, 12, 15, 18, 19, 22, 25, 26, 29, 30 or 31 and a compound which comprises or consists of an amino acid sequence according to SEQ ID NO. 25 is most preferred.

In some embodiments, the aforementioned compounds comprising or consisting of an amino acid sequence according to SEQ ID NO. 9, 12, 15, 18, 19, 22, 25, 26, 29, 30 or 31 may comprise between 0 and 5, i.e. 0, 1, 2, 3, 4 or 5 amino acid substitutions, deletions or insertions, provided that the compounds are still capable of selectively binding to and/or blocking or reducing the activity of the Kv1.3 potassium channel. Compounds with such amino acid mutations are called variants and also form part of the invention.

A substitution may be a conservative or a non-conservative substitution, preferably the substitution is a conservative substitution. A conservative substitution comprises the substitution of an amino acid with another amino acid having a chemical property similar to the amino acid that is substituted. In some embodiments, a substitution may also be an exchange of a naturally occurring amino acid with a non natural amino acid.

The terms "amino acid deletion" and "amino acid insertion" are used herein according to their conventional and well known meaning in the art.

The present invention in another aspect also provides a nucleic acid encoding for an amino acid sequence according to the invention.

In the context of the present invention the terms "nucleic acid" or "nucleic acid sequence" refer to a naturally occurring or synthetic deoxyribonucleotide or ribonucleotide polymer in either single- or double-stranded form which is capable of encoding a given amino acid sequence. The term also encompasses derivatives of a given deoxyribonucleotide or ribonucleotide polymer that may differ from the original deoxyribonucleotide or ribonucleotide polymer in that one or more nucleotides of the original sequence are substituted by other nucleotides and/or (chemically) modified by methods known to the skilled person, provided that the deoxyribonucleotide or ribonucleotide polymer is still capable of encoding its respective amino acid sequence.

It will be apparent to the skilled person that due to the degeneracy of the genetic code a given amino acid sequence according to the invention may be encoded by different nucleotide sequences.

The present invention in a further aspect also provides a vector comprising a nucleic acid sequence according to the invention.

The vector may be any molecular vehicle such as e.g. a plasmid vector, a virus vector, a bacteriophage vector or any other vehicle, which contains one or more nucleotide sequences according to the invention and is preferably designed for transfer between different host cells. In a preferred embodiment, the vector is a prokaryotic or eukaryotic expression vector.

The term "expression vector" as used herein refers to a vector that contains a desired coding sequence and appropriate DNA sequences necessary for the expression of the operably linked coding sequence and is capable of inducing protein expression in a particular host organism (e.g., bacteria, yeast, plant, insect, or mammal) or in in vitro expression systems. Expression vectors may comprise functional elements such as e.g., a promoter that is operatively linked to the nucleic acid sequence to be transcribed, a termination sequence that allows proper termination of transcription and a selectable marker. The person skilled in the art will be aware that the nature of the promoter will depend on whether the vector is going to be used in a prokaryotic or eukaryotic host cell. To obtain stable expression for an extended period of time the expression vector may further comprise an origin of replication (ORI). Suitable expression vectors are known to the person skilled in the art. Depending on whether expression is to be achieved in a prokaryotic or eukaryotic host cell or in in vitro expression systems, the vectors may be prokaryotic and/or eukaryotic expression vectors such as plasmids, cosmids, minichromosomes, bacterial phages, retroviral vectors etc. The skilled person will be familiar with how to select an appropriate vector according to the specific need.

The present invention in another aspect refers to a host cell comprising a nucleic acid sequence or a vector according to the invention.

Depending on the area of applications, the host cell may be a prokaryotic or eukaryotic host cell. Typical prokaryotic host cells include bacterial cells such as e.g. *Escherichia coli* (*E. coli*). Typical eukaryotic host cells include e.g. yeast cells such as e.g. *Saccharomyces cerevisiae*, insect cells such as e.g. Sf9/Sf21 cells, plant cells and mammalian cells such as e.g. COS, CHO and HeLa cells.

The present invention in a further aspect also relates to a pharmaceutical composition comprising a compound according to the invention.

In some embodiments, a pharmaceutical composition according to the invention may comprise more than one of the compounds according to the invention. For example, a pharmaceutical composition according to the invention may comprise 2, 3, 4, 5, 6, 7, 8, 9, 10 or more than 10 of the compounds according to the invention. In some preferred embodiments a pharmaceutical composition of the invention may comprise one or more compounds according to the invention, wherein the compounds are selected from the group of compounds comprising or consisting of an amino acid sequence of SEQ ID NO. 9, 12, 15, 18, 19, 22, 25, 26, 29, 30 or 31.

Peptides that are considered to be particularly preferred throughout the present disclosure for therapeutic use are peptides of SEQ ID No.: 25 (cgtx-544), SEQ ID No.: 29 (cgtx 543), and SEQ ID No.: 9 (cgtx 538). It is noted that most of the experiments described hereinafter have been performed using peptides of SEQ ID No.: 25 (cgtx-544). However, peptides of SEQ ID No.: 29 (cgtx 543), and SEQ ID No.: 9 (cgtx 538) have also been tested for their selectivity vs hERG and, based on their sequence similarity it seems thus reasonable to conclude that similar effects as for ctgx 544 may be observed for these peptides as well.

These peptides as well as other peptides described herein may be manufactured by methods known in the art such as solid phase synthesis. It is noted that these peptides comprise cysteine residues and may thus require active folding into a native state for achieving optimal activity. Activity may be further enhanced by purifying completely folded peptides.

Folding may be achieved by subjecting the synthesized peptides to oxidation to achieve disulfide bridges between cysteine residues. This may be done by incubating the peptides in e.g. phosphate buffer at pH of ~8.0 in the presence of atmospheric oxygen as is described in Example 8. Folding may be followed by mass spectrometry as the folded peptide will show a slightly reduced mass corresponding to the loss of hydrogen atoms during disulfide bridge formation. In the case of ctgx 544 the difference in mass would be 4212 vs. 4220.2 Da.

Purification of completely folded peptides can be achieved by methods known in the art such as HPLC purification. A suitable approach is described in Example 8.

A pharmaceutical composition according to the invention can be administered orally, for example in the form of inhalable powder pills, tablets, lacquered tablets, sugar-coated tablets, granules, hard and soft gelatin capsules, aqueous, alcoholic or oily solutions, syrups, emulsions or suspensions, or rectally, for example in the form of suppositories.

Administration can also be carried out intranasally or sublingually.

Administration can further be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures.

Forms of administration that are considered to be particularly preferred throughout the present disclosure are intravenous, intramuscular, or subcutaneous administration.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc.

The pharmaceutical compositions can also contain additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Examples of suitable excipients for the various different forms of pharmaceutical compositions described herein may be found in the "Handbook of Pharmaceutical Excipients", 2nd Edition, (1994), Edited by A Wade and P J Weller.

In some embodiments the pharmaceutical compositions may be sustained release formulations.

In some embodiments a pharmaceutical composition according to the invention in addition to the at least one compound according to the invention may further comprise other immunosuppressive agents which are suitable for the treatment of autoimmune diseases. Examples of such immunosuppressive agents include e.g. cortisol, hydrocortisol, dexamethasone, cyclophosphamide, nitrosoureas, methotrexate, mercaptopurine, mitomycin C, bleomycin, mithramycin, cyclosporine, rapamycin, azathioprine, prednisone and deoxyspergualin and interferons.

In other preferred embodiments separate compositions comprising the aforementioned further immunosuppressive agents may be administered to a mammal in need thereof in combination with a pharmaceutical composition comprising one or more compounds according to the invention.

In a further aspect the present invention relates to a compound according to the invention or a pharmaceutical composition according to the invention for use in the treatment or prevention of a disease involving effector memory cells ($T_{EM}$-cells).

The present invention preferably relates to a compound according to the invention or a pharmaceutical composition according to the invention for use in the treatment of a disease selected from the group consisting of an autoimmune disease, obesity, parodontitis and/or tissue transplant rejection.

For the purposes of the present disclosure the term "treatment" refers to the curative alleviation of a disease while the term "prevention" refers to preventive prophylaxis. It is to be understood that both terms do not imply a complete remission or prevention of the respective disease but rather that there is an improvement compared to a situation where no pharmaceutically active agent is administered for either curative or preventive purposes.

In a particularly preferred embodiment the present invention relates to the use of a compound according to the invention or a pharmaceutical composition according to the invention for use in the treatment or prevention of an autoimmune disease.

In the context of the present invention the term "auto immune disease" or "auto immune diseases" refers to a disease state caused by an inappropriate immune response that is directed to a self-encoded entity, i.e. an autoantigen. Encompassed within the definition are any of a number of disorders caused by an immune system defect that allows the body to attack its own tissues. In a preferred embodiment, the auto immune disease is a T cell mediated autoimmune disorder.

Examples of auto immune diseases that may be treated or prevented by the compounds and pharmaceutical compositions of the present invention include e.g. multiple sclerosis, rheumatoid arthritis, psoriasis, type-1 diabetes, vasculitis, Hashimoto's disease, asthma, atopic dermatitis, autoimmune eye diseases, Sjögren's syndrome, acute disseminated encephalomyelitis (ADEM), Addison's disease, ankylosing spondylitis, antiphospholipid antibody syndrome (APS), aplastic anaemia, autoimmune hepatitis, autoimmune oophoritis, Coeliac disease, Crohn's disease, gestational pemphigoid, Goodpasture's syndrome, Grave's disease, Guillian-Barre syndrome, idiopathic thrombocytopenic purpura, Kawasaki's disease, lupus erythematosus, myasthenia gravis, opsoclonus myoclonus syndrome, optic neuritis, Ord's thyroiditis, pemphigus, pernicious anaemia, polyarthritis (in dogs), primary biliary cirrhosis, Reiter's syndrome, Takayasu's arteritis, temporal arteritis, warm autoimmune haemolytic anaemia, Wegener's granulomatosis, ANCA-associated systemic vasculitis, Churg-Strauss syndrome, microscopic polyangiitis, colitis, inflammatory bowel diseases, uveitis and psoriatic arthritis.

Some of these auto-immune diseases have been linked to $T_{EM}$-cells for example ANCA-associated systemic vasculitis (Abdulahad, *Nephrology,* 2009 vol. 14 pp 26), Churg-Strauss syndrome, Wegener's granulomatosis, microscopic polyangiitis (Berden, *Arthritis & Rheumatism,* 2009, vol. 60, pp 1578), Ankylosing spondylitis, Behçet'disease, colitis, Crohn's disease, Inflammatory Bowel Diseases, multiple sclerosis, psoriasis, rheumatoid Arthritis, Sjögren's Syndrome, Type 1 Diabetes Mellitus (Ulivieri, *Expert Rev. Vaccines,* 2013 vol. 12 pp 297), System lupus erythematosus (Devarajan, *Immunol. Res,* 2013 vol. 57 pp 12), uveitis (Amadi-Obi, *Nephrology,* 2009, vol 14 pp 26), and psoriatic arthritis (De Vlam, *Acta Derm. Venereol,* 2014, vol. 94, pp 627).

The same applies to obesity (Xu, *Human Molecular Genetics,* 2003, vol. 12, pp 551).

Given that ctgx544 has been shown to selectively act on $T_{EM}$-cells and to have effects on rheumatoid arthritis it seems reasonable to assume that cgtx544 and the other peptides disclosed herein can be used to treat or prevent such diseases.

In a preferred embodiment the auto immune disease to be treated or prevented by the compounds and pharmaceutical compositions of the present invention is selected from the group consisting of multiple sclerosis, rheumatoid arthritis, psoriasis, type-1 diabetes and vasculitis.

Transplantation of organs or tissues into a new host often may cause rejection of the transplanted organ or tissue due to a T cell mediated immune response against the new organ or tissue (for example heart, liver, kidney, pancreas or skin). The present invention therefore also relates to a compound according to the invention or a pharmaceutical composition according to the invention for use in the treatment or prevention of organ or tissue transplant rejection. Organ transplant rejection has also been shown to involve $T_{EM}$-cells (see e.g. Macedo, *Transplantation,* 2012 vol 93 pp 813). Given the high selectivity of cgtx544 and the other peptides disclosed herein it seems reasonable to assume that cgtx544 and the other peptides disclosed herein can be used to treat or prevent such diseases.

In another aspect the present invention relates to a method of treating or preventing an auto immune disease, obesity, parodontitis and/or tissue transplant rejection in a mammal by administering a compound according to the invention or a pharmaceutical composition according to the invention to a mammal in need thereof.

Preferably the auto immune disease is selected from the group consisting of multiple sclerosis, rheumatoid arthritis, psoriasis, type-1 diabetes and vasculitis.

The term "mammal" as used herein includes e.g. humans, non-human primates, mice, rats, rabbits, guinea pigs, dogs, cats, cattle, horses, sheep, pigs, goats and the like. The preferred mammal is human.

A unit dosage form of a pharmaceutical composition according to the invention may contain any suitable effective amount of a compound according to the invention commensurate with the intended daily dosage range to be employed.

A mammal in need of administration of a compound according to the invention or a pharmaceutical composition according to the invention is e.g. a mammal suffering from or being at risk of developing a T cell mediated disease, preferably a T cell mediated auto immune disease. In a preferred embodiment said auto immune disease is selected from the group consisting of multiple sclerosis, rheumatoid arthritis, psoriasis, type-1 diabetes and vasculitis.

The present invention in a further aspect also relates to a method of manufacturing a compound according to the invention, a nucleic acid sequence according to the invention, a vector according to the invention or a pharmaceutical composition according to the invention.

The present invention also relates to:

(1) A compound comprising an amino acid sequence:

(SEQ ID No.: 1)
$X_1-X_2-C-X_3-X_4-X_5-X_6-X_7-C-X_8-X_9-X_{10}-C-X_{11}-X_{12}-X_{13}-T-G-C-$
$P-X_{14}-X_{15}-K-C-M-N-R-K-C-X_{16}-C-X_{17}-X_{18}-C;$ wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,S,T,Q; $X_{15}$=A,G,V,I,L; $X_{16}$=K,R, $X_{17}$=Y,N,Q,T,S and $X_{18}$=G,R,K.

In a preferred embodiment, said compound is not HsTx 1 (SEQ ID No.: 32)

(2) A compound according to (1) comprising an amino acid sequence:

(SEQ ID No.: 2)
$X_1-X_2-C-X_3-X_4-X_5-X_6-X_7-C-X_8-X_9-X_{10}-C-X_{11}-X_{12}-X_{13}-T-G-C-$
$P-X_{14}-X_{15}-K-C-M-N-R-K-C-X_{16}-C-X_{17}-X_{18}-C;$ wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N; $X_{15}$=A,G; $X_{16}$=K,R, $X_{17}$=Y,N and $X_{18}$=G,R.

In a preferred embodiment, said compound is not HsTx 1.

(3) A compound according to (1) comprising an amino acid sequence:

(SEQ ID No.: 3)
$X_1-X_2-C-X_3-X_4-X_5-X_6-X_7-C-X_8-X_9-X_{10}-C-X_{11}-X_{12}-X_{13}-T-G-C-$
$P-N-A-K-C-M-N-R-K-C-X_{14}-C-X_{15}-X_{16}-C;$

Wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=K,R, $X_{15}$=Y,N,Q,T,S and $X_{16}$=G,R,K.

(4) A compound according to (3) comprising an amino sequence:

(SEQ ID No.: 4)
$X_1-X_2-C-X_3-X_4-X_5-X_6-X_7-C-X_8-X_9-X_{10}-C-X_{11}-X_{12}-X_{13}-T-G-C-$
$P-N-A-K-C-M-N-R-K-C-X_{14}-C-X_{15}-X_{16}-C;$ wherein $X_1$=A,V,I $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=K,R, $X_{15}$=Y,N and $X_{16}$=G,R.

(5) A compound according to (1) comprising an amino acid sequence:

(SEQ ID No.: 5)
$X_1-X_2-C-X_3-X_4-X_5-X_6-X_7-C-X_8-X_9-X_{10}-C-X_{11}-X_{12}-X_{13}-T-G-C-$
$P-X_{14}-X_{15}-K-C-M-N-R-K-C-X_{16}-C-Y-G-C;$ wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,S,T,Q; $X_{15}$=A,G,V,I,L and $X_{16}$=K,R.

(6) A compound according to (5) comprising an amino acid sequence:

(SEQ ID No.: 6)
$X_1-X_2-C-X_3-X_4-X_5-X_6-X_7-C-X_8-X_9-X_{10}-C-X_{11}-X_{12}-X_{13}-T-G-C-$
$P-X_{14}-X_{15}-K-C-M-N-R-K-C-X_{16}-C-Y-G-C;$ wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N; $X_{15}$=A,G and $X_{16}$=K,R.

(7) A compound according to (1) comprising an amino acid sequence:

(SEQ ID No.: 7)
$X_1-X_2-C-X_3-X_4-X_5-X_6-X_7-C-X_8-X_9-X_{10}-C-X_{11}-X_{12}-X_{13}-T-G-C-$
$P-N-A-K-C-M-N-R-K-C-X_{14}-C-Y-G-C;$ wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I and $X_{14}$=K,R.

(8) A compound according to (7) comprising an amino acid sequence:

(SEQ ID No.: 8)
$X_1-X_2-C-X_3-X_4-X_5-X_6-X_7-C-X_8-X_9-X_{10}-C-X_{11}-X_{12}-X_{13}-T-G-C-$
$P-N-A-K-C-M-N-R-K-C-X_{14}-C-Y-G-C;$ wherein $X_1$=A,V,I; $X_2$=S,R,K; $X_3$=R,T,K; $X_4$=T,G,S,N,I; $X_5$=P,S; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L and $X_{14}$=K,R.

(9) A compound according to (8) comprising an amino sequence of SEQ ID No. 9.

(10) A compound according to (1) comprising an amino acid sequence:

(SEQ ID No.: 10)
$X_1-X_2-C-X_3-X_4-X_5-X_6-Q-C-X_7-R-X_8-C-X_9-X_{10}-Q-T-G-C-P-Y-$
$G-K-C-M-N-R-K-C-K-C-N-R-C;$ wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=A,Y,I,L,W,S,T,V,L,F; $X_8$=P,H,V,I,L,A; $X_9$=R,K,Q,N and $X_{10}$=K,D,A,R,E,V,L,I.

(11) A compound according to (10) comprising an amino acid sequence:

(SEQ ID No.: 11)
$X_1-X_2-C-X_3-X_4-X_5-X_6-Q-C-X_7-R-X_8-C-X_9-X_{10}-Q-T-G-C-P-Y-$
$G-K-C-M-N-R-K-C-K-C-N-R-C;$ wherein $X_1$=A,V,I; $X_2$=S,R,K; $X_3$=R,T,K; $X_4$=T,G,S,N,I; $X_5$=P,S; $X_6$=R,K,P; $X_7$=A,Y,I,L,W; $X_8$=P,H,V,I,L,A; $X_9$=R,K,Q,N and $X_{10}$=K,D,A,R,E,V,L,I.

(12) A compound according to (11) comprising an amino acid sequence of SEQ ID No. 12.

(13) A compound according to (1) comprising an amino acid sequence:

(SEQ ID No.: 13)
$X_1-X_2-C-R-X_3-X_4-X_5-Q-C-Y-P-H-C-X_6-X_7-X_8-T-G-C-P-Y-$
$G-K-C-M-N-R-K-C-K-C-N-R-C;$ wherein $X_1$=A,V,I,L; $X_2$=S,R,K,T,Y; $X_3$=T,G,S,N,I,K,Q,A,V,L,Y; $X_4$=P,S,T; $X_5$=R,K,P; $X_6$=R,K,Q,N; $X_7$=K,D,A,R,E,V,L,I and $X_8$=E,Q,A,L,D,N,V,I.

(14) A compound according to (13) comprising an amino acid sequence:

(SEQ ID No.: 14)
$X_1-X_2-C-R-X_3-X_4-X_5-Q-C-Y-P-H-C-X_6-X_7-X_8-T-G-C-P-Y-G-$
$K-C-M-N-R-K-C-K-C-N-R-C;$ wherein $X_1$=A,V,I; $X_2$=S,R,K; $X_3$=T,G,S,N,I; $X_4$=P,S,T; $X_5$=R,K,P; $X_6$=R,K,Q; $X_7$=K,D,A,R and $X_8$=E,Q,A,L.

(15) A compound according to (14) comprising an amino acid sequence of SEQ ID No. 15.

(16) A compound according to (1) comprising an amino acid sequence:

(SEQ ID No.: 16)
$X_1-X_2-C-X_3-X_4-X_5-X_6-X_7-C-X_8-X_9-X_{10}-C-X_{11}-X_{12}-X_{13}-T-G-$
$C-P-Y-G-K-C-M-N-R-K-C-R-C-X_{14}-X_{15}-C;$ wherein $X_1$=A,V,I,L; $X_2$=S,R,K,T,Y; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,Q,T,S and $X_{15}$=G,R,K.

(17) A compound according to (16) comprising an amino acid sequence:

(SEQ ID No.: 17)
$X_1-X_2-C-X_3-X_4-X_5-X_6-X_7-C-X_8-X_9-X_{10}-C-X_{11}-X_{12}-X_{13}-T-G-C-$
$P-Y-G-K-C-M-N-R-K-C-R-C-X_{14}-X_{15}-C;$

Wherein $X_1$=A,V,I; $X_2$=S,R,K; $X_3$=R,T,K; $X_4$=T,G,S,N,I; $X_5$=P,S,T; $X_6$=R,K,P; $X_7$=D,Q,N,E; $X_8$=A,Y,I,L,W; $X_9$=D,R,P,K,E,S; $X_{10}$=P,H,V; $X_{11}$=R,K,Q; $X_{12}$=K,D,A,R; $X_{13}$=E,Q,A,L; $X_{14}$=Y,N and $X_{15}$=G,R.

(18) A compound according to (17) comprising an amino acid sequence of SEQ ID No. 18 or SEQ ID No. 19.

(19) A compound according to (1) comprising an amino acid sequence:

(SEQ ID No.: 20)
$I-S-C-X_1-X_2-X_3-X_4-X_5-C-X_6-X_7-X_8-C-X_9-X_{10}-X_{11}-T-G-C-P-$
$Y-G-K-C-M-N-R-K-C-K-C-N-R-C;$ wherein $X_1$=R,T,K,S,Y; $X_2$=T,G,S,N,I,K,Q,A,V,L,Y; $X_3$=P,S,T; $X_4$=R,K,P; $X_5$=D,Q,N,E; $X_6$=A,Y,I,L,W,S,T,V,L,F; $X_7$=D,R,P,K,E,S,T,Y; $X_8$=P,H,V,I,L,A; $X_9$=R,K,Q,N; $X_{10}$=K,D,A,R,E,V,L,I and $X_{11}$=E,Q,A,L,D,N,V,I.

(20) A compound according to (19) comprising an amino acid sequence:

(SEQ ID No.: 21)
$I-S-C-X_1-X_2-X_3-X_4-X_5-C-X_6-X_7-X_8-C-X_9-X_{10}-X_{11}-T-G-C-P-$
$Y-G-K-C-M-N-R-K-C-K-C-N-R-C;$ wherein $X_1$=R,T,K; $X_2$=T,G,S,N,I; $X_3$=P,S; $X_4$=R,K,P; $X_5$=D,Q,N,E; $X_6$=A,Y,I,L,W; $X_7$=D,R,P,K,E,S; $X_8$=P,H,V; $X_9$=R,K,Q; $X_{10}$=K,D,A,R and $X_{11}$=E,Q,A,L.

(21) A compound according to (20) comprising an amino acid sequence of SEQ ID No. 22.

(22) A compound comprising an amino acid sequence:

(SEQ ID No.: 23)
$X_1-X_2-X_3-N-V-X_4-C-X_5-X_6-X_7-X_8-X_9-C-X_{10}-X_{11}-X_{12}-C-X_{13}-X_{14}-$
$X_{15}-T-G-C-P-X_{16}-X_{17}-K-C-M-N-R-K-C-X_{18}-C-X_{19}-X_{20}-C,$ wherein $X_1$=T,Q,S,Y,N; $X_2$=I,F,V,A,L,W; $X_3$=I,T,Y,S,V,A,L; $X_4$=K,S,T,Y,R; $X_5$=R,T,K,S,Y; $X_6$=T,G,S,N,I,K,Q,A,V,L,Y; $X_7$=P,S,T; $X_8$=R,K,P; $X_9$=D,Q,N,E; $X_{10}$=A,Y,I,L,W,S,T,V,L,F; $X_{11}$=D,R,P,K,E,S,T,Y; $X_{12}$=P,H,V,I,L,A; $X_{13}$=R,K,Q,N; $X_{14}$=K,D,A,R,E,V,L,I; $X_{15}$=E,Q,A,L,D,N,V,I; $X_{16}$=Y,N,S,T,Q; $X_{17}$=A,G,V,I,L; $X_{18}$=K,R, $X_{19}$=Y,N,Q,T,S and $X_{20}$=G,R,K.

(23) A compound according to (22) comprising an amino acid sequence:

(SEQ ID No.: 24)
$X_1-X_2-X_3-N-V-X_4-C-X_5-X_6-X_7-X_8-X_9-C-X_{10}-X_{11}-X_{12}-C-X_{13}-X_{14}-$
$X_{15}-T-G-C-P-X_{16}-X_{17}-K-C-M-N-R-K-C-X_{18}-C-X_{19}-X_{20}-C;$ wherein $X_1$=T,Q; $X_2$=I,F; $X_3$=I,T; $X_4$=K,S; $X_5$=R,T,K; $X_6$=T,G,S,N,I; $X_7$=P,S; $X_8$=R,K,P; $X_9$=D,Q,N,E; $X_{10}$=A,Y,I,L,W; $X_{11}$=D,R,P,K,E,S; $X_{12}$=P,H,V; $X_{13}$=R,K,Q; $X_{14}$=K,D,A,R; $X_{15}$=E,Q,A,L; $X_{16}$=Y,N; $X_{17}$=A,G; $X_{18}$=K,R, $X_{19}$=Y,N and $X_{20}$=G,R.

(24) A compound according to (23) comprising an amino acid sequence of SEQ ID No. 25 or SEQ ID No. 26.

(25) A compound comprising an amino acid sequence:

(SEQ ID No.: 27)
$G-V-X_1-I-N-V-X_2-C-X_3-X_4-X_5-X_6-X_7-C-X_8-X_9-X_{10}-C-X_{11}-X_{12}-$
$X_{13}-T-G-C-P-X_{14}-X_{15}-K-C-M-N-R-K-C-X_{16}-C-X_{17}-X_{18}-C;$ wherein $X_1$=P,I,F,V,A,L,W; $X_2$=K,S,T,Y,R; $X_3$=R,T,K,S,Y; $X_4$=T,G,S,N,I,K,Q,A,V,L,Y; $X_5$=P,S,T; $X_6$=R,K,P; $X_7$=D,Q,N,E; $X_8$=A,Y,I,L,W,S,T,V,L,F; $X_9$=D,R,P,K,E,S,T,Y; $X_{10}$=P,H,V,I,L,A; $X_{11}$=R,K,Q,N; $X_{12}$=K,D,A,R,E,V,L,I; $X_{13}$=E,Q,A,L,D,N,V,I; $X_{14}$=Y,N,S,T,Q; $X_{15}$=A,G,V,I,L; $X_{16}$=K,R, $X_{17}$=Y,N,Q,T,S and $X_{18}$=G,R,K.

(26) A compound according to (25) comprising an amino acid sequence:

(SEQ ID No.: 28)
G-V-X$_1$-I-N-V-X$_2$-C-X$_3$-X$_4$-X$_5$-X$_6$-X$_7$-C-X$_8$-X$_9$-X$_{10}$-C-X$_{11}$-X$_{12}$-X$_{13}$-T-G-C-P-X$_{14}$-X$_{15}$-K-C-M-N-R-K-C-X$_{16}$-C-X$_{17}$-X$_{18}$-C;

wherein X$_1$=P,I,F; X$_2$=K,S; X$_3$=R,T,K; X$_4$=T,G,S,N,I; X$_5$=P,S; X$_6$=R,K,P; X$_7$=D,Q,N,E; X$_8$=A,Y,I,L,W; X$_9$=D,R,P,K,E,S; X$_{10}$=P,H,V; X$_{11}$=R,K,Q; X$_{12}$=K,D,A,R; X$_{13}$=E,Q,A,L; X$_{14}$=Y,N; X$_{15}$=A,G; X$_{16}$=K,R, X$_{17}$=Y,N and X$_{18}$=G,R.

(27) A compound according to (26) comprising an amino acid sequence of SEQ ID No.: 29, SEQ ID No.: 30 or SEQ ID No.: 31.

(28) A compound according to any of (1), (2), (3), (4), (5), (6), (7), (8), (9), (10), (11), (13), (14), (17), (19), (20), (22), (23), (25) or (26), wherein the compound is capable of selectively binding to the potassium channel Kv1.3.

(29) A compound according to any of (1), (2), (3), (4), (5), (6), (7), (8), (9), (10), (11), (13), (14), (17), (19), (20), (22), (23), (25) or (26), wherein the compound is capable of selectively binding to the potassium channel Kv1.3 in comparison to the potassium channel Kv1.1.

(30) A nucleic acid sequence encoding for an amino acid sequence as mentioned in any of (1) to (27).

(31) A vector comprising a nucleic acid sequence according to (30).

(32) A host cell comprising a nucleic acid sequence according to (30) or a vector according to (31).

(33) A pharmaceutical composition comprising a compound according to any of (1) to (29).

(34) A compound according to any of (1) to (29) or a pharmaceutical composition according to (33) for use in the treatment of an auto immune disease, obesity, parodontitis and/or tissue transplant rejection.

(35) Use of a compound according any of (1) to (29) or a pharmaceutical composition according to (33) in the manufacture of a medicament for treating or preventing an auto immune disease, obesity, parodontitis and/or tissue transplant rejection.

(36) Method of treating or preventing an auto immune disease, obesity, parodontitis and/or tissue transplant rejection in a mammal by administering a compound according to any of (1) to (29) or a pharmaceutical composition according to (33) to a mammal in need thereof.

(37) Method of manufacturing a compound according to any of (1) to (29) using a nucleic acid sequence according to (30), a vector according to (31) or a host cell according to (32).

EXAMPLES

Example 1—Electrophysiological Measurements

Potassium currents were measured by use of *Spodoptera frugiperda* (Sf21) cells, which express the human Kv1.3 (hKv1.3) channel. The channel activity is induced upon membrane depolarization to voltages more positive than −40 mV. Activation kinetics are rapid and strongly voltage dependent, whereas inactivation is much slower and shows no significant voltage dependence. In Sf 21 cells hKv1.3 has an average current amplitude between 250 pA-5 nA at +40 mV.

1-3 days after infection potassium currents were recorded with the planar patch clamp technique, using the Port-A-Patch (Nanion Technologies GmbH). Ionic currents were activated by voltage steps to a depolarizing potential of +40 mV for 200 ms.

Sf 21 cells were cultured in Grace's insect cell medium supplemented with 10% FBS (Fetal Bovine Serum), 2 mM Glutamine, 1× Yeastolate (from 50× stock solution) and 0.1% Pluronic® F68 (BASF) to a cell density of 2-3×10$^6$ cells/ml.

Electrophysiological buffers were as follows:
External buffer: 160 mM NaCl
4.5 mM KCl
1 mM MgCl$_2$
2 mM CaCl$_2$
5 mM D-Glucose monohydrate
10 mM HEPES/NaoH 7.4
Internal buffer: 75 mM KCl
10 mM NaCl
70 mM K-Fluoride
2 mM MgCl$_2$
10 mM EGTA
10 mM HEPES/KOH pH 7.2

To demonstrate selectivity of the peptides described herein (SEQ ID Nos.: 1 to 31 and in particular cgtx-544 (SEQ ID No.: 25), IC50s were determined for binding of cgtx-544 to Kv1.3, Kv1.1 and Kv1.5. HsTx 1 (SEQ ID No.: 32) was tested as a control.

Peptides were dissolved at 1 μg/μl in 20 mM NaPO$_4$ buffer pH 8.2 (1 mg in 1 ml folding buffer) and dialysed against the same buffer 3×1 L, Float-a-Lyzer cut off 500 Da (Spectrapor) at room temperature.

HsTx 1 binding was tested at various concentrations of e.g. 100 pM, 1 nM, 10 nM, 50 nM, 100 nM, 500 nM, and 1 μM—depending on the tested channel. Representative measurements for Kv 1.1, Kv1.3 and Kv1.5 are depicted in FIGS. 1 *a*), 1 *b*), and 1 *c*) respectively.

The IC50 for HsTx 1 binding to Kv1.3 was 25±2.1 nM. The IC50 for HsTx 1 binding to Kv1.1 was 11.3 μM. No binding could detected for Kv1.5. Thus HsTx 1 has ~450-fold higher selectivity for Kv1.3 vs. Kv1.1.

Cgtx-544 binding was tested at various concentrations of e.g. 1 nM, 10 nM, 50 nM, 100 nM, 1 μM and 5 μM—depending on the tested channel. Representative measurements for Kv1.1, Kv1.3 and Kv1.5 are depicted in FIGS. 1 *d*), 1*e*), and 1) *f*, respectively.

The IC50 for cgtx-544 binding to Kv1.3 was 6.9 nM. Up to a concentration of 10 μM no binding to Kv1.5 could be detected. Kv1.1 was blocked at about 22% at 10 μM. Thus cgtx-544 has a higher selectivity for Kv1.3 vs. Kv1.1 compared to HsTx 1.

Example 2—Comparison of Binding to Kv1.3 and hERG

In the following example binding of selected peptides to Kv1.3 and hERG was compared by electrophysiological measurements.

Cell Systems

To determine binding to Kv1.3, Jurkat cells endogenously expressing Kv1.3 were used. For binding to hERG, HEK cells stably expressing hERG were used.

Cell Culture

Cell culture was performed using standard cell culture techniques. In brief, cells were grown on 10 cm culture dishes or T75 culture flasks in DMEM-based media. With a confluence of about 60-80%, cells were split every 2-3 days.

For recordings on the Patchliner (Nanion), Jurkat cells were resuspended and then spinned in a centrifuge. Before spinning, HEK cells were treated with Trypsin, to detach them from the dish surface. After spinning, cells were resuspended in external recording buffer to a density of approximately 1-2 million cells per ml.

Internal recording solution: 50 mM KCl
10 mM NaCl
60 mM KF
20 mM EGTA
10 mM HEPES/KOH, pH 7.2, (Osm: ~290 mOsm)
5 mM Mg-ATP and 0.3 mM Na-GTP were added fresh to the internal solution and pH adjusted to 7.2.

External recording buffer: 140 mM NaCl
4 mM KCl
1 mM MgCl2
2 mM CaCl2
5 m D-Glucose monohydrate
10 mM HEPES/NaOH pH 7.4, (Osm: ~298 mOsm)

Compounds

The following compounds were tested:
Compound 1: cgtx 538
Compound 2: cgtx 539
Compound 3: cgtx 540
Compound 4: cgtx 541
Compound 5: cgtx 542
Compound 6: cgtx 543
Compound 7: cgtx-544
Compound 8: cgtx 547

Electrophysiological Measurements

Electrophysiological recordings were performed with a Patchliner, recording up to 8 channels, simultaneously. The Patchliner is an automated patch clamp system utilizing borosilicate glass chips (NPC-16) for planar patch clamp, and operating via the PatchControlHT software. NPC-16 chips with a resistance of 3-5 MΩ for Jurkat cells and 2-3 MΩ for HEK cells were used for recordings. During recordings, cells were kept in a "cell hotel" where they were periodically pipetted up and down to maintain viability. Cells were viable for approximately 2-3 hours.

PatchControlHT Software

To operate the Patchliner two programs running on the computer, simultaneously—Nanion's PatchControlHT and PatchMaster from HEKA.

PatchMaster controls the HEKA EPC10 amplifiers and executes the recordings. Pulse Protocols and Online Analyses can be generated within this program. PatchControlHT is used to define the complete experimental routine from catching and sealing the cells to going whole cell and obtaining the desired recordings. Bidirectional communication between PatchControlHT and PatchMaster allows PatchControlHT to adjust its actions according to cell status (giga seal, whole cell configuration).

The program fully navigates the robotic functions of the Patchliner including the pipette for conducting solution exchanges. Simultaneously, PatchControlHT also controls the amplifier and reads out all the important patch parameters from PatchMaster. PatchControlHT is a graphical user interface, where all parameters and success criteria for the experiment are defined. If the success criteria are not reached for a recording well, the option is available that PatchControlHT discontinues recording from that particular well.

Experimental Routine

To establish the appropriate recording conditions, chip filling, cell catching, sealing and breaking into whole cell mode were accomplished by standard procedure functions of the Patchliner. At the end of this routine, the amplifier settings (e.g. holding potential, slow capacity compensation and gain) were set appropriately for the desired recordings, then the recording was started.

Within each experiment, cells were washed three times with external solution to ensure stable recordings. Compounds 1-8 were further tested on hERG expressing cells. The exposure time of each compound was 4 minutes, in total, each experiment ran 24 minutes.

Voltage Protocol

For hERG: hERG currents were elicited using a voltage step protocol from a holding potential of −80 mV to −40 mV for 500 ms followed by a step to +40 mV for 500 ms, a −40 mV test pulse for 500 ms to obtain the tail current, and then returning to the holding potential. The step was repeated every 10 seconds.

The protocols were continuously run and online results were continuously read. This was done so that changes due to washes and/or compound application could be monitored and the reaching of steady state be evaluated.

Data Analysis

Data recording and analysis were performed with 2× EPC10 Quadro amplifiers, PatchMaster software package (HEKA Electronics, Lambrecht/Pfalz, Germany), Excel and Igor (WaveMetrics, USA).

For pharmacology on hERG, peak amplitude at the 2nd −40 mV step (tail current) was calculated using online analysis functions in PatchMaster. The leak (calculated from the 1st step to −40 mV) was subtracted from this peak to calculate the true peak and these could be plotted as a function of time.

Values were exported to Excel to calculate concentration response curves in Igor. Figures were drawn and exported using Igor (WaveMetrics, USA). Concentration response curves were constructed in Igor. A Hill equation was fitted to estimate the IC50 for each compound and IC50 was calculated relative to maximum block. Values are represented as average±S.E.M when possible.

Results

Compound 1-8 Tested on hERG Current

Electrophysiological measurements of compounds 1-8 on Kv1.3 currents indicated that these peptides were active. Therefore, compounds 1-8 were tested on hERG expressing HEK cells. To investigate the effect of these compounds, a two-point screening procedure was performed. Usually, 3 to 5 cells were tested to ensure accuracy. Each experiment started with three washes to ensure stable currents. The hERG currents increased slightly, but became stable after the second wash. Compound 1, 2, 4, 5, 7, and 8 seemed to have only low effects on the hERG current.

Figure 3:
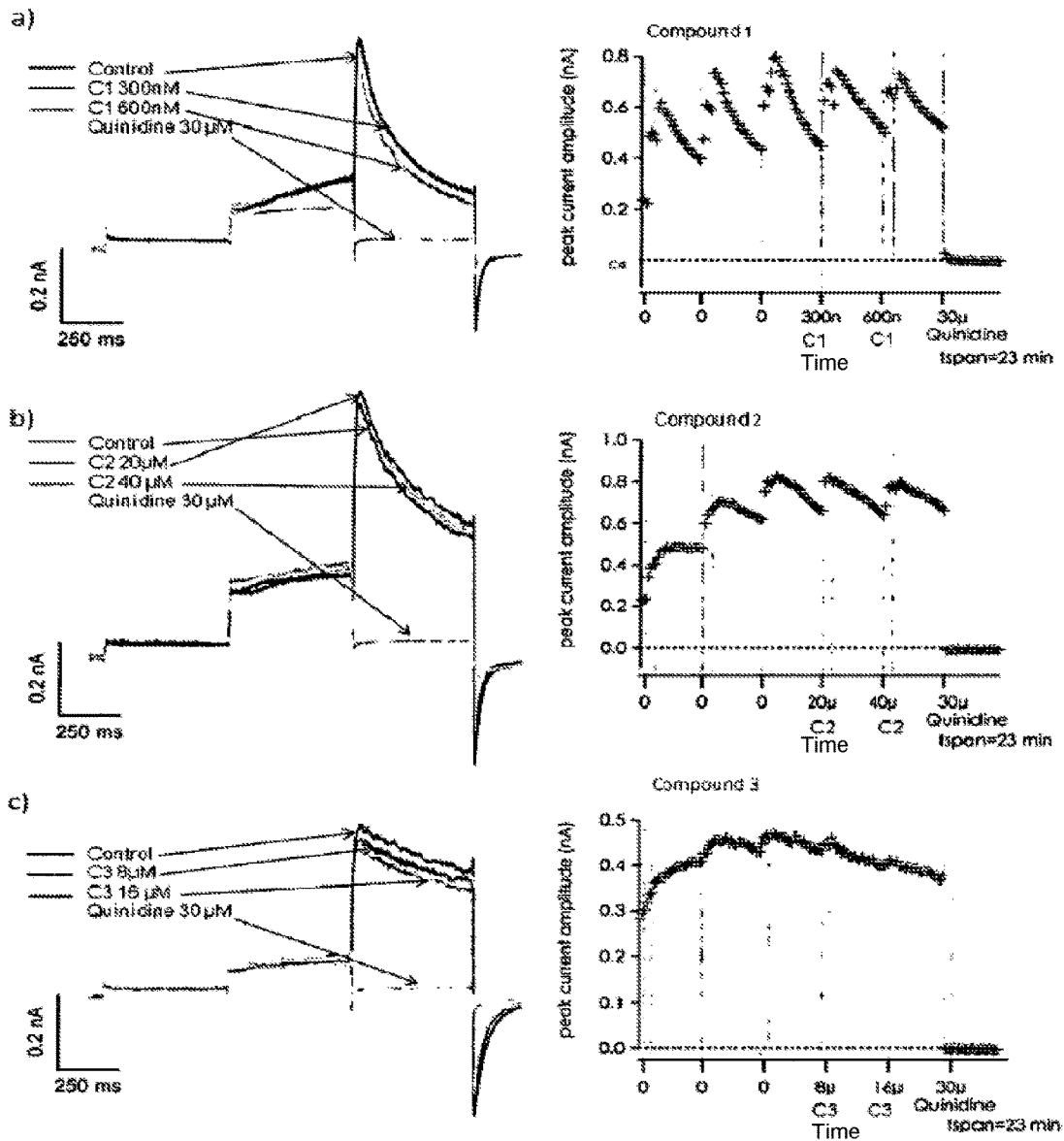
FIG. 3 Effect of Compound 1-8 (C1-8).
Figure 3:
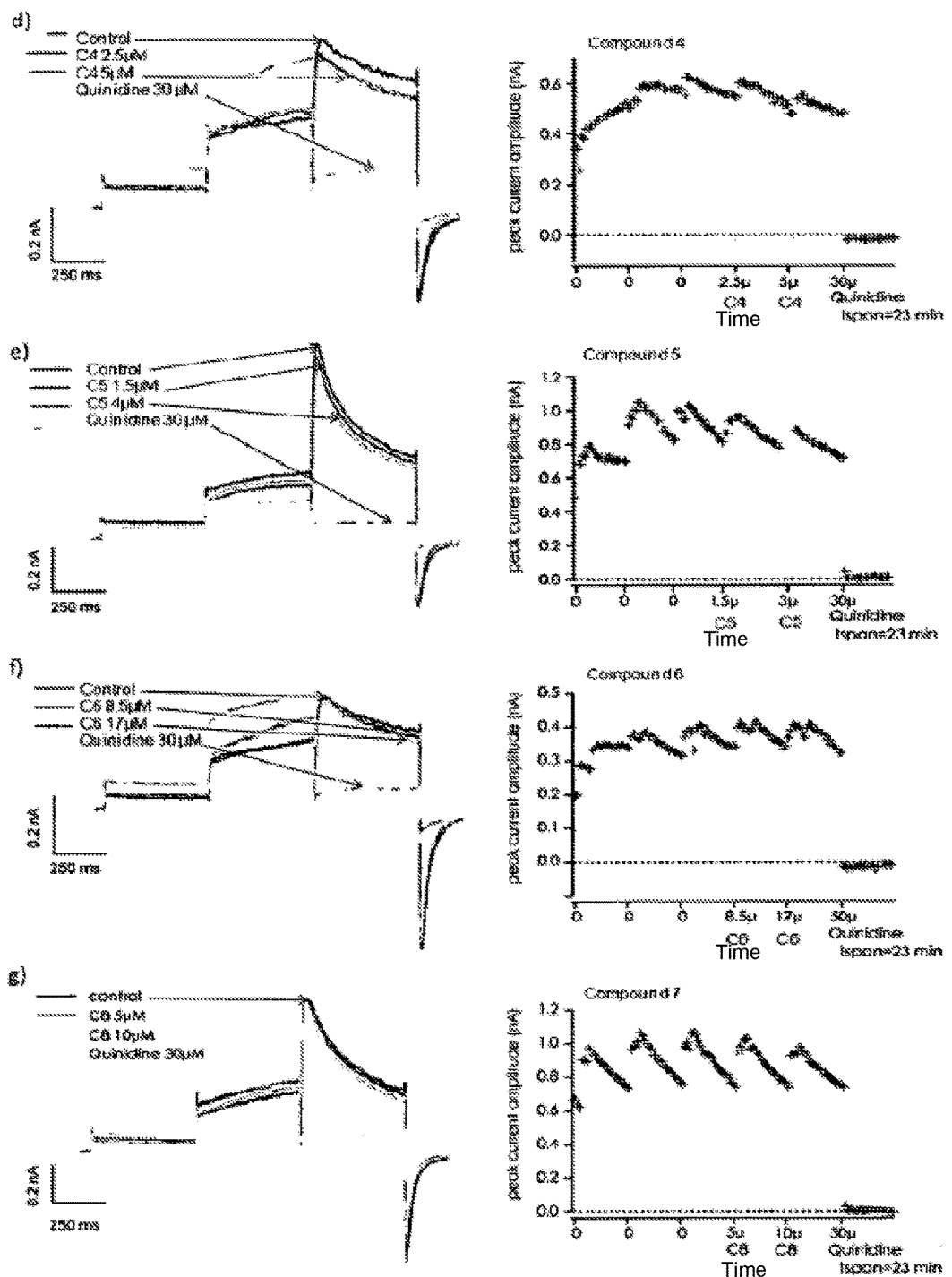
Figure 3:
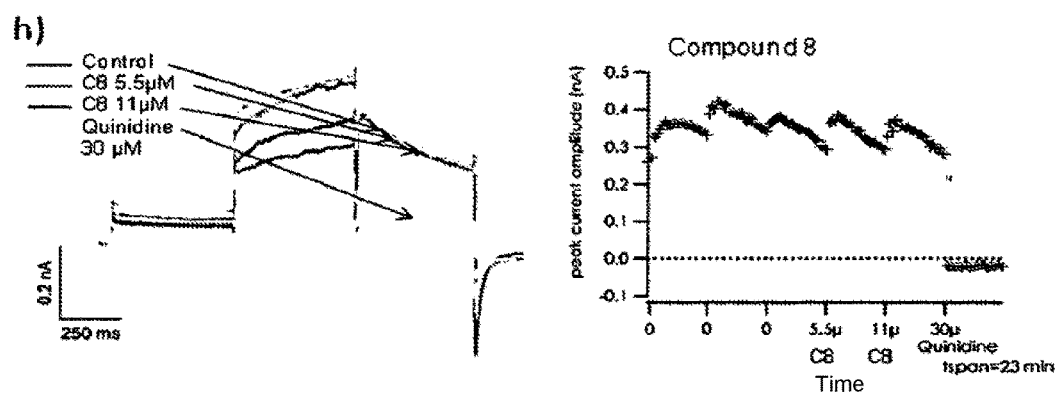

Usually, the effects of compound 1-8 could be also explained by run down effects of hERG currents. The results are shown in FIG. 3. A summary of the mean current block±SEM of all compounds are depicted in Table 1.

TABLE 1

Summary of the effects of compound 1-8. Test concentrations are different for each compound. Normalized block was calculated from the steady state current at the end of each compound application. All compounds seemed to have either no or only small effects on the hERG current at lower concentrations. At higher concentrations, compounds seemed to affect the hERG, however, these effects could be due to run down of hERG currents.

| Compound | Test concentration | N | Normalized Block | SEM |
|---|---|---|---|---|
| 1 | 300 nM | 4 | 0.00 | 0.05 |
|   | 600 nM | 4 | 0.05 | 0.06 |

TABLE 1-continued

Summary of the effects of compound 1-8. Test concentrations are different for each compound. Normalized block was calculated from the steady state current at the end of each compound application. All compounds seemed to have either no or only small effects on the hERG current at lower concentrations. At higher concentrations, compounds seemed to affect the hERG, however, these effects could be due to run down of hERG currents.

| Compound | Test concentration | N | Normalized Block | SEM |
|---|---|---|---|---|
| 2 | 20 µM | 5 | 0.16 | 0.04 |
|  | 40 µM | 5 | 0.19 | 0.06 |
| 3 | 8 µM | 4 | 0.04 | 0.05 |
|  | 16 µM | 4 | 0.13 | 0.03 |
| 4 | 2.5 µM | 5 | 0.09 | 0.02 |
|  | 5 µM | 5 | 0.16 | 0.02 |
| 5 | 1.5 µM | 8 | 0.08 | 0.03 |
|  | 3 µM | 8 | 0.19 | 0.05 |
| 6 | 8.5 µM | 4 | −0.03 | 0.05 |
|  | 17 µM | 4 | 0.01 | 0.09 |
| 7 | 5 µM | 3 | 0.04 | 0.02 |
|  | 10 µM | 3 | 0.07 | 0.04 |
| 8 | 5.5 µM | 5 | 0.07 | 0.02 |
|  | 11 µM | 5 | 0.12 | 0.03 |

Further Analysis

The above analysis was done after subjecting the respective peptides to a folding protocol as described in Example 8 without purifying the completely folded peptides.

In addition, cgtx-544 was folded and purified as described above. The analysis was then repeated with this cgtx-544 (Sing). Further, cgtx-544 (Sing) was then tested on Kv1.3 by incubating for longer periods of time, namely about 20 min—a time that correlates better with the long on-rate of the peptide. Under these conditions cgtx-544(Sing) displays an IC50 of about 900 pM after folding and purification compared to 6.9 nM of the unpurified cgtx-544 (see Example 1). The results are depicted in FIG. 35.

Example 3—Stability of cgtx-544 (SEQ ID No.: 25) in Human and Rat Plasma

1. Determination of Stability Ex Vivo in Human and Rat Serum Samples

The aim was to test the stability of the cgtx-544 peptide in blood plasma of mammals after different incubation times at room temperature (RT) and 37° C. Stability was defined as IC50 value of cgtx-544 after different incubation times at RT and 37° C. Blood plasma was prepared from fresh blood samples from healthy rats or humans. Heparin was added to fresh blood samples to prevent clogging. Plasma preparation was performed by centrifugation for 2 min at 2000×g at RT.

The IC50 of cgtx-544 was defined before the start of the experiment—the electrophysiological assay yielded a IC50 value of 46.1 nM±3.9 nM (for n=5 cells). As the cgtx-544 peptide used in these experiments was incompletely folded, a higher IC50 than normal was determined. A negative control of the prepared human and rat plasma showed no unspecific binding of plasma components to Kv1.3 channels expressed in Sf21 insect cells.

To investigate the stability and activity in plasma the peptide was added to freshly prepared human and rat blood plasma at a final concentration of 20 µM. The samples were split into two aliquots and incubated at 37° C. and at room temperature (RT, 20° C.). For the electrophysiological analysis serial dilutions of the samples were prepared.

Time Point 0 h: Directly after adding the peptide to the plasma, samples were analyzed and displayed a strong affinity to Kv1.3 channels. The IC50 value improved to 20.9 nM for cgtx-544 in human plasma and 15.0 nM in rat plasma (data not shown).

Time Point 24 h: During the following 24 hours a significant change in activity of the peptide probes stored at 37° C. and RT could not be detected.

Time Point 48 h: After 48 hours the activity of the peptide incubated at 37° C. decreased and the IC50 values of cgtx-544 incubated in human plasma or in rat plasma was two times higher compared to t=0 h (37.3 nM and 57.8 nM respectively). Activity of cgtx-544 stored at RT remained unchanged.

Time Point 14 days: After 14 days of incubation at 37° C. no activity was detected. cgtx-544 probes incubated at RT displayed an unchanged activity.

Example 4—cgtx-544 (SEQ ID No.: 25) Efficacy on Isolated Human $T_{EM}$ Cells

1. Analysis of Kv1.3 Currents in Isolated Human $T_{EM}$

The insect cell line Spodoptera frugiperda (Sf21) was used in combination with a Baculovirus infection system for the heterologous expression of recombinant ion channels. Sf21 cells offer highly specific protein expression and correct posttranslational modifications resulting in functional channels with proposed comparability of electrophysiological parameters of ion channels in vivo. Therefore, it was necessary to compare the electrophysiological properties of the potassium selective ion channel Kv1.3 expressed in Sf21 cells and endogenously expressed Kv1.3 channels in $T_{EM}$ cells.

For the comparison of characteristic voltage dependent Kv1.3 channel activation a typical voltage protocol from −60 mV to +60 mV in 20 mV steps (activation pulse 200 ms) was used. Cells were clamped at a holding potential of −100 mV. FIG. 4 shows the current response of two individual Sf21 and $T_{EM}$ cells (FIGS. 4A and 4B, respectively) and the pulse protocol for voltage dependent Kv1.3 activation (FIG. 4C).

FIG. 5 shows the corresponding normalized voltage-current-correlation. Kv1.3 starts to open at a depolarization of the membrane from the holding potential (−100 mV) to −20 mV and reaches its maximum open state at +60 mV. Even though the expression of Kv1.3 is much higher in Sf21 cells, the characteristic voltage dependent activation remains unchanged.

The maximal observed current, which clearly originates from Kv1.3 activity, and the applied voltage allows to assess the total conductivity of all Kv1.3 channels. Accordingly, the number of channels can be extracted using the known conductivity of a single Kv1.3 channel. The maximal K+ outward current is defined as the difference between activated unblocked and maximally blocked (full block) currents during the first 20% of the current trace. By variation of the infection conditions, it is possible to control the expression level of Kv1.3 in Sf21 cells, according to the needs of the investigation. Under our standard conditions a maximal current of 2-5 nA, a conductance of 33-50 nS and a number of 2500-3800 channels per cell can be estimated.

The heterologous expression system in Sf21 cells displays a suitable method for electrophysiological analysis of pharmacologically interesting ion channels in vitro. Based on these observations it can be assumed that the folding and insertion of Kv1.3 ion channels into the plasma membrane of Sf21 cells is comparable to native Kv1.3 proteins in $T_{EM}$ cells.

It could be clearly demonstrated that heterologously expressed Kv1.3 channels can serve as a model system to study drug targeting by assessment of electrophysiological parameters.

A specific Kv1.3 block was performed with peptide compound cgtx-544. The peptide shows high affinity on Kv1.3 channels as was shown before and was also tested on isolated human $T_{EM}$ cells (FIGS. 6A-6B). Note that the cgtx-544 used in these experiments was incompletely folded and displays a higher IC50 than normal. Nevertheless, the compound exhibited the same values on Kv1.3 transfected Sf21 cells as on human $T_{EM}$ cells (FIGS. 6A-6B).

Example 5—Therapy of Antigen Induced Arthritis with the Peptide cgtx-544 (SEQ ID No.: 25)

1. Experimental Model
1. AIA—Antigen Induced Arthritis

The disease model antigen induced arthritis (AIA) in rat represents a T cell dependent autoimmune arthritis, that resembles many features of the rheumatoid arthritis in humans. Hence, this system can serve as a disease model for the assessment of the therapeutic success of T cell suppressive peptides disclosed herein. One major advantage of this therapeutic approach over current therapies (e.g. the use of general cytostatica) is the fact, that only the small subset of the immune system that is causally involved in the generation of the disease is suppressed, whereas other important components of immune defence like, for example, the innate immune system is still intact. In addition this disease model enables the testing of efficacy and tolerance of cgtx-peptides in vivo.

2. Induction of Arthritis

The whole experiment takes place in a time period of 4 weeks. The pre-immunisation takes place on day −21 (start of the experiment) and day −14, by subcutaneous injection of a mixture of mBSA and *M. tuberculosis* preparations in incomplete Freund's adjuvant (IFA). The local induction of inflammation in one knee joint is induced by a single intra-articular injection of the antigen mBSA in the right knee at day 0. In this experimental setup the second (left) untreated knee joint serves as an intra-individual control.

The treated knee joints develop a severe swelling reaction during the first hours after induction that usually reaches a maximum of swelling on days 1 and 2 after induction. This phenotype is stable for another 2 to 3 days and afterwards the swelling abates again.

This scheme allows the induction of a local, reproducible arthritis in >95% of the experimental animals. In the negative control experiments the same volume (as for the mBSA induction solution) of 0.9% NaCl was administered in the knee of the control animals (see FIGS. 7 and 8).

2. Material and Methods
2.1 Animals

Lewis rats, female, 180-200 g body weight (BW), age ca. 8 weeks, Janvier, France The animals were kept under conventional housing conditions—5 animals per Makrolon cage type IV, food and water ad libitum in a 12 hours day/night rhythm, room temperature at 22+/−2° C. with air humidity at 55+/−5%.

2.2. Production of the Emulsion for Immunisation, Animal Immunisation & Induction of Local Arthritis
2.2.1. Emulsion for Immunisation and the Process of Immunisation
2.2.1.1. Material: *Mycobacterium tuberculosis* H37 Ra (BD 231141)

Incomplete Freund's Adjuvant (Sigma F5506)
mBSA (Sigma A1009-1G)
0.9% NaCl (Braun)
Isofluran (Abbott)

2.2.1.2. Pre-Immunisation Emulsion:

Solution A: mBSA stock solution (50 mg/ml):
Addition of 20 ml aqua inj. to 1 vial mBSA (1 g) under aseptic conditions.
The sterile solution can be stored at 4° C. for several months.

Solution B: Complete Freund's Adjuvant (CFA) stock solution (10 mg/ml):
Addition of 10 ml (1 vial) of Incomplete Freund's Adjuvant to 1 vial of *M. tuberculosis* containing 100 mg bacteria. The solution can be stored at 4° C. for 1 month.

Preparation of the Mix
Both components are mixed at equal volumes resulting in an emulsion (mixing under aseptic conditions in a clean bench). The components are pipeted into a 15 ml or 50 ml Falcon tube as described in the following:
1. Solution A—mBSA stock solution
2. Solution B—*M. tuberculosis* solution.

Directly after the addition of the components, the tube is vortexed for 20 seconds. In the last preparation step the solution is emulsified with an Ultrasonic Processor (0.5 cycles with an amplitude of 60%) until a thick emulsion has formed.

2.2.1.3. Pre-Immunization

The animals were pre-immunized twice before the final arthritis induction. Pre-immunizations took place at day −21 and day −14. At these time points the immunization solution was injected subcutaneously. After induction of narcosis with 5%, isofluran, anesthesia was maintained with 2% isofluran. A total of 500 µl of the emulsified solution was applied by using a 25 G canula. 125 µl of pre immunization emulsion were injected subcutaneously at 2 sides (right and left) of the tail base as well as at 2 sides above the left and right scapula.

2.2.1.4. Induction of Local Arthritis

At day 0 arthritis was induced by intra-articular administration of the antigen (500 µg mBSA in 50 µl 0.9% NaCl) in the right knee joint. The left knee was left untouched as an intra-individual control. The animals were narcotized and the site of injection was disinfected. The application was done with a short and fine canula (30 G, ½) to minimize tissue damage. After administration of the antigen and withdrawal of the canula, the joint was slowly bent and extended for several times.

2.2.2. Measurement of the Swelling of the Knee Joint

The sagittal diameter of the knee joint was determined with a calliper. The experimental animals were narcotized for a brief period of time and positioned on the back. The leg was adjusted to a 90 degree angle and the measurement of the sagittal diameter of the knee was carried out three times.

2.2.3. Blood Withdrawal

For the blood withdrawal the animals were narcotized briefly, the tail was disinfected and the tail vein was punctured with a canula, 50 µl of blood were withdrawn with a heparin coated pipette and mixed with 5 µl of a stabilising agent (CPD) and 1 µl heparin (1.5 U/µl diluted 1:4 in 0.9% NaCl).

2.2.3. Hematology

White Blood Cells (WBC) were counted with a Coulter Counter in the automatic mode.

2.2.4. Measurement of Body Weight

The body weight of the experimental animals was measured once a day between 8:00 and 9:00 AM.

2.2.5. Clinical Examination and Measurement of the Swelling of the Knee Joints

After the induction of local arthritis the experimental animals were examined on a daily basis. The swelling of the knee joints was measured and the general health status was scored.

2.3. Treatment of Experimental Animals

The treatment of the animals started at day −3 with the application of peptide cgtx-544 (SEQ ID No. 25) with a dosing of 1 mg/kg body weight (BW) in a volume of 0.6 ml 0.9% NaCl or alternatively for the control animals with the same volume of 0.9% NaCl (excipient). The peptide or the excipient, respectively, was administered i.v. in the tail vein of narcotized animals. The treated animals were observed for ca. one hour after treatment.

3. Results

During the pre-immunisation phase the experimental animals were monitored intensively and on days −21, −14, −7, 0 and 7 blood samples were withdrawn for the monitoring of the immune status of the animals. There was a very good correlation between the development of the inflammation and the counts of the white blood cells (WBC, Leucocytes) in the peripheral blood at the corresponding time points of analysis.

The number of the WBC's in the peripheral blood of recently immunised animals (day −21 and day −14) increases dramatically in comparison to the untreated animals (see FIG. 9). The number of WBC's reach a maximum between days −14 and −7 and declines afterwards. The increase of the WBC's correlates with the severity of inflammation induced by the immunisation.

Immediately after induction of the local arthritis the WBC's show a short-term increase (see FIG. 9). However, this short-term increase is smaller because the inflammatory response is localized. Control animals that were immunised with 0.9% NaCl did not show any differences in the WBC counts.

Pre-immunised animals develop a severe swelling reaction of the right knee joint only a few hours after induction of local arthritis by mBSA-injection (see FIG. 8). On the contrary, the untreated left knee serving as an intra-individual control knee, does not show any sign of a swelling reaction.

Comparison of animals that have been treated with cgtx-544 peptide with untreated (excipient) controls reveals, that cgtx-544 treatment leads to a clear reduction of the knee joint swelling as compared to the untreated control animals (see FIG. 10). It can be concluded that animals treated with cgtx-544 show an obvious reduction of knee joint swelling and a faster regression of the swelling as compared to untreated control animals.

Example 5a—Preventive Efficacy of cgtx-544 Peptide in the AIA Rat Model of RA 1. Material and Methods After two immunizations on day −21 and day −14 with an emulsion of the antigen mBSA in complete Freund's adjuvant and 750 μg heat-inactivated *Mycobacterium* (*M.*) *tuberculosis* AIA was induced by intra-articular injection of methylated BSA on day 0 in the right knee as described in Example 5. For cgtx-544 peptide efficacy studies, rats received daily intravenous injections of 0.1, 1 or 5 mg/kg cgtx-544 peptide (low, medium and high dose level) starting on day −3 or vehicle (0.9% NaCl) for a period of 10 days (day −3 until day 6).

Arthritis severity was monitored by measurement of the knee joint diameters in triplicates using a caliper. Values were normalized to day −21. Difference of knee swelling values was calculated by subtraction of left (un-induced) from right (induced) knee diameters.

Blood samples were taken regularly for monitoring of hematological parameters. Haematological parameters were assessed in all animals weekly before induction, at day of induction and 10 days after induction (days −21, −14, −7, 0 and 10). Hematological data of untreated animals (day −21) were comparable to those reported in the literature (Waynforth & Flecknell, 1992). Absolute counts of white blood cells (WBC), neutrophil granulocytes and lymphocytes were analyzed among others, the last two also stated in percentage of total WBC. EDTA whole blood of seven individuals from both vehicle and cgtx-544 peptide therapy group was measured with Sysmex XT-2000i.

2. Results

All tested dose levels of cgtx-544 (0.1, 1, and 5 mg/kg BW) showed a clear reducing, dose dependent and statistically significant effect on the knee swelling in treated animals (FIG. 18).

For a statistical analysis of results the Welsh two sample t-test was used. In the following the statistical analysis of all tested dose levels of cgtx-544 (0.1, 1, and 5 mg/kg BW) are shown for day 1 and 3. All tested dose levels showed a statistically significant reduction in knee swelling when compared to the vehicle control group (FIGS. 19A-19B).

In summary, cgtx-544 peptide therapy in the AIA model had a strong effect on the inflammatory arthritic symptoms, particularly on the knee swelling with a maximal reduction of 70%. After seven days of treatment, knee diameters in the therapy group decreased further to a diameter nearly comparable to the non-induced, intra-individual control knee. Furthermore, WBC, neutrophil granulocytes and lymphocytes (data not shown) of cgtx-544 peptide treated individuals showed absolute and relative cell counts comparable to vehicle treated individuals.

Example 5B—Curative Efficacy of cgtx-544 in the AIA rat model of RA

1. Materials and Methods

After two immunizations on day −21 and day −14 with an emulsion of the antigen mBSA in complete Freund's adjuvant and 750 μg heat-inactivated *Mycobacterium* (*M.*) *tuberculosis* AIA was induced by intra-articular injection of methylated BSA on day 0 in the right knee as described above in Example 5. For cgtx-544 peptide efficacy studies, rats received daily intravenous injections of 1 mg/kg cgtx-544 peptide starting on day 0 immediately after arthritis induction or starting on day 1. Control animals received daily injections of vehicle (0.9% NaCl).

Arthritis severity was monitored by measurement of the knee joint diameters in triplicates using a caliper. Values were normalized to day −21. Differences of knee swelling values were calculated by subtraction of left (un-induced) from right (induced) knee diameters.

2. Results

Both tested time points of treatment start with cgtx-544 (Mix) (1 mg/kg BW) showed a clear reducing, and statistically significant effect on the knee swelling in treated animals (FIG. 20).

For a statistical analysis of results the Welsh two sample t-test was used. In the following the statistical analysis of both treatment regimens of cgtx-544 (d0 and d1) are shown for day 1, 2 and 3. Both treatment regimens showed a statistically significant reduction in knee swelling when compared to the vehicle control (FIGS. 21A-21C).

The time course of the white blood cell (WBC) count is shown in FIG. 22. The time course of neutrophils is shown in FIG. 23. The time course of lymphocytes is shown in FIG. 24.

cgtx-544(Mix) treatment shows a significant reduction in knee joint swelling. The remaining swelling in treated animals was assumed to be due to antibody/antigen reactions. Therefore, immunized as well as naïve animals were tested for the presence of mBSA specific antibodies. Antibodies against mBSA could be detected in all immunized animals of groups H and I seven days after arthritis induction (FIG. 27). Naïve animals (experimental group F) did not show any reactivity on mBSA. cgtx-544 therapy does not seem to suppress B-lymphocytes and antibody formation. Additionally, immunized animals after 10 days under cgtx-544 peptide therapy showed no reactivity on cgtx-544(Mix) (fusion protein L544-2a with trx-tag, data not shown).

In summary, cgtx-544 peptide therapy in the AIA model had a strong effect on the inflammatory arthritic symptoms, particularly on the knee swelling with a maximal reduction of 40% if therapy started on day 0 immediately after arthritis induction or 58% if therapy started on day 1. After seven days of treatment, knee diameters in the therapy groups decreased further to a diameter nearly comparable to the non-induced, intra-individual control knee. Furthermore, WBC, neutrophil granulocytes and lymphocytes of cgtx-544 peptide treated individuals showed absolute and relative cell counts comparable to vehicle treated individuals.

Example 5C—Sustained Efficacy of cgtx-544(Mix) in the AIA Rat Model of RA

Previous experiments (see Examples 5A and 5B) had demonstrated that cgtx-544 has an excellent efficacy in the AIA rat model under different treatment regimens—curative and preventive—when applied daily. We attempted to clarify for how long the activity of cgtx-544 sustains in the AIA model in order to get a hint of how long the treatment intervals with cgtx-544 will be. Therefore, a curative treatment regimen with a once weekly application scheme was set up.

1. Materials and Methods

After two immunizations on day −21 and day −14 with an emulsion of the antigen mBSA in complete Freund's adjuvant and 750 µg heat-inactivated *Mycobacterium* (*M.*) *tuberculosis* AIA was induced by intra-articular injection of methylated BSA on day 0 in the right knee as described above in Example 5. For cgtx-544 peptide efficacy and sustained therapy effect studies, rats (10 individuals) received a single intravenous injection of 1 mg/kg cgtx-544 peptide on day 1 (d1) after arthritis induction. On day 4 (d4) the cgtx-544 therapy group was divided into two subgroups of 5 individuals each. The first subgroup received a second injection of cgtx-544 in order to evaluate whether a second injection will lead to a further reduction in swelling. The second subgroup did not receive an additional dosing. Control animals received a single injection of vehicle (0.9% NaCl) on day 1.

Arthritis severity was monitored by measurement of knee joint diameters in triplicates using a caliper. Values were normalized to day −21. Differences of knee swelling values were calculated by subtraction of left (un-induced) from right (induced) knee diameters.

2. Results

Single injection (1×d1) with cgtx-544 (1 mg/kg BW) showed a clear and statistically significant reduction of knee swelling in treated animals 24 h after application (FIG. 25). Swelling could be reduced again to a significant value after a second single injection on day 4 (1×d1 and 1×d4). Knee swellings remained at the same level and did not increase after the first and second injection.

For a statistical analysis of results the Welsh two sample t-test was used. In the following the statistical analysis of both treatment regimens of cgtx-544 (1×d1 or 1×d1 and 1×d4) are shown for day 2 (before group was divided) and day 5 (divided groups). Both treatment regimens showed a statistically significant reduction in knee swelling 24 h after each injection when compared to the vehicle control (FIG. 26).

In summary, cgtx-544 peptide therapy in the AIA model had a strong and sustained effect on the inflammatory arthritic symptoms, particularly on the knee swelling with an onset of swelling reduction 24 h after a single injection. Even three days after the single injection, cgtx-544 peptide demonstrated sustained activity and clinical effect, with the level of knee swelling remaining constant. Therefore, the peptide does not have to be administered daily for a sustained therapeutic effect in the AIA rat model. It may thus be possible to achieve treatment intervals of 3-4 days for i.v. administration (or longer for a potential s.c. administration route).

Example 6—Comparison of Methotrexate (MTX) Therapy with cgtx-544 Peptide (SEQ ID No.: 25) Therapy in the AIA Rat Model 1. Comparison of Methotrexate (MTX) Therapy with cgtx-544 (SEQ ID No.: 25) Therapy in the AIA Rat Model Depending on form and severity of the disease, therapy with methotrexate (MTX) differs in dose and regimen. Comparable to standard therapies, we examined a high-dose MTX therapy 1 mg/kg bodyweight 1×weekly s.c. (group J, n=7) and a low-dose MTX therapy with 100 µg/kg bodyweight 1×daily i.v. (group L, n=7) in the AIA rat model. High-dose MTX therapy started on the first day of experiment (day −21) and was given another three times (day −14, −7, 0). Low-dose MTX therapy started three days before arthritis induction (day −3) and endured another seven days after arthritis induction. Results were compared with the cgtx-544 therapy group I (1 mg/kg bodyweight cgtx-544, same regimen as group L) and the vehicle control group H (0.9% NaCl 1×daily i.v. starting on the day of induction, day 0). Arthritis severity was monitored by measurement of the knee joint diameters in triplicates using a caliper. EDTA whole blood samples were taken regularly for monitoring the immune status.

1.1 Reduction of Knee Swelling to a Lesser Extend with MTX Therapy Compared to Cgtx-544 Therapy First, knee parameter of high-dose (J) and low-dose (L) MTX therapy groups are compared to the vehicle control group (H), in order to show possible efficacy differences depending on dose and regime. Second, the three groups with the same regimen (daily i.v. application) are compared, low-dose (L) MTX therapy group, cgtx-544 therapy group (I) and vehicle control group (H).

Difference of absolute increase of swelling was calculated by subtracting left (un-induced) from right (induced) knee diameters. Calculated difference at the beginning of the experiment of both MTX high-dose and low-dose therapy groups was close to zero (0.01±0.06 mm and 0.0±0.03 mm respectively), as both knees are comparable in size. One day after arthritis induction, the difference raises up to 3.17±1.26 mm and 3.45±0.87 mm, respectively (FIG. 11).

In contrast to the cgtx-544 therapy group, the decrease of swelling is not very rapid as compared to the vehicle control group which has an absolute difference of 3.79±1.10 mm (FIG. 12).

For normalization of values with a scaling between 0 and 1, the relative increase of swelling is set to 0 at the beginning of the experiment (day −21), and the difference of the relative increase of swelling was calculated as before. Relative difference of the MTX high-dose and low-dose therapy groups came to 0.39±0.16 and 0.43±0.11, respectively (FIG. 13).

In comparison, vehicle control group and cgtx-544 therapy group came to 0.46±0.14 and 0.18±0.05, respectively (FIG. 14). To sum up, relative to the vehicle control group we observed a reduction of knee swelling on an average of 15% in MTX high-dose therapy rats and 7% in MTX low-dose therapy rats, compared to 60% in cgtx-544-therapy rats 24 h after arthritis induction.

1.2 Cytostatic Effect of MTX on Proliferating Cells

For screening the state of health of all individuals, complete haemograms were used again. EDTA whole blood of seven individuals from both MTX high-dose and low-dose therapy groups were measured with Sysmex XT-2000i.V weekly before induction, at day of induction and 4 and 7 days after induction (day −21, −14, −7, 0, 4 and 7; MTX low-dose therapy group additionally on day −3, when i.v. application started). Haematological data of untreated animals (day −21) are comparable to data provided in the literature.

1.2.1 White Blood Cells

At the beginning of the experiment (day −21), white blood cell count of MTX high-dose and low-dose therapy group came to $9.41±1.42×10^3/\mu l$ and $11.66±2.81×10^3/\mu l$, respectively. Due to inflammatory reactions of the immune system, WBC count raised after the first and second immunization up to $20.79±5.96×10^3/\mu l$ and $24.01±3.81×10^3/\mu l$, respectively (day −7). Values are comparable to vehicle control group and cgtx-544 therapy group. Within seven days, WBC count decreased slightly. Four days after arthritis induction, WBC count of the MTX high-dose therapy group increased again, probably due to acute inflammatory processes related to the induction. It cannot be said if this effect also occurs in cgtx-544 therapy group and vehicle control group, as for these two groups no EDTA whole blood was analyzed on this day. Also, for the MTX low-dose therapy group WBC count may not serve as an appropriate comparison, as the cytotoxic effect of MTX may influence the blood composition four days after arthritis induction. Another seven days after arthritis induction the WBC count further decreased in both MTX high-dose and low-dose therapy groups to $14.68±2.15×10^3/\mu l$ and $6.63±1.37×10^3/\mu l$, respectively (day 7) (FIG. 15), thus showing a cytostatic effect of MTX low-dose therapy. WBC counts decreased by nearly 50% compared to the beginning of the experiment. In contrast, the MTX high-dose therapy group's WBC count is comparable to those of cgtx-544 therapy group and vehicle control group.

1.2.2 Neutrophil Granulocytes

In the beginning of the experiment (day −21), absolute neutrophil granulocyte count of MTX high-dose and low-dose therapy group came to $1.55±0.52×10^3/\mu l$ and $1.93±0.6×10^3/\mu l$ respectively (FIG. 16A) (equal to 16.39±4.85% relative neutrophils of total WBC count and 16.64±4.07% relative neutrophils of total WBC count, respectively (FIG. 16B)). As WBC count, neutrophil granulocyte count also raised after the first and second immunization up to $7.54±3.19×10^3/\mu l$ and $10.77±2.7×10^3/\mu l$ respectively (day −7, equal to 35.46±7.08% of WBC and 44.33±5.4% of WBC, respectively). Within seven days, neutrophil granulocyte count decreased and seven days after induction counts of the MTX high-dose therapy group were comparable to those in the beginning of the experiment ($1.94±1.1×10^3/\mu l$, equal to 12.63±6.1% of WBC). This effect was also observed in cgtx-544 therapy group and vehicle control group. The MTX low-dose therapy group showed a much higher decrease with $0.33±0.36×10^3/\mu l$ neutrophil granulocytes (day 7, equal to 4.41±4.63% of WBC).

1.2.3 Lymphocytes

At the beginning of the experiment (day −21), the absolute lymphocyte count of MTX high-dose and low-dose therapy group came to $7.39±1.05×10^3/\mu l$ and $9.21±2.4×10^3/\mu l$, respectively (FIG. 17A) (equal to 78.77±4.76% of WBC and 78.97±3.94% of WBC, respectively (FIG. 17B)). Lymphocyte count in both MTX high-dose and low-dose therapy groups, in difference to WBC and neutrophil granulocyte counts, did not rise significantly after the first and second immunization, counting $11.68±2.8×10^3/\mu l$ and $11.83±1.35×10^3/\mu l$, respectively (day −7). This equals 57.01±6.45% of WBC and 49.83±5.45% of WBC, respectively (day −7), showing decreased percentages as the total WBC count strongly increased. Within seven days, lymphocyte percentage of WBC increased again and seven days after induction, in MTX high-dose therapy group, it was comparable to the percentage in the beginning of the experiment (78.16±7.20% of WBC, day 7) unlike in MTX low-dose therapy group, where it even became higher (93.13±4.66% of WBC, day 7). Absolute counts of MTX high-dose therapy group increased and MTX low-dose therapy group decreased, as compared to the beginning of the experiment: $11.38±1.15×10^3/\mu l$ and $6.14±1.11×10^3/\mu l$, respectively (day 7). Although the absolute lymphocyte count of MTX low-dose therapy group is reduced seven days after arthritis induction compared to the beginning of the experiment, it still represents about 93% of all white blood cells. This leads to the assumption that other subpopulations of leucocytes are more affected by the cytotoxic effect than the lymphocyte population.

Treatment with MTX leads to an inhibition of dihydrofolate reductase and results in a cytostatic effect on proliferating cells. Unlike individuals under cgtx-544 therapy, which did not show a generalized immunosuppression, MTX-treated individuals showed different effects in the haemograms compared to the vehicle control group. Seven days after arthritis induction, low-dose treated individuals had a reduction of WBC count, neutrophil granulocyte count and lymphocyte count. Furthermore, this results in a different composition of all white blood cell percentages. Furthermore, we observed a much smaller reduction of knee swelling compared to 60% in cgtx-544 therapy rats 24 h after arthritis induction in both MTX regimes (7% and 15%).

For the statistical analysis of MTX efficacy results the Welsh two sample t-test was used. In the following the statistical analysis of all tested MTX dose levels (0.1 mg/kg BW i.v. and 1 mg/kg BW s.c.) are shown for day 1 and 3 (FIG. 28).

In summary, treatment with MTX leads to an inhibition of the dihydrofolate reductase and results in a cytostatic effect on proliferating cells. Unlike individuals under cgtx-544 peptide therapy MTX-treated individuals showed different effects in the haemogram compared to the vehicle control group. Seven days after arthritis induction, low-dose treated individuals had a reduction of WBC count, neutrophil granulocyte count and lymphocyte count. Additionally, this results in a different composition of all white blood cell percentages. Furthermore, we observed a much smaller reduction of knee swelling compared to maximal 70% in cgtx-544 peptide therapy rats 24 h after arthritis induction in both MTX regimens (7% and 15%).

Example 7—Further Characterization of cgtx-544

The cgtx-544 peptide consists of 38 natural amino acids without modifications and has a molecular weight of approximately 4220 Da. It shares certain functional domain similarities with the α-KTx6 subfamily of scorpion peptides. cgtx-544 is restrained by 4 disulphide bridges and the 3D structure comprises an α-helix/β-sheet conformation.

Manufacturing cgtx-544

FIG. 29 provides a schematic view of the manufacturing steps of the cgtx-544 peptide. Peptide synthesis is carried out on an insoluble polystyrol resin with an F-moc strategy. The free N-terminal amine of a solid-phase attached peptide is coupled to a single N-protected amino acid unit. This unit is then deprotected (F-moc groups are cleaved at basic pH by piperidine), revealing a new N-terminal amine to which a further amino acid may be attached. Tert.-Butyloxycarbonyl (Boc) groups serve as permanent side chain protection groups and are cleaved after the peptide synthesis is finished by treatment with TFA (trifluoroacetic acid).

After completion of peptide synthesis the peptide is deprotected and cleaved from the polystyrol resin. At this point the raw peptide product displays a purity of about 50% followed by analytical UPLC and LC-MS. In a subsequent step the raw peptide is purified by preparative HPLC resulting in a linear peptide product with a purity of ≥90%.

Folding of the cgtx-544 Peptide

This peptide solution is being folded by oxidation (formation of disulfide bonds). The folding method is based on bond formation in phosphate buffer at pH 8.3 in the presence of atmospheric oxygen. HPLC analysis of cgtx-544 folded according to this protocol displayed that the peptide exists as a mixture of folded and partially folded variants. This intermediate folding product is referred to as cgtx-544(Mix). Based on electrophysiological data generated with material of different isolated UPLC-peaks it was concluded that one peak (retention time 12.77 min) in the folding mixture correlates with the native active peptide whereas all other peaks did not correlate with electrophysiological activity (FIG. 30). Thus, after the folding reaction the active peptide (retention time 12.77 min) was purified from the cgtx-544 mixture of folded and partially folded peptides by preparative HPLC. After this purification step the active peptide—referred to as cgtx-544(Sing)—usually has an estimated purity of more than 95%. The purified cgtx-544(Sing) peptide is highly soluble and stable in 0.9% NaCl solution at RT and 4° C. for up to several weeks.

Due to process development the purified peptide cgtx-544(Sing) was produced in a small scale format only. Thus, material was limited and was used in experiments intended to identify the $IC_{50}$ values of cgtx-544(Sing) on Kv1.3, Kv1.1, Kv1.2 and Kv1.5 (see Example 8). The unpurified folding mixture of cgtx-544 (cgtx-544(Mix)) was used in all other experiments described herein (Examples 1 to 6) unless otherwise indicated by the term cgtx-544 (sing). The content of active material in the mixture was calculated to be 15%.

In summary, the cgtx-544 peptide displays the following biochemical properties becoming important for biochemical analysis:

cgtx-544 is a highly basic peptide, containing 6 lysine and 2 arginine amino acids and is able to stick to surfaces of glass vials at low concentrations (<100 ng/ml).

It contains 8 cysteine amino acids, which are connected by 4 disulfide bridges.

Isoelectric point: 9.29.

MW: 4212 Da when disulfide bridges are bound, MW: 4220.2 Da in the reduced form

Due to the presence of 4 disulfide bridges the structure of cgtx-544 is compact.

Example 8—Further Characterization of Ion Channel Selectivity of Cgtx-544 (Sing) Based on Electrophysiological Analysis 1. Materials and Methods Ion channels were expressed via Baculovirus (Kv1.1-, Kv1.3- and Kv1.5-constructs) infected Sf21 cells or stably transfected CHO cells (Kv1.2) as described in Examples 1, 2, and 4. Electrophysiological analysis was performed on the automated patch clamp device "Patchliner" (Nanion Technologies, Munich, Germany). The Patchliner is based on a planary patch clamp method borosilicate glass chip (NPC-16) instead of a glass pipettes. The Patchliner is able to record four cells at the same time. All channel recordings were made in the whole cell mode. Data recordings were performed with the PatchMaster software (HEKA Electronics, Lambrecht/Pfalz, Germany). Visualization of experimental results was realized with IGOR software (Wavemetrics, USA). Average data are presented as mean±standard error of the mean (SEM).

Test compounds were used as concentrated stock solutions (mostly 1.5 µg/µl). Stock solutions were diluted in buffer to the required final concentrations.

2. Results 2.1 $IC_{50}$—Analysis of the Target Channel Kv1.3

After chemical synthesis (see Example 7) the peptide was folded by oxidation with atmospheric oxygen and the correctly folded (biologically active) peptide fraction was purified by preparative HPLC. This purified cgtx-544 peptide was designated cgtx-544(Sing) for singular peak.

Electrophysiological analysis of cgtx-544(Sing) resulted in an excellent $IC_{50}$ value of 6.9 nM (FIG. 31).

2.2 Electrophysiological Analysis of cgtx-544(Sing) on Kv1.1, Kv1.2 and Kv1.5

Electrophysiological analysis of cgtx-544(Sing) on Kv1.1, Kv1.2 and Kv1.5 demonstrated that cgtx-544 is highly selective. The results of the electrophysiological characterization of cgtx-544(Sing) on Kv1.1, Kv1.2 and Kv1.5 is summarized in FIG. 32.

Example 9—Protease Resistance of cgtx-544(Sing)

Figure 33:
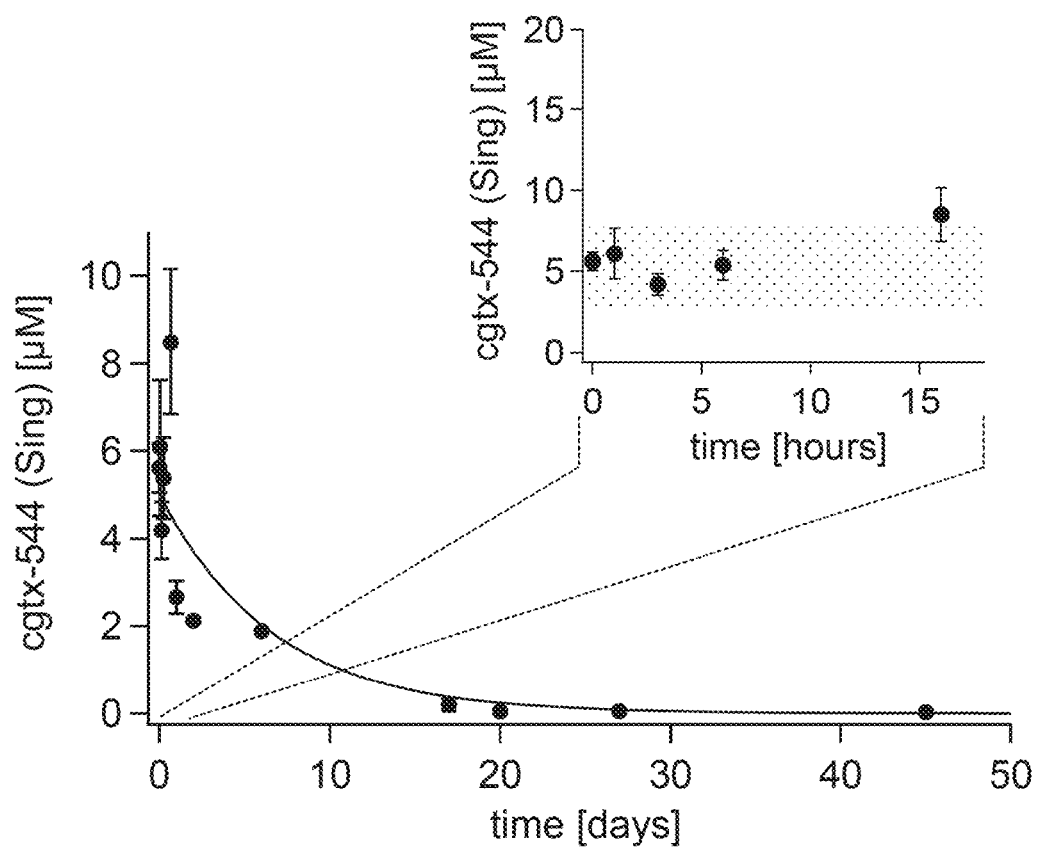

Further to the experiments described in Example 3, the stability of the cgtx-544 peptide was tested in blood serum samples under in vitro conditions. Thus, the stability of cgtx-544(Sing) in human blood serum was determined by the addition of a known quantity of cgtx-544(Sing) to human blood serum and a subsequent incubation at 37° C. The blocking activity of ctx-544(Sing) was measured on Kv1.3 channels over a period of 57 days. cgtx-544(Sing) is extremely stable in human blood serum. Its activity remains constant for at least 16 hours, and decays slowly until no more peptide blocking effect is detectable after 57 days. This demonstrates that cgtx-544 is very resistant to the action of blood proteases (FIG. 33).

No reduction in blocking potency is observed relative to the measurements done in the absence of serum, with the IC50 remaining in the 7 nM range. Serum control samples without peptide showed no unspecific block of Kv1.3. Therefore, it was concluded that the blocking effect seen is solely due to the effect of cgtx-544(Sing). Representing the concentration of cgtx-544(Sing) measured in the incubated solution over the 57 days, 50% activity of cgtx-544(Sing) was retained for a period of 5 days in human serum at 37° C.

In summary, the persistence of cgtx-544 in human serum at 37° C. is very high. cgtx-544 does not bind to serum components—if at all only with very low affinities—and is extremely resistant to degradation by proteases present in human serum.

Example 10—In Vivo Half-Life of cgtx-544 (Sing)

The aim of this study was to implement a bioassay to assess the in vivo half-life of cgtx-544(Sing) in the rat. Previous experiments (Example 3) had shown that cgtx-544 is not rapidly degraded when spiked into serum and incubated at 37° C.

1. Materials and Methods

Rats received i.v. injections of cgtx-544(Sing) (750 µg/kg BW). Blood was withdrawn at time points 0, 1, 10 and 60 minutes. Subsequently, serum was prepared from blood samples. The cgtx-544 content in these samples was analyzed electrophysiologically by measuring the blocking effect on Kv1.3 channels expressed in CHO cells. The serum control sample without peptide (0 minutes) showed no unspecific block of Kv1.3, and cgtx-544(Sing) activity of the 1 minute sample was regarded as 100%. The sample collected at the third time point (60 minutes) exhibited 10% of the original blocking activity. In order to study the amount of unbound cgtx-544(Sing) in the rat, the amount of cgtx-544(Sing) present in the circulating blood at the time points referred above was calculated through a calibration curve. This calibration curve was obtained by adding known quantities of cgtx-544(Sing) to blood serum and subsequent electrophysiological measurements on Kv1.3 channels. The block of Kv1.3 currents by these spiked samples was similar to that obtained with cgtx-544(Sing) in the absence of serum (data not shown).

2. Results

Figure 34:
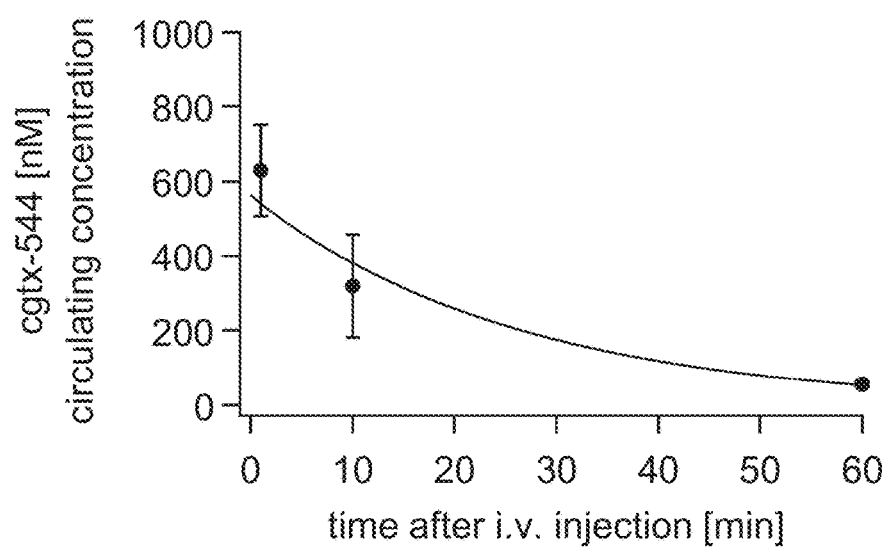

The decay of cgtx-544(Sing) in the blood of treated rats follows the typical decay curve, yielding a half-life of circa $t_{1/2}$=26 min (FIG. 34), with an approximate concentration of 62 nM of cgtx-544(Sing) in the circulating blood. This concentration is sufficient to achieve a full block of the Kv1.3 channels. This half-life is in the range seen for other peptide channel blockers—variants of the ShK toxin display a half-life between 20 to 50 min.

In summary, the in vivo half-life of cgtx-544 after i.v. application in the rat is in the range of the competitor peptide ShK. In vivo half-life is approximately 26 minutes. Because of the small size and compact structure of cgtx-544 it is assumed that the peptide is cleared from the blood most likely via renal filtration. It is reasonable to assume that the half-life of cgtx-544 in humans is longer than in rats, because the rat has a much faster metabolic rate than humans. The in vivo half-life does not correspond to the duration of the drug effect as the peptide tightly binds to the ion channel and blocks it for long time periods.

Example 11—Clinical Data

No clinical studies have been performed to date.
First-in-Man Study

A phase 1 study may be a randomized, double-blind, placebo-controlled, single-centre trial in healthy subjects.

The first part of this study may be a single-dose, dose-escalation study in cohorts of 4 subjects (3+1) for the lower dose groups and 8 subjects (2+6) for the higher dose groups. The starting dose will be estimated from the NOAEL in toxicity studies as laid down in the FDA guidance for industry "estimating the maximum safe starting dose in initial clinical trials for therapeutics in adult healthy volunteers".

The second part of the phase 1a may be designed as a multiple dose study. One cohort of 8 subjects (6+2) will be exposed to one dose level below the MTD for 7 consecutive daily applications.

The primary goal of this standard phase 1a study may be to evaluate the safety, tolerability and pharmacokinetics of cgtx-544 in healthy subjects.
Proof-of-Concept Study This phase 2a study may be a randomized, double-blind, placebo-controlled, multi-centre, proof-of-concept and dose-finding study in patients with moderate-to-severe plaque psoriasis.

The planed phase 2a proof of concept study will include 80 adult patients (20+60) and 3 dose levels. Each dose level will be tested with 20 patients for a period of 12 weeks.

Primary endpoint: Proportion of subjects who achieve PASI 75 (patients who has an improvement from baseline PASI of at least 75%) in week 12.

Secondary endpoints: Evaluation of the safety of cgtx-544 for up to 12 weeks by assessing adverse events, vital signs, laboratory parameters, physical examination and EEGs.

Pharmacokinetics of cgtx-544 at different time points for 12 weeks after the first treatment. Proportion of subjects who achieve IGA score "clear" or "almost clear" in week 12.

Proportion of subjects who achieve PASI 50 (patients who has an improvement from baseline PASI of at least 50%) in week 12.

Proportion of subjects who achieve PASI 90 (patients who has an improvement from baseline PASI of at least 90%) in week 12.

Similar studies can be done for vasculitis. The endpoints will have to be assessed accordingly.

The invention claimed is:

1. A composition comprising a peptide having the amino acid sequence $X_1$-$X_2$-$X_3$-N-V-$X_4$-C-$X_5$-$X_6$-$X_7$-$X_8$-$X_9$-C-$X_{10}$-$X_{11}$-$X_{12}$-C-$X_{13}$-$X_{14}$-$X_{15}$-T-G-C-P-$X_{16}$-$X_{17}$-K-C-M-N-R-K-C-$X_{18}$-C-$X_{19}$-$X_{20}$-C as set forth in SEQ ID NO: 23:
  wherein $X_1$ is selected from the group consisting of T, Q, S, Y and N;
  wherein $X_2$ is selected from the group consisting of I, F, V, A, L and W;
  wherein $X_3$ is selected from the group consisting of I, T, Y, S, V, A and L;
  wherein $X_4$ is selected from the group consisting of K, S, T, Y and R;
  wherein $X_5$ is selected from the group consisting of R, T, K, S and Y;
  wherein $X_6$ is selected from the group consisting of T, G, S, N, I, K, Q, A, V, L and Y;
  wherein $X_7$ is selected from the group consisting of P, S and T;
  wherein $X_8$ is selected from the group consisting of R, K and P;
  wherein $X_9$ is selected from the group consisting of D, Q, N and E;
  wherein $X_{10}$ is selected from the group consisting of A, Y, I, L, W, S, T, V, L and F;
  wherein $X_{11}$ is selected from the group consisting of D, R, P, K, E, S, T and Y;
  wherein $X_{12}$ is selected from the group consisting of P, H, V, I, L and A;
  wherein $X_{13}$ is selected from the group consisting of R, K, Q and N;
  wherein $X_{14}$ is selected from the group consisting of K, D, A, R, E, V, L and I;
  wherein $X_{15}$ is selected from the group consisting of E, Q, A, L, D, N, V and I;
  wherein $X_{16}$ is selected from the group consisting of Y, N, S, T and Q;
  wherein $X_{17}$ is selected from the group consisting of A, G, V, I and L;
  wherein $X_{18}$ is selected from the group consisting of K and R;
  wherein $X_{19}$ is selected from the group consisting of Y, N, Q, T and S; and
  wherein $X_{20}$ is selected from the group consisting of G, R and K.

2. The composition of claim 1:
  wherein $X_1$ is Thr;
  wherein $X_2$ is Ile;
  wherein $X_3$ is Ile;
  wherein $X_4$ is Lys;
  wherein $X_5$ is Thr;
  wherein $X_6$ is Ser;
  wherein $X_7$ is Pro;
  wherein $X_5$ is Lys;

wherein $X_9$ is Gln;
wherein $X_{10}$ is Leu;
wherein $X_{11}$ is Pro;
wherein $X_{12}$ is Pro;
wherein $X_{13}$ is Lys;
wherein $X_{14}$ is Ala;
wherein $X_{15}$ is Gln;
wherein $X_{16}$ is Tyr;
wherein $X_{17}$ is Gly;
wherein $X_{18}$ is Lys;
wherein $X_{19}$ is Asn; and
wherein $X_{20}$ is Arg.

3. A pharmaceutical composition comprising the composition of claim 1 and a pharmaceutically acceptable carrier.

4. A pharmaceutical composition comprising the composition of claim 2 and a pharmaceutically acceptable carrier.

5. The composition of claim 3, wherein the composition is formulated for intravenous, subcutaneous, or intramuscular administration.

6. The composition of claim 4, wherein the composition is formulated for intravenous, subcutaneous, or intramuscular administration.

7. A method of treating an autoimmune disease in a subject in need thereof, comprising administering the composition of claim 1 to a subject selected as having an autoimmune disease, wherein the autoimmune disease is rheumatoid arthritis, psoriasis, or atopic dermatitis.

8. The method of claim 7, wherein the composition is the composition of claim 2.

9. The method of claim 7, wherein administering the composition comprises administering the composition to the subject intravenously, subcutaneously, or intramuscularly.

10. The method of claim 8, wherein administering the composition comprises administering the composition to the subject intravenously, subcutaneously, or intramuscularly.

* * * * *

UNITED STATES PATENT AND TRADEMARK OFFICE
CERTIFICATE OF CORRECTION

PATENT NO. : 10,370,413 B2
APPLICATION NO. : 15/309781
DATED : August 6, 2019
INVENTOR(S) : Klostermann et al.

Page 1 of 2

It is certified that error appears in the above-identified patent and that said Letters Patent is hereby corrected as shown below:

On the Title Page

Item (56), Column 2, Line 11, under U.S. Patent Documents, change "Kvl .3" to --Kv1.3--.

In the Specification

Column 1, Line 50, change "perform" to --perforin--.

Column 2, Line 13 (approx.), change "parodontitits." to --parodontitis.--.

Column 5, Line 4, change "knee" to --knee.--.

Column 5, Line 6, change "arthritis" to --arthritis.--.

Column 5, Line 10, change "mBSA" to --mBSA.--.

Column 5, Line 15, change "animals)" to --animals).--.

Column 9, Line 15, change "(t0" to --(t0)--.

Column 14, Line 59, change "the the" to --the--.

Column 15, Line 14 (approx.), change "to understood" to --to be understood--.

Column 16, Line 11, change "K-$X_{16}$" to --K-C-$X_{16}$--.

Column 24, Line 4-5, change "selectivety" to --selectivity--.

Column 24, Line 7, change "ctgx" to --cgtx--.

Signed and Sealed this
         Sixteenth Day of June, 2020

Andrei Iancu
*Director of the United States Patent and Trademark Office*

CERTIFICATE OF CORRECTION (continued)

Column 24, Line 23, change "ctgx" to --cgtx--.

Column 25, Line 64, change "Guillian" to --Guillain--.

Column 26, Line 12, change "Behçet'disease," to --Behçet's disease,--.

Column 32, Line 17, change "NaoH" to --NaOH--.

Column 32, Line 43, change "1 µM" to --1 µM,--.

Column 33, Line 18, change "5 m" to --5 mM--.

Column 34, Lines 50-53 (approx.), delete "Usually, the effects of compound 1-8 could be also explained by run down effects of hERG currents. The results are shown in FIG. 3. A summary of the mean current block±SEM of all compounds are depicted in Table 1." and insert the same on Column 34, Line 50, as a continuation of the same paragraph.

Column 38, Line 19, change "pipeted" to --pipetted--.

Column 42, Line 54, change "Extend" to --Extent--.

Columns 42-43, Lines 63-67 (Column 42) 1-3 (Column 43), delete "Difference of absolute increase of swelling was calculated by subtracting left (un-induced) from right (induced) knee diameters. Calculated difference at the beginning of the experiment of both MTX high-dose and low-dose therapy groups was close to zero (0.01±0.06 mm and 0.0±0.03 mm respectively), as both knees are comparable in size. One day after arthritis induction, the difference raises up to 3.17±1.26 mm and 3.45±0.87 mm, respectively (FIG. 11)." and insert the same on Column 42, Line 62, as a continuation of the same paragraph.

Column 45, Line 25, change "Tert." to --Tert--.

Column 46, Line 8 (approx.), change "form" to --form.--.

Column 46, Line 24, change "planary" to --planar--.

Column 46, Line 61, change "ctx-544(Sing)" to --cgtx-544(Sing)--.

In the Claims

Column 111, Line 43, In Claim 1, change "$X_9C$" to --$X_9$-C--.

Column 112, Line 67, In Claim 2, change "$X_5$" to --$X_8$--.